US008017772B2

(12) United States Patent
Merla et al.

(10) Patent No.: US 8,017,772 B2
(45) Date of Patent: Sep. 13, 2011

(54) SUBSTITUTED TETRAHYDROPYRROLOPYRAZINE COMPOUNDS AND THE USE THEREOF IN THE TREATMENT AND/OR INHIBITION OF PAIN

(75) Inventors: Beatrix Merla, Aachen (DE); Thomas Christoph, Aachen (DE); Stefan Oberboersch, Aachen (DE); Klaus Schiene, Duesseldorf (DE); Gregor Bahrenberg, Aachen (DE); Robert Frank, Aachen (DE); Sven Kuehnert, Dueren (DE); Wolfgang Schroeder, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 12/558,008

(22) Filed: Sep. 11, 2009

(65) Prior Publication Data

US 2010/0004252 A1    Jan. 7, 2010

Related U.S. Application Data

(62) Division of application No. 11/873,574, filed on Oct. 17, 2007, now Pat. No. 7,625,900.

(60) Provisional application No. 60/851,995, filed on Oct. 17, 2006.

(30) Foreign Application Priority Data

Oct. 17, 2006   (DE) .................. 10 2006 049 452

(51) Int. Cl.
C07D 471/00    (2006.01)

(52) U.S. Cl. ........ 544/350; 544/106; 544/359; 546/152; 546/192; 546/268.1; 548/579; 549/59; 549/505

(58) Field of Classification Search .................. 544/106, 544/350, 359; 546/152, 192, 268.1; 548/579; 549/59, 505
See application file for complete search history.

(56) References Cited

U.S. PATENT DOCUMENTS

| 4,188,389 A | 2/1980 | Jirkovsky |
| 2002/0128277 A1 | 9/2002 | Dworetzky et al. |

FOREIGN PATENT DOCUMENTS

| CA | 2097465 A1 | 12/1993 |
| EP | 0 572 863 A1 | 12/1993 |
| WO | WO 94/29315 A1 | 12/1994 |
| WO | WO 03/024967 A2 | 3/2003 |
| WO | WO 03/084955 A1 | 10/2003 |
| WO | WO 2004/029040 A1 | 4/2004 |
| WO | WO 2004/052864 A1 | 6/2004 |

OTHER PUBLICATIONS

Hackam, et al. JAMA, 296(14), 2006, 1731-1732.*
Jordan, V.C. Nature Reviews: Drug Discovery, 2, 2003, p. 205.
Dörwald, F. Zaragoza. Side Reactions in Organic Synthesis: A Guide to Successful Synthesis Design, Weinheim: WILEY-VCH Verlag GmbH & Co. KGaA, 2005, Preface.
Patani, et al. Chem. Rev., 96, 1996, pp. 3147-3176.
German Search Report dated Oct. 28, 2006 with English translation of relevant portions (9 pages).
Bennett, Gary J., et al., "A Peripheral Mononeuropathy in Rat That Produces Disorders of Pain Sensation Like Those Seen in Man," Pain, 1988, pp. 87-107, vol. 33, 1988 Elsevier Science Publishers B.V.
Blackburn-Munro, Gordon, et al., "The Anticonvulsant Retigabine Attenuates Nociceptive Behaviors in Rat Models of Persistent and Neuropathic Pain," European Journal of Pharmacology, 2003, pp. 109-116, vol. 460, 2003 Elsevier Science Publishers B.V.
De Sarro, Giovambattista, et al., "Influence of Retigabine on the Anticonvulsant Activity of Some Antiepileptic Drugs Against Audiogenic Seizures in DBA/2 Mice," Naunyn-Schmiedeberg's Arch Pharmacology, 2001, pp. 330-336, vol. 363.
Dost, R., et al., "The Anti-Hyperalgesic Activity of Retigabine is Mediated by KCNQ Potassium Channel Activation," Naunyn-Schmiedeberg's Arch Pharmacology, 2004, pp. 382-390, vol. 369, Springer-Verlag 2004.
Gribkoff, Valentin K., "The Therapeutic Potential of Neuronal KCNQ Channel Modulators," Expert Opinion Ther. Targets, 2003, pp. 737-748, vol. 7, No. 6, Ashley Publications Ltd. 2003.
Hamill, O.P., et al., "Improved Patch-Clamp Techniques for High-Resolution Current Recording from Cells and Cell-Free Membrane Patches," Pfluegers Archiv European Journal of Physiology, 1981, pp. 85-100, vol. 391, Springer-Verlag 1981.
Kim, Sun Ho, et al., "An Experimental Model for Peripheral Neuropathy Produced by Segmental Spinal Nerve Ligation in the Rat," Pain, 1992, pp. 355-363, vol. 50, 1992 Elsevier Science Publishers B.V.

(Continued)

Primary Examiner — James O Wilson
Assistant Examiner — Douglas M Willis
(74) Attorney, Agent, or Firm — Crowell & Moring LLP

(57) ABSTRACT

Substituted tetrahydropyrrolopyrazine compounds corresponding to the formula I:

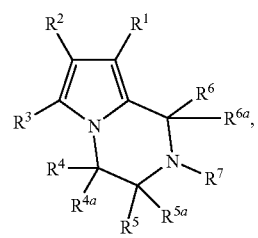

processes for their preparation, pharmaceutical compositions comprising these compounds and the use of these compounds for the treatment and/or inhibition of pain and other disorders or disease states at least partly mediated by KCNQ2/3 $K^+$ channels.

13 Claims, No Drawings

OTHER PUBLICATIONS

Korsgaard, M.P.G., et al., "Anxiolytic Effects of Maxipost (BMS-204352) and Retigabine Via Activation of Neuronal $K_v7$ Channels," The Journal of Pharmacology and Experimental Therapeutics, 2005, pp. 282-292, vol. 314, No. 1, 2005 The American Society for Pharmacology and Experimental Therapeutics.

Nielsen, Alexander Norup, et al., "Pharmacological Characterisation of Acid-Induced Muscle Allodynia in Rats," European Journal of Pharmacology, 2004, pp. 93-103, vol. 487, 2004 Elsevier B.V.

Passmore, Gayle M., et al., "KCNQ/M Currents in Sensory Neurons: Significance for Pain Therapy," The Journal of Neuroscience, Aug. 6, 2003, pp. 7227-7236, vol. 23, No. 18, 2003 Society for Neuroscience.

Streng, Tomi, et al., "Urodynamic Effects of the K+ Channel (KCNQ) Opener Retigabine in Freely Moving, Conscious Rats," The Journal of Urology, Nov. 2004, pp. 2054-2058, vol. 172, 2004 American Urological Association.

Wickenden, Alan D., et al., "KCNQ Potassium Channels: Drug Targets for the Treatment of Epilepsy and Pain," Expert Opinion Ther. Patents, 2004, vol. 14, No. 4, 2004 Ashley Publications Ltd.

Shirude, P.S., Kumar, V.A., Ganesh, K.N., (2S,5R/2R,5S)-Aminoethylpipecolyl *aepip-aeg*PNA chimera: synthesis and duplex/triplex stability, Tetrahedron 60: 9485-9492 (2004).

Nakao, K. et al., Quantitative Structure-Activity Analyses of Novel Hydroxyphenylurea Derivatives as Antioxidants, *Bioorg. Med. Chem.*, 6:849-868 (1998).

B. L. Bray et al., N-(Triisopropylsilyl)pyrrole, A progenitor "par excellence" of 3-substituted pyrroles, *J. Org. Chem.*, 55(26):6317-6328 (1990).

M. A. Marques et al, Toward an Understanding of the Chemical Etiology for DNA Minor-Broove Recognition by Polyamides, *Helvetica Chimica Acta* 85(12):4485-4517 (2002).

I. Jirkovski and R. Baudy, A Facile, Large-Scale Preparation of 1H-Pyrrole-1-ethanamine and Syntheses of Substituted Pyrrolo[1,2-a]pyrazines and Hydro Derivatives Thereof, *Synthesis*, pp. 481-483, Georg Thieme Verlag, Stuttgart—New York (1981).

I. Castellote et al., Pyrrolodiazines 6, Palladium-Catalyzed Arylation, Heteroarylation, and Amination of 3,4-Dihydropyrrolo[1,2-a]pyrazines, *J. Org. Chem.* 69(25):8668-8675 (2004).

English translation of the International Preliminary Report on Patentability dated May 15, 2009 (Ten (10) pages).

\* cited by examiner

SUBSTITUTED TETRAHYDROPYRROLOPYRAZINE COMPOUNDS AND THE USE THEREOF IN THE TREATMENT AND/OR INHIBITION OF PAIN

CROSS REFERENCE TO RELATED APPLICATIONS

This application is a division of application Ser. No. 11/873,574, filed Oct. 17, 2007, now U.S. Pat. No. 7,625,900, which in turn claims priority from U.S. provisional patent application No. 60/851,995, filed Oct. 17, 2006. Priority is also claimed based on Federal Republic of Germany patent application no. DE 10 2006 049 452.0, filed Oct. 17, 2006.

BACKGROUND OF THE INVENTION

The present invention relates to substituted tetrahydropyrrolopyrazine compounds, processes for their preparation, pharmaceutical compositions comprising these compounds and the use of these compounds for the treatment and/or inhibition of pain.

The treatment of pain, in particular neuropathic pain, is of great importance in medicine. There is a worldwide need for effective pain therapies. The longstanding need for a target-orientated treatment of chronic and non-chronic states of pain appropriate for the patient, by which is to be understood successful and satisfactory pain treatment for the patient, is also documented in the large number of scientific works which have been published in the field of applied analgesics and of fundamental research into nociception.

A pathophysiological feature of chronic pain is the over-excitability of neurons. Neuronal excitability is influenced decisively by the activity of $K^+$ channels, since these determine decisively the resting membrane potential of the cell and therefore the excitability threshold. Heteromeric $K^+$ channels of the molecular subtype KCNQ2/3 (Kv7.2/7.3) are expressed in neurons of various regions of the central (hippocampus, amygdala) and peripheral (dorsal root ganglia) nervous system and regulate the excitability thereof. Activation of KCNQ2/3 $K^+$ channels leads to a hyperpolarization of the cell membrane and, accompanying this, to a decrease in the electrical excitability of these neurons. KCNQ2/3-expressing neurons of the dorsal root ganglia are involved in the transmission of nociceptive stimuli from the periphery into the spinal marrow (Passmore et al., J. Neurosci. 2003; 23(18): 7227-36). It has accordingly been possible to detect an analgesic activity in preclinical neuropathy and inflammatory pain models for the KCNQ2/3 agonist retigabine (Blackburn-Munro and Jensen, Eur J Pharmacol 2003; 460(2-3); 109-16; post et al., Naunyn Schmiedebergs Arch Pharmacol 2004; 369(4): 382-390). The KCNQ2/3 $K^+$ channel thus represents a suitable starting point for the treatment of pain; in particular pain chosen from the group consisting of chronic pain, neuropathic pain, inflammatory pain and muscular pain (Nielsen et al., Eur J. Pharmacol. 2004; 487(1-3): 93-103), in particular neuropathic and inflammatory pain.

Moreover, the KCNQ2/3 $K^+$ channel is a suitable target for therapy of a large number of further diseases, such as, for example, migraine (US2002/0128277), cognitive diseases (Gribkoff, Expert Opin Ther Targets 2003; 7(6): 737-748), anxiety states (Korsgaard et al., J Pharmacol Exp Ther. 2005, 14(1): 282-92), epilepsy (Wickenden et al., Expert Opin Ther Pat 2004; 14(4): 457-469) and urinary incontinence (Streng et al., J Urol 2004; 172: 2054-2058).

Substituted tetrahydropyrrolopyrazines are known from the literature and from databanks. Thus, U.S. Pat. No. 4,188, 389 discloses tetrahydropyrrolopyrazines which are suitable for treatment of depression. WO 94/29315 discloses tetrahydropyrrolopyrazines having anxiolytic properties, which are unsubstituted on the piperazine ring except for on the piperazine nitrogen. WO 2003/024967 discloses tetrahydropyrrolopyrazines which carry a (C—Z)—$NH_2$ substituent on $R^3$ and are suitable for treatment of cancer. Tetrahydropyrrolopyrazines are furthermore listed in databanks, for example at CAS, without any biological activity being mentioned.

BRIEF SUMMARY OF THE INVENTION

One object of the present invention was therefore to provide new compounds and pharmaceutical compositions which are suitable for the treatment and/or inhibition of pain.

Another object of the invention was to provide compounds and pharmaceutical compositions which can be used for treatment of disorders or diseases which are at least partly mediated by KCNQ2/3 $K^+$ channels.

A further object of the invention was to provide new methods for treating and/or inhibiting pain or other disorders or disease states at least partly mediated by KCNQ2/3 $K^+$ channels.

These and other objects have been achieved by the invention as described and claimed hereinafter.

It has now been found, surprisingly, that substituted tetrahydropyrrolopyrazine compounds of formula I given below are suitable for treatment of pain and also have an excellent affinity for the KCNQ2/3 $K^+$ channel and are therefore suitable for treatment of disorders or diseases which are at least partly mediated by KCNQ2/3 $K^+$ channels.

The present invention therefore provides substituted tetrahydropyrrolopyrazine compounds corresponding to formula I:

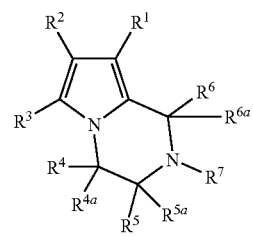

wherein
$R^1$, $R^2$ and $R^3$ independently of one another represent hydrogen, $C_{1-6}$-alkyl, saturated or unsaturated, branched or unbranched, unsubstituted or mono- or poly-substituted; F, Cl, Br, I, CN, $NH_2$, NH—$C_{1-6}$-alkyl, NH—$C_{1-6}$-alkyl-OH, N($C_{1-6}$alkyl)$_2$, N($C_{1-6}$-alkyl-OH)$_2$, NHaryl; NH-alkylaryl; NH-heteroaryl; $NO_2$, SH, S—$C_{1-6}$-alkyl, OH, O—$C_{1-6}$-alkyl, O—$C_{1-6}$alkyl-OH, C(=O)$C_{1-6}$-alkyl, $NHSO_2C_{1-6}$-alkyl, NHCOaryl; NHCOC$_{1-6}$-alkyl, $CO_2H$, $CH_2SO_2$-phenyl, $CO_2$—$C_{1-6}$-alkyl, $OCF_3$, $SCF_3$, $CF_3$, benzyloxy, morpholinyl, pyrrolidinyl, piperidinyl, piperazinyl, phenoxy, phenyl, pyridyl, alkylaryl, thienyl or furyl; or
$R^1$ and $R^2$ or $R^2$ and $R^3$ form a ring and together denote

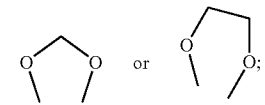

$R^4$ and $R^5$ independently of one another represent H, F, Cl, Br, I, —CN, $NH_2$, NH—$C_{1-6}$-alkyl, NH—$C_{1-6}$-alkyl-OH, $C_{1-6}$-alkyl, N($C_{1-6}$-alkyl)$_2$, N($C_{1-6}$-alkyl-OH)$_2$, $NO_2$, SH, S—$C_{1-6}$-alkyl, S-benzyl, O—$C_{1-6}$-alkyl, OH, O—$C_{1-6}$-alkyl-OH, O-benzyl, C(=O)$C_{1-6}$-alkyl, $CO_2H$, $CO_2$—$C_{1-6}$-alkyl or benzyl;

$R^6$ represents $C_{1-6}$-alkyl, branched or unbranched, unsubstituted or mono- or poly-substituted; aryl or heteroaryl, unsubstituted or mono- or poly-substituted; or aryl or heteroaryl radical linked via a $C_{1-3}$-alkyl chain and unsubstituted or mono- or poly-substituted;

$R^{4a}$, $R^{5a}$ and $R^{6a}$ independently of one another represent H or $C_{1-6}$-alkyl;

$R^7$ represents $(CH_2)_tC(=O)R^8$; $(C=O)(CH_2)_mNR^{11}R^{12}$; $C(=O)(CH_2)_n(C=O)R^8$; or
$(CH_2)_sNHC(=O)R^8$, wherein
m represents 1, 2 or 3, and
n, t and s each represents 1, 2, 3 or 4;

$R^8$ denotes $C_{1-6}$-alkyl, saturated or unsaturated, branched or unbranched, unsubstituted or mono- or poly-substituted; aryl, heteroaryl, heterocyclyl or $C_{3-8}$-cycloalkyl, in each case unsubstituted or mono- or poly-substituted; or aryl, heteroaryl, heterocyclyl or $C_{3-8}$-cycloalkyl linked via a $C_{1-5}$-alkyl chain and in each case unsubstituted or mono- or poly-substituted, wherein the alkyl chain in each case can be saturated or unsaturated, branched or unbranched; $NR^9R^{10}$; wherein $R^9$ and $R^{10}$ independently of one another represent H; $C_{1-6}$-alkyl, in each case saturated or unsaturated, branched or unbranched, mono- or poly-substituted or unsubstituted; aryl or heteroaryl, in each case unsubstituted or mono- or poly-substituted; heterocyclyl or $C_{3-8}$-cycloalkyl, in each case saturated or unsaturated, mono- or poly-substituted or unsubstituted; $C(=O)R^{20}$; $SO_2R^{13}$; or aryl, $C_{3-8}$-cycloalkyl, heterocyclyl or heteroaryl bonded via $C_{1-3}$-alkyl and in each case mono- or poly-substituted or unsubstituted, wherein the alkyl chain in each case can be saturated or unsaturated, branched or unbranched; or $R^9$ and $R^{10}$ together represent $CH_2CH_2OCH_2CH_2$, $CH_2CH_2NR^{14}CH_2CH_2$ or $(CH_2)_{3-6}$, $R^{11}$ and $R^{12}$ independently of one another represent H; $C_{1-6}$-alkyl, in each case saturated or unsaturated, branched or unbranched, mono- or poly-substituted or unsubstituted; heterocyclyl or $C_{3-8}$-cycloalkyl, in each case saturated or unsaturated, mono- or poly-substituted or unsubstituted; $C(=O)R^{20}$; $SO_2R^{13}$; or aryl, $C_{3-8}$-cycloalkyl, heterocyclyl or heteroaryl bonded via $C_{1-3}$-alkyl and in each case mono- or poly-substituted or unsubstituted, wherein the alkyl chain in each case can be saturated or unsaturated, branched or unbranched; or $R^{11}$ and $R^{12}$ together represent $CH_2CH_2OCH_2CH_2$, $CH_2CH_2NR^{14}CH_2CH_2$ or $(CH_2)_{3-6}$, wherein $R^{14}$ denotes H; $C_{1-6}$-alkyl, in each case saturated or unsaturated, branched or unbranched, mono- or poly-substituted or unsubstituted; $C_{3-8}$-cycloalkyl, in each case saturated or unsaturated, mono- or poly-substituted or unsubstituted; aryl or heteroaryl, in each case mono- or poly-substituted or unsubstituted; C(=O)$R^{13}$; or aryl, $C_{3-8}$-cycloalkyl or heteroaryl bonded via $C_{1-3}$-alkyl and in each case mono- or poly-substituted or unsubstituted;

$R^{13}$ denotes $C_{1-6}$-alkyl, saturated or unsaturated, branched or unbranched, unsubstituted or mono- or poly-substituted; aryl, heteroaryl or $C_{3-8}$-cycloalkyl, in each case unsubstituted or mono- or poly-substituted; or aryl, heteroaryl or $C_{3-8}$-cycloalkyl linked via a $C_{1-5}$-alkyl chain and in each case unsubstituted or mono- or poly-substituted, wherein the alkyl chain in each case can be saturated or unsaturated, branched or unbranched;

$R^{20}$ denotes $C_{1-6}$-alkyl, saturated or unsaturated, branched or unbranched, unsubstituted or mono- or poly-substituted; aryl, heteroaryl or $C_{3-8}$-cycloalkyl, in each case unsubstituted or mono- or poly-substituted; $NR^{21}R^{22}$; or aryl, heteroaryl or $C_{3-8}$-cycloalkyl linked via a $C_{1-5}$-alkyl chain and in each case unsubstituted or mono- or poly-substituted, wherein the alkyl chain in each case can be saturated or unsaturated, branched or unbranched; wherein $R^{21}$ and $R^{22}$ independently of one another denote $C_{1-6}$-alkyl, saturated or unsaturated, branched or unbranched, unsubstituted or mono- or poly-substituted; aryl, heteroaryl or $C_{3-8}$-cycloalkyl, in each case unsubstituted or mono- or poly-substituted; or aryl, heteroaryl or $C_{3-8}$-cycloalkyl linked via a $C_{1-5}$-alkyl chain and in each case unsubstituted or mono- or poly-substituted, wherein the alkyl chain in each case can be saturated or unsaturated, branched or unbranched, in the form of the racemate; of the enantiomers, diastereomers, mixtures of the enantiomers or diastereomers or of an individual enantiomer or diastereomer; of the bases and/or salts of physiologically acceptable acids.

DETAILED DESCRIPTION OF THE INVENTION

The present invention provides substituted tetrahydropyrrolopyrazine compounds corresponding to formula I:

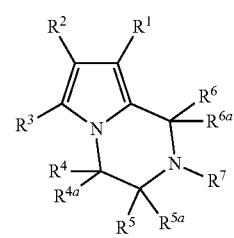

wherein
$R^1$, $R^2$ and $R^3$ independently of one another represent hydrogen, $C_{1-6}$-alkyl, saturated or unsaturated, branched or unbranched, unsubstituted or mono- or poly-substituted; F, Cl, Br, I, CN, $NH_2$, NH—$C_{1-6}$-alkyl, N($C_{1-6}$alkyl)$_2$, N($C_{1-6}$-alkyl-OH)$_2$, NHaryl; NH-alkylaryl; NH-heteroaryl; $NO_2$, SH, S—$C_{1-6}$-alkyl, OH, O—$C_{1-6}$-alkyl, O—$C_{1-6}$alkyl-OH, C(=O)$C_{1-6}$-alkyl, $NHSO_2C_{1-6}$-alkyl, NHCOaryl; NHCO$C_{1-6}$-alkyl, $CO_2H$, $CH_2SO_2$-phenyl, $CO_2$—$C_{1-6}$-alkyl, $OCF_3$, $SCF_3$, $CF_3$, benzyloxy, morpholinyl, pyrrolidinyl, piperidinyl, piperazinyl, phenoxy, phenyl, pyridyl, alkylaryl, thienyl or furyl; or $R^1$ and $R^2$ or $R^2$ and $R^3$ form a ring and together denote

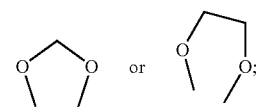

$R^4$ and $R^5$ independently of one another represent H, F, Cl, Br, I, —CN, $NH_2$, NH—$C_{1-6}$-alkyl, NH—$C_{1-6}$-alkyl-OH, $C_{1-6}$-alkyl, $N(C_{1-6}$-alkyl$)_2$, $N(C_{1-6}$-alkyl-OH$)_2$, $NO_2$, SH, S—$C_{1-6}$-alkyl, S-benzyl, O—$C_{1-6}$-alkyl, OH, O—$C_{1-6}$-alkyl-OH, O-benzyl, C(=O)$C_{1-6}$-alkyl, $CO_2H$, $CO_2$—$C_{1-6}$-alkyl or benzyl;

$R^6$ represents $C_{1-6}$-alkyl, branched or unbranched, unsubstituted or mono- or poly-substituted; aryl or heteroaryl, unsubstituted or mono- or poly-substituted; or aryl or heteroaryl radical linked via a $C_{1-3}$-alkyl chain and unsubstituted or mono- or poly-substituted;

$R^{4a}$, $R^{5a}$ and $R^{6a}$ independently of one another represent H or $C_{1-6}$-alkyl;

$R^7$ represents $(CH_2)_tC(=O)R^8$; $(C=O)(CH_2)_mNR^{11}R^{12}$; $C(=O)(CH_2)_n(C=O)R^8$; or $(CH_2)_nNHC(=O)R^8$, wherein m represents 1, 2 or 3, and n, t and s each represents 1, 2, 3 or 4;

$R^8$ denotes $C_{1-6}$-alkyl, saturated or unsaturated, branched or unbranched, unsubstituted or mono- or poly-substituted; aryl, heteroaryl, heterocyclyl or $C_{3-8}$-cycloalkyl, in each case unsubstituted or mono- or poly-substituted; or aryl, heteroaryl, heterocyclyl or $C_{3-8}$-cycloalkyl linked via a $C_{1-5}$-alkyl chain and in each case unsubstituted or mono- or poly-substituted, wherein the alkyl chain in each case can be saturated or unsaturated, branched or unbranched; $NR^9R^{10}$; wherein $R^9$ and $R^{10}$ independently of one another represent H; $C_{1-6}$-alkyl, in each case saturated or unsaturated, branched or unbranched, mono- or poly-substituted or unsubstituted; aryl or heteroaryl, in each case unsubstituted or mono- or poly-substituted; heterocyclyl or $C_{3-8}$-cycloalkyl, in each case saturated or unsaturated, mono- or poly-substituted or unsubstituted; $C(=O)R^{20}$; $SO_2R^{13}$; or aryl, $C_{3-8}$-cycloalkyl, heterocyclyl or heteroaryl bonded via $C_{1-3}$-alkyl and in each case mono- or poly-substituted or unsubstituted, wherein the alkyl chain in each case can be saturated or unsaturated, branched or unbranched; or $R^9$ and $R^{10}$ together represent $CH_2CH_2OCH_2CH_2$, $CH_2CH_2NR^{14}CH_2CH_2$ or $(CH_2)_{3-6}$, $R^{11}$ and $R^{12}$ independently of one another represent H; $C_{1-6}$-alkyl, in each case saturated or unsaturated, branched or unbranched, mono- or poly-substituted or unsubstituted; heterocyclyl or $C_{3-8}$-cycloalkyl, in each case saturated or unsaturated, mono- or poly-substituted or unsubstituted; $C(=O)R^{20}$; $SO_2R^{13}$; or aryl, $C_{3-8}$-cycloalkyl, heterocyclyl or heteroaryl bonded via $C_{1-3}$-alkyl and in each case mono- or poly-substituted or unsubstituted, wherein the alkyl chain in each case can be saturated or unsaturated, branched or unbranched; or $R^{11}$ and $R^{12}$ together represent $CH_2CH_2OCH_2CH_2$, $CH_2CH_2NR^{14}CH_2CH_2$ or $(CH_2)_{3-6}$, wherein $R^{14}$ denotes H; $C_{1-6}$-alkyl, in each case saturated or unsaturated, branched or unbranched, mono- or poly-substituted or unsubstituted; $C_{3-8}$-cycloalkyl, in each case saturated, mono- or poly-substituted or unsubstituted; aryl or heteroaryl, in each case mono- or poly-substituted or unsubstituted; C(=O)$R^{13}$; or aryl, $C_{3-8}$-cycloalkyl or heteroaryl bonded via $C_{1-3}$-alkyl and in each case mono- or poly-substituted or unsubstituted;

$R^{13}$ denotes $C_{1-6}$-alkyl, saturated or unsaturated, branched or unbranched, unsubstituted or mono- or poly-substituted; aryl, heteroaryl or $C_{3-8}$-cycloalkyl, in each case unsubstituted or mono- or poly-substituted; or aryl, heteroaryl or $C_{3-8}$-cycloalkyl linked via a $C_{1-5}$-alkyl chain and in each case unsubstituted or mono- or poly-substituted, wherein the alkyl chain in each case can be saturated or unsaturated, branched or unbranched;

$R^{20}$ denotes $C_{1-6}$-alkyl, saturated or unsaturated, branched or unbranched, unsubstituted or mono- or poly-substituted; aryl, heteroaryl or $C_{3-8}$-cycloalkyl, in each case unsubstituted or mono- or poly-substituted; $NR^{21}R^{22}$; or aryl, heteroaryl or $C_{3-8}$-cycloalkyl linked via a $C_{1-5}$-alkyl chain and in each case unsubstituted or mono- or poly-substituted, wherein the alkyl chain in each case can be saturated or unsaturated, branched or unbranched; wherein $R^{21}$ and $R^{22}$ independently of one another denote $C_{1-6}$-alkyl, saturated or unsaturated, branched or unbranched, unsubstituted or mono- or poly-substituted; aryl, heteroaryl or $C_{3-8}$-cycloalkyl, in each case unsubstituted or mono- or poly-substituted; or aryl, heteroaryl or $C_{3-8}$-cycloalkyl linked via a $C_{1-5}$-alkyl chain and in each case unsubstituted or mono- or poly-substituted, wherein the alkyl chain in each case can be saturated or unsaturated, branched or unbranched, in the form of the racemate; of the enantiomers, diastereomers, mixtures of the enantiomers or diastereomers or of an individual enantiomer or diastereomer; of the bases and/or salts of physiologically acceptable acids.

In connection with "phenyl", "phenyloxy", "benzyl", "benzyloxy", "alkylaryl", the term in each case includes the unsubstituted structure and also the structure substituted by F, Cl, $OCH_3$, $CF_3$, $OCF_3$, $SCF_3$ and $CH_3$.

In the context of this invention, the expressions "$C_{1-3}$-alkyl", "$C_{1-5}$-alkyl" and "$C_{1-6}$-alkyl" include acyclic saturated or unsaturated hydrocarbon radicals, which can be branched- or straight-chain and unsubstituted or mono- or poly-substituted, having from 1 to 3 C atoms or, respectively, from 1 to 5 C atoms or, respectively, from 1 to 6 C atoms, i.e. $C_{1-3}$-alkanyls, $C_{2-3}$-alkenyls and $C_{2-3}$-alkynyls or, respectively, $C_{1-5}$-alkanyls, $C_{2-5}$-alkenyls and $C_{2-5}$-alkynyls or, respectively, $C_{1-6}$-alkanyls, $C_{2-6}$-alkenyls and $C_{2-6}$-alkynyls. In this context, alkenyls contain at least one C—C double bond and alkynyls contain at least one C—C triple bond. Alkyl is advantageously chosen from the group which includes methyl, ethyl, n-propyl, 2-propyl, n-butyl, iso-butyl, sec-butyl, tert-butyl, n-pentyl, iso-pentyl, neo-pentyl, hexyl, ethylenyl (vinyl), propenyl (—$CH_2CH=CH_2$, —CH=CH—$CH_3$, —C(=$CH_2$)—$CH_3$), propynyl (—CH—C≡CH, —C≡C—$CH_3$), butenyl, butynyl, pentenyl, pentynyl, hexenyl and hexynyl. Methyl, ethyl, n-propyl and iso-propyl are particularly advantageous.

For the purposes of this invention, the expression "cycloalkyl" or "$C_{3-8}$-cycloalkyl" denotes cyclic hydrocarbons having 3, 4, 5, 6, 7 or 8 carbon atoms, wherein the hydrocarbons can be saturated or unsaturated (but not aromatic), unsubstituted or mono- or poly-substituted. $C_{3-8}$-Cycloalkyl is advantageously chosen from the group which contains cyclopropyl, cyclobutyl, cyclopentyl, cyclohexyl, cycloheptyl, cyclooctyl, cyclopentenyl, cyclohexenyl, cycloheptenyl and cyclooctenyl.

The term "heterocyclyl" includes saturated or unsaturated (but not aromatic) cycloalkyls having from three to eight ring members, in which one or two hydrocarbon atoms have been replaced by a heteroatom S, N or O. Heterocyclyl radicals selected from the group consisting of tetrahydropyranyl, dioxanyl, dioxolanyl, morpholinyl, piperidinyl, piperazinyl, pyrazolinonyl and pyrrolidinyl are advantageous.

In the context of this invention the expression "aryl" denotes aromatic hydrocarbons having up to 14 ring members, inter alia phenyls and naphthyls. The aryl radicals can also be fused with further saturated, (partly) unsaturated or aromatic ring systems. Each aryl radical can be unsubstituted or mono- or poly-substituted, where the substituents on the aryl can be identical or different and in any desired and possible position of the aryl. Aryl is advantageously selected from the group consisting of phenyl, 1-naphthyl, and 2-naphthyl, each of which can be unsubstituted or mono- or poly-substituted.

The expression "heteroaryl" represents a 5-, 6- or 7-membered cyclic aromatic radical which contains at least 1, optionally also 2, 3, 4 or 5 heteroatoms, where the heteroatoms are identical or different and the heterocyclic ring can be unsubstituted or mono- or poly-substituted. In the case of substitution on the heterocyclic ring, the substituents can be identical or different and can be in any desired and possible position of the heteroaryl. The heterocyclic ring can also be part of a bi- or poly-cyclic system having up to 14 ring members. Preferred heteroatoms are nitrogen, oxygen and sulfur. It is preferable for the heteroaryl radical to be selected from the group consisting of pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxadiazolyl, isoxazoyl, pyridyl, pyridazinyl, pyrimidinyl, pyrazinyl, indazolyl, purinyl, indolizinyl, quinolinyl, isoquinolinyl, quinazolinyl, carbazolyl, phenazinyl and oxadiazolyl, where the bonding to the compounds of the general structure I can be effected via any desired and possible ring member of the heteroaryl radical. Pyridyl, furyl and thienyl are particularly preferred.

For the purposes of the present invention, the expressions "aryl, heteroaryl, heterocyclyl or cycloalkyl bonded via $C_{1-3}$-alkyl" and "aryl, heteroaryl or cycloalkyl bonded via $C_{1-5}$-alkyl" mean that $C_{1-3}$-alkyl and aryl and heteroaryl and heterocyclyl and cycloalkyl have the meanings defined above and the aryl or heteroaryl or heterocyclyl or cycloalkyl radical is bonded to the compound of the general structure I via a $C_{1-3}$-alkyl group or a $C_{1-5}$-alkyl group. The alkyl chain can in all cases be saturated or unsaturated, branched or unbranched, unsubstituted or mono- or poly-substituted. It is advantageous for the alkyl chain to be unsubstituted or substituted by a methyl group. Phenyl, benzyl and phenethyl are particularly advantageous in the context of this invention.

In connection with "alkyl", "heterocyclyl" and "cycloalkyl", in the context of this invention the term "substituted" is understood as meaning replacement of a hydrogen radical by F, Cl, Br, I, —CN, $NH_2$, NH—$C_{1-6}$-alkyl, NH—$C_{1-6}$-alkyl-OH, $C_{1-6}$-alkyl, $N(C_{1-6}$-alkyl$)_2$, $N(C_{1-6}$-alkyl-OH$)_2$, $NO_2$, SH, S—$C_{1-6}$-alkyl, S-benzyl, O—$C_{1-6}$-alkyl, OH, O—$C_{1-6}$-alkyl-OH, =O, O-benzyl, C(=O)$C_{1-6}$-alkyl, $CO_2H$, $CO_2$—$C_{1-6}$-alkyl, phenyl or benzyl, where polysubstituted radicals are to be understood as meaning those radicals which are substituted several times, e.g. two or three times, either on different or on the same atoms, for example three times on the same C atom as in the case of $CF_3$ or —$CH_2CF_3$, or at different places as in the case of —CH(OH)—CH=CH—$CHCl_2$. Polysubstitution can be with the same or with different substituents.

In respect of "aryl" and "heteroaryl", in the context of this invention "mono- or poly-substituted" is understood as meaning replacement once or several times, e.g. two, three or four times, of one or more hydrogen atoms of the ring system by F, Cl, Br, I, CN, $NH_2$, NH—$C_{1-6}$-alkyl, NH—$C_{1-6}$-alkyl-OH, $N(C_{1-6}$-alkyl$)_2$, $N(C_{1-6}$-alkyl-OH$)_2$, $NO_2$, SH, S—$C_{1-6}$-alkyl, OH, O—$C_{1-6}$-alkyl, O—$C_{1-6}$alkyl-OH, C(=O)$C_{1-6}$-alkyl, C(=O)$NHC_{1-6}$-alkyl; C(=O)-aryl; C(=O)—N-morpholine; C(=O)-piperidine; (C=O)-pyrrolidine; (C=O)-piperazine; $NHSO_2C_{1-6}$-alkyl, $NHCOC_{1-6}$-alkyl,

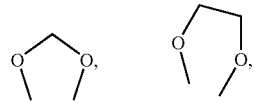

$CO_2H$, $CH_2SO_2$-phenyl, $CO_2$—$C_{1-6}$-alkyl, $OCF_3$, $SCF_3$, $CF_3$, $C_{1-6}$-alkyl, pyrrolidinyl, piperidinyl, morpholinyl, benzyloxy, phenoxy, phenyl, pyridyl, alkylaryl, thienyl or furyl; on one or optionally different atoms, where a substituent can optionally be substituted in its turn, but not with a further aryl or heteroaryl ring. Polysubstitution in this context is with the same or with different substituents. Preferred substituents for "aryl" or "heteroaryl" are F, Cl, $OCH_3$, $CF_3$, $OCF_3$, $SCF_3$ and $CH_3$.

In the context of this invention, the term of salt formed with a physiologically acceptable acid is understood as meaning salts of the particular active compound with inorganic or organic acids which are physiologically acceptable—in particular when used in humans and/or mammals. Examples of physiologically acceptable acids include hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, 1,1-dioxo-1,2-dihydrol$\lambda^6$-benzo[d]isothiazol-3-one (saccharic acid), monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, hippuric acid, phosphoric acid and/or aspartic acid. Salts of citric acid and hydrochloric acid are particularly preferred.

In the context of this invention, preference is given to substituted tetrahydro-pyrrolopyrazine compounds of formula I in which:

$R^1$, $R^2$ and $R^3$ independently of one another represent hydrogen, $C_{1-6}$-alkyl, saturated or unsaturated, branched or unbranched, unsubstituted or mono- or poly-substituted; F, Cl, Br, I, CN, $NH_2$, NH—$C_{1-6}$-alkyl, NH—$C_{1-6}$-alkyl-OH, $N(C_{1-6}$alkyl$)_2$, $N(C_{1-6}$-alkyl-OH$)_2$, NHaryl; NH-alkylaryl; NH-heteroaryl; $NO_2$, SH, S—$C_{1-6}$-alkyl, OH, O—$C_{1-6}$-alkyl, O—$C_{1-6}$alkyl-OH, C(=O)$C_{1-6}$-alkyl, $NHSO_2C_{1-6}$-alkyl, NHCOaryl; $NHCOC_{1-6}$-alkyl, $CO_2H$, $CH_2SO_2$-phenyl, $CO_2$—$C_{1-6}$-alkyl, $OCF_3$, $SCF_3$, $CF_3$, benzyloxy, morpholinyl, pyrrolidinyl, piperidinyl, piperazinyl, phenoxy, phenyl, pyridyl, alkylaryl, thienyl or furyl; or $R^1$ and $R^2$ or $R^2$ and $R^3$ form a ring and together denote

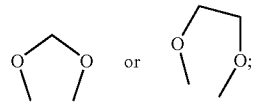

$R^4$ and $R^5$ independently of one another represent H, F, Cl, Br, I, —CN, $NH_2$, NH—$C_{1-6}$-alkyl, NH—$N(C_{1-6}$-alkyl$)_2$, $N(C_{1-6}$-alkyl-OH$)_2$, $NO_2$, SH, S—$C_{1-6}$-alkyl, S-benzyl, O—$C_{1-6}$-alkyl, OH, O—$C_{1-6}$-alkyl-OH, O-benzyl, C(=O)$C_{1-6}$-alkyl, $CO_2H$, $CO_2$—$C_{1-6}$-alkyl or benzyl;

$R^6$ represents $C_{1-6}$-alkyl, branched or unbranched, unsubstituted or mono- or poly-substituted; aryl or heteroaryl, unsubstituted or mono- or poly-substituted; or aryl or heteroaryl radical linked via a $C_{1-3}$-alkyl chain and unsubstituted or mono- or poly-substituted;

$R^{4a}$, $R^{5a}$ and $R^{6a}$ independently of one another represent H or $C_{1-6}$-alkyl; and $R^7$ represents $(CH_2)_tC(=O)R^8$; $(C=O)(CH_2)_mNR^{11}R^{12}$; $C(=O)(CH_2)_n(C=O)R^8$; $(CH_2)_sNHC(=O)R^8$; wherein m represents 1, 2 or 3;

n, t and s each represents 1, 2, 3 or 4

$R^8$ denotes $C_{1-6}$-alkyl, saturated or unsaturated, branched or unbranched, unsubstituted or mono- or poly-substituted; aryl, heteroaryl, heterocyclyl or $C_{3-8}$-cycloalkyl, in each case unsubstituted or mono- or poly-substituted; or aryl, heteroaryl, heterocyclyl or $C_{3-8}$-cycloalkyl linked via a $C_{1-5}$-alkyl chain and in each case unsubstituted or mono- or poly-substituted, wherein the alkyl chain in each case can be saturated or unsaturated, branched or unbranched; $NR^9R^{10}$; wherein $R^9$ and $R^{10}$ independently of one another represent H; $C_{1-6}$-alkyl, in each case saturated or unsaturated, branched or unbranched, mono- or poly-substituted or unsubstituted; aryl or heteroaryl, in each case unsubstituted or mono- or poly-substituted; heterocyclyl or $C_{3-8}$-cycloalkyl, in each case saturated or unsaturated, mono- or poly-substituted or unsubstituted; $C(=O)R^{20}$; $SO_2R^{13}$; or aryl, $C_{3-8}$-cycloalkyl, heterocyclyl or heteroaryl bonded via $C_{1-3}$-alkyl and in each case mono- or poly-substituted or unsubstituted, wherein the alkyl chain in each case can be saturated or unsaturated, branched or unbranched; or $R^9$ and $R^{10}$ together represent $CH_2CH_2OCH_2CH_2$, $CH_2CH_2NR^{14}CH_2CH_2$ or $(CH_2)_{3-6}$, $R^{11}$ and $R^{12}$ independently of one another represent H; $C_{1-6}$-alkyl, in each case saturated or unsaturated, branched or unbranched, mono- or poly-substituted or unsubstituted; heterocyclyl or $C_{3-8}$-cycloalkyl, in each case saturated or unsaturated, mono- or poly-substituted or unsubstituted; $C(=O)R^{20}$; $SO_2R^{13}$; or aryl, $C_{3-8}$-cycloalkyl, heterocyclyl or heteroaryl bonded via $C_{1-3}$-alkyl and in each case mono- or poly-substituted or unsubstituted, wherein the alkyl chain in each case can be saturated or unsaturated, branched or unbranched; or $R^{11}$ and $R^{12}$ together represent $CH_2CH_2OCH_2CH_2$, $CH_2CH_2CH_2NR^{14}CH_2CH_2$ or $(CH_2)_{3-6}$, wherein $R^{14}$ denotes H; $C_{1-6}$-alkyl, in each case saturated or unsaturated, branched or unbranched, mono- or poly-substituted or unsubstituted; $C_{3-8}$-cycloalkyl, in each case saturated or unsaturated, mono- or poly-substituted or unsubstituted; aryl or heteroaryl, in each case mono- or poly-substituted or unsubstituted; $C(=O)R^{13}$; or aryl, $C_{3-8}$-cycloalkyl or heteroaryl bonded via $C_{1-3}$-alkyl and in each case mono- or poly-substituted or unsubstituted;

$R^{13}$ denotes $C_{1-6}$-alkyl, saturated or unsaturated, branched or unbranched, unsubstituted or mono- or poly-substituted; aryl, heteroaryl or $C_{3-8}$-cycloalkyl, in each case unsubstituted or mono- or poly-substituted; or aryl, heteroaryl or $C_{3-8}$-cycloalkyl linked via a $C_{1-5}$-alkyl chain and in each case unsubstituted or mono- or poly-substituted, wherein the alkyl chain in each case can be saturated or unsaturated, branched or unbranched;

$R^{20}$ denotes $C_{1-6}$-alkyl, saturated or unsaturated, branched or unbranched, unsubstituted or mono- or poly-substituted; aryl, heteroaryl or $C_{3-8}$-cycloalkyl, in each case unsubstituted or mono- or poly-substituted; $NR^{21}R^{22}$; or aryl, heteroaryl or $C_{3-8}$-cycloalkyl linked via a $C_{1-5}$-alkyl chain and in each case unsubstituted or mono- or poly-substituted, wherein the alkyl chain in each case can be saturated or unsaturated, branched or unbranched; wherein $R^{21}$ and $R^{22}$ independently of one another denote $C_{1-6}$-alkyl, saturated or unsaturated, branched or unbranched, unsubstituted or mono- or poly-substituted; aryl, heteroaryl or $C_{3-8}$-cycloalkyl, in each case unsubstituted or mono- or poly-substituted; or aryl, heteroaryl or $C_{3-8}$-cycloalkyl linked via a $C_{1-5}$-alkyl chain and in each case unsubstituted or mono- or poly-substituted, wherein the alkyl chain in each case can be saturated or unsaturated, branched or unbranched, "alkyl substituted", "heterocyclyl substituted" and "cycloalkyl substituted" represents replacement of a hydrogen by F, Cl, Br, I, —CN, $NH_2$, NH—$C_{1-6}$-alkyl, NH—$C_{1-6}$-alkyl-OH, $C_{1-6}$-alkyl, N($C_{1-6}$-alkyl)$_2$, N($C_{1-6}$-alkyl-OH)$_2$, $NO_2$, SH, S—$C_{1-6}$-alkyl, S-benzyl, O—$C_{1-6}$-alkyl, OH, O—$C_{1-6}$-alkyl-OH, =O, O-benzyl, $C(=O)C_{1-6}$-alkyl, $CO_2H$, $CO_2$—$C_{1-6}$-alkyl, phenyl or benzyl, and "aryl substituted" and "heteroaryl substituted" represents replacement one or more times, e.g. two, three or four times, of one or more hydrogen atoms of the ring system by F, Cl, Br, I, CN, $NH_2$, NH—$C_{1-6}$-alkyl, NH—$C_{1-6}$-alkyl-OH, N($C_{1-6}$-alkyl)$_2$, N($C_{1-6}$-alkyl-OH)$_2$, $NO_2$, SH, S—$C_{1-6}$-alkyl, OH, O—$C_{1-6}$-alkyl, O—$C_{1-6}$alkyl-OH, $C(=O)$-aryl; $C(=O)C_{1-6}$-alkyl, $C(=O)NHC_{1-6}$-alkyl; $C(=O)$—N-morpholine; $C(=O)$-piperidine; $(C=O)$-pyrrolidine; $(C=O)$-piperazine; $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $SCF_3$, $CF_3$,

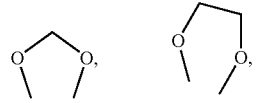

$C_{1-6}$-alkyl, pyrrolidinyl, piperidinyl, morpholinyl, benzyloxy, phenoxy, phenyl, pyridyl, alkylaryl, thienyl or furyl;

in the form of the racemate; of the enantiomers, diastereomers, mixtures of the enantiomers or diastereomers or of an individual enantiomer or diastereomer; of the bases and/or salts of physiologically acceptable acids.

Preference is given to substituted tetrahydropyrrolopyrazine compounds of formula I wherein $R^7$ represents $CH_2C(=O)R^8$, $(C=O)(CH_2)_mNR^{11}R^{12}$ or $C(=O)(CH_2)_n(C=O)R^8$, wherein m represents 1, 2 or 3, and n represents 1, 2, 3 or 4.

Preference also is given to substituted tetrahydropyrrolopyrazines of formula I wherein $R^1$, $R^2$ and $R^3$ independently of one another represent hydrogen or $C_{1-6}$-alkyl, branched or unbranched, in particular H.

Preference is further given to substituted tetrahydropyrrolopyrazines of formula I wherein $R^4$ and $R^5$ independently of one another represent H or $C_{1-6}$-alkyl, in particular H.

Preference is given also to tetrahydropyrrolopyrazines of formula I wherein $R^6$ denotes phenyl, thienyl, furyl, pyridyl or benzyl, unsubstituted or mono- or di-substituted by $OCH_3$, F, Cl, $CH_3$, isopropyl or

methyl or tert-butyl.

Preference is additionally given to substituted tetrahydropyrrolopyrazines of formula I wherein $R^7$ represents $CH_2CH_2C(=O)R^8$, $CH_2CH_2CH_2C(=O)R^8$ or $CH_2CH_2CH_2CH_2C(=O)R^8$, in particular $CH_2CH_2CH_2C(=O)R^8$.

Particular preference is given to substituted tetrahydropyrrolopyrazines of formula I wherein $R^7$ represents $C(=O)CH_2(C=O)R^8$, $C(=O)CH_2CH_2(C=O)R^8$, $C(=O)CH_2CH_2CH_2(C=O)R^8$, in particular $C(=O)CH_2CH_2(C=O)R^8$.

Preference is given also to tetrahydropyrrolopyrazines of formula I wherein $R^8$ represents $NR^9R^{10}$, $R^9$ represents H and $R^{10}$ denotes aryl, heteroaryl, heterocyclyl or $C_{3-8}$-cycloalkyl optionally bonded via a $C_{1-3}$-alkyl chain and in each case unsubstituted or mono- or poly-substituted, wherein the alkyl chain in each case can be saturated or unsaturated, branched or unbranched; $C_{1-6}$-alkyl, saturated, unsubstituted, branched or unbranched, or $R^9$ and $R^{10}$ together represent $CH_2CH_2OCH_2CH_2$, $CH_2CH_2NR^{14}CH_2CH_2$, $CH_2CH_2CH_2CH_2$ or $CH_2CH_2CH_2CH_2CH_2$, wherein $R^{14}$ denotes H; benzyl or phenyl, in each case unsubstituted or mono- or poly-substituted; $C(=O)R^{13}$.

Particular preference is given to substituted tetrahydropyrrolopyrazines of formula I wherein $R^8$ represents $NR^9R^{10}$, $R^9$ represents H and $R^{10}$ denotes phenyl, benzyl, phenethyl, methylthienyl, methylfuryl, methylpyridyl, ethylthienyl, ethylfuryl or ethylpyridyl, in each case mono- or poly-substituted; piperidyl, pyrrolidinyl, methylpiperidyl, methylpyrrolidinyl, ethylpiperidyl or ethylpyrrolidinyl, in each case mono- or poly-substituted; cyclopropyl, cyclobutyl, cyclopentyl or cyclohexyl; propyl, butyl or pentyl, or $R^9$ and $R^{10}$ together represent $CH_2CH_2OCH_2CH_2$, $CH_2CH_2NR^{14}CH_2CH_2$, $CH_2CH_2CH_2CH_2$ or $CH_2CH_2CH_2CH_2CH_2$, wherein $R^{14}$ denotes H; benzyl or phenyl, in each case unsubstituted or mono- or poly-substituted; $C(=O)CH_3$.

Preference is given also to substituted tetrahydropyrrolopyrazine derivatives of formula I wherein $R^7$ denotes $(C=O)CH_2NR^{11}R^{12}$, $(C=O)CH_2CH_2NR^{11}R^{12}$ or $(C=O)CH_2CH_2CH_2NR^{11}R^{12}$, and $R^{11}$ denotes $C(=O)R^{20}$ and $R^{12}$ denotes H; $C_{1-6}$-alkyl, branched or unbranched; $C_{3-8}$-cycloalkyl, in particular H; methyl, ethyl, propyl, butyl or cyclopropyl, wherein $R^{20}$ represents $NR^{21}R^{22}$; phenyl, furyl, benzyl, phenethyl, propylphenyl or cyclopropyl, in each case unsubstituted or mono- or poly-substituted; methyl, ethyl, propyl or butyl, in particular $NR^{21}R^{22}$; phenyl, benzyl, phenethyl or propylphenyl, in each case unsubstituted or mono- or poly-substituted by $CF_3$, or $CH_3$; cyclopropyl, unsubstituted or substituted by phenyl; or furyl, wherein $R^{21}$ and $R^{22}$ preferably independently of one another represent H or $C_{1-6}$-alkyl, preferably H, $CH_3$, tert-butyl or isopropyl.

Very particular preference is given to tetrahydropyrrolopyrazine compounds selected from the group consisting of:

1   4-[1-(4-chloro-phenyl)-3,4-dihydro-1H-pyrrolo[1,2-a]pyrazin-2-yl]-4-oxo-N-(3-trifluoromethyl-benzyl)-butyramide
2   4-oxo-4-(1-phenyl-3,4-dihydro-1H-pyrrolo[1,2-a]pyrazin-2-yl)-N-(3-trifluoromethyl-benzyl)-butyramide
3   N-sec-butyl-2-[1-(2-methoxy-phenyl)-3,4-dihydro-1H-pyrrolo[1,2-a]pyrazin-2-yl]-acetamide
4   N-cyclopropyl-3-[1-(3-fluoro-phenyl)-3,4-dihydro-1H-pyrrolo[1,2-a]pyrazin-2-yl]-3-oxo-propionamide
5   4-oxo-4-(1-m-tolyl-3,4-dihydro-1H-pyrrolo[1,2-a]pyrazin-2-yl)-N-(3-trifluoromethyl-benzyl)-butyramide
6   3-{2-[1-(2-chloro-phenyl)-3,4-dihydro-1H-pyrrolo[1,2-a]pyrazin-2-yl]-2-oxo-ethyl}-1,1-dimethyl-urea
7   4-[1-(4-fluoro-phenyl)-3,4-dihydro-1H-pyrrolo[1,2-a]pyrazin-2-yl]-N-isobutyl-4-oxo-butyramide
8   2-[1-(2,3-dihydro-benzo[1,4]dioxin-6-yl)-3,4-dihydro-1H-pyrrolo[1,2-a]pyrazin-2-yl]-N-(3-trifluoromethyl-benzyl)-acetamide
9   2-[1-(2,3-dihydro-benzo[1,4]dioxin-6-yl)-3,4-dihydro-1H-pyrrolo[1,2-a]pyrazin-2-yl]-N-p-tolyl-acetamide
10  3-tert-butyl-1-[2-[1-(2,4-difluoro-phenyl)-3,4-dihydro-1H-pyrrolo[1,2-a]pyrazin-2-yl]-2-oxo-ethyl]-1-isopropyl-urea
11  2-[1-(2,3-dihydro-benzo[1,4]dioxin-6-yl)-3,4-dihydro-1H-pyrrolo[1,2-a]pyrazin-2-yl]-N-isopropyl-acetamide
12 3-tert-butyl-1-isopropyl-1-[2-oxo-2-(1-m-tolyl-3,4-dihydro-1H-pyrrolo[1,2-a]pyrazin-2-yl)-ethyl]-urea
13  N-cyclopropyl-N-[2-(1-furan-3-yl-3,4-dihydro-1H-pyrrolo[1,2-a]pyrazin-2-yl)-2-oxo-ethyl]-4-methyl-benzamide
14  cyclopropanecarboxylic acid {2-[1-(3,4-dichloro-phenyl)-3,4-dihydro-1H-pyrrolo[1,2-a]pyrazin-2-yl]-2-oxo-ethyl}-isopropyl-amide
15  1-cyclopropyl-1-{2-[1-(2,4-difluoro-phenyl)-3,4-dihydro-1H-pyrrolo[1,2-a]pyrazin-2-yl]-2-oxo-ethyl}-3-isopropyl-urea
16 1-(4-acetyl-piperazin-1-yl)-2-[1-(2,4-difluoro-phenyl)-3,4-dihydro-1H-pyrrolo[1,2-a]pyrazin-2-yl]-ethanone
17 furan-2-carboxylic acid cyclopropyl-{2-[4-(3,4-dichloro-phenyl)-3,4-dihydro-1H-pyrrolo[1,2-a]pyrazin-2-yl]-2-oxo-ethyl}-amide
18  N-tert-butyl-N-[2-oxo-2-(1-p-tolyl-3,4-dihydro-1H-pyrrolo[1,2-a]pyrazin-2-yl)-ethyl]-isobutyramide
19  N-cyclopropyl-N-{2-[1-(3,4-dichloro-phenyl)-3,4-dihydro-1H-pyrrolo[1,2-a]pyrazin-2-yl]-2-oxo-ethyl}-isobutyramide
20   2-(1-(3-methoxyphenyl)-3,4-dihydropyrrolo[1,2-a]pyrazin-2(1H)-yl)-N-(3-(trifluoromethyl)benzyl)acetamide
21  1-ethyl-3,3-dimethyl-1-[2-oxo-2-(1-phenyl-3,4-dihydro-1H-pyrrolo[1,2-a]pyrazin-2-yl)-ethyl]-urea
22  quinoline-8-sulfonic acid {2-[1-(2,4-difluoro-phenyl)-3,4-dihydro-1H-pyrrolo[1,2-a]pyrazin-2-yl]-2-oxo-ethyl}-ethyl-amide
23  N-cyclopropyl-2-(1-p-tolyl-3,4-dihydro-1H-pyrrolo[1,2-a]pyrazin-2-yl)-acetamide
24  cyclopropanecarboxylic acid tert-butyl-[2-oxo-2-(1-p-tolyl-3,4-dihydro-1H-pyrrolo[1,2-a]pyrazin-2-yl)-ethyl]-amide
25  furan-2-carboxylic acid tert-butyl-{2-[1-(3,4-dichloro-phenyl)-3,4-dihydro-1H-pyrrolo[1,2-a]pyrazin-2-yl]-2-oxo-ethyl}-amide
26   2-[1-(2-chloro-phenyl)-3,4-dihydro-1H-pyrrolo[1,2-a]pyrazin-2-yl]-1-piperidin-1-yl-ethanone
27 2-phenyl-cyclopropanecarboxylic acid ethyl-[2-oxo-2-(1-phenyl-3,4-dihydro-1H-pyrrolo[1,2-a]pyrazin-2-yl)-ethyl]amide
29  N-(4-fluoro-phenyl)-4-[1-(3-methoxy-phenyl)-3,4-dihydro-1H-pyrrolo[1,2-a]pyrazin-2-yl]-4-oxo-butyramide
30   N-ethyl-N-[2-oxo-2-(1-phenyl-3,4-dihydro-1H-pyrrolo[1,2-a]pyrazin-2-yl)-ethyl]-butyramide
31   N-(1,2-dimethyl-propyl)-2-(1-p-tolyl-3,4-dihydro-1H-pyrrolo[1,2-a]pyrazin-2-yl)-acetamide
32  N-sec-butyl-2-(1-p-tolyl-3,4-dihydro-1H-pyrrolo[1,2-a]pyrazin-2-yl)-acetamide
33  N-{2-[1-(3,4-dichloro-phenyl)-3,4-dihydro-1H-pyrrolo[1,2-a]pyrazin-2-yl]-2-oxo-ethyl}-N-ethyl-isobutyramide
34 4-[1-(3-methoxy-phenyl)-3,4-dihydro-1H-pyrrolo[1,2-a]pyrazin-2-yl]-4-oxo-N-pyridin-4-ylmethyl-butyramide 35 furan-2-carboxylic acid isopropyl-{2-[1-(4-isopropyl-phenyl)-3,4-dihydro-1H-pyrrolo[1,2-a]pyrazin-2-yl]-2-oxo-ethyl}-amide
36 1-[1-(3-methoxy-phenyl)-3,4-dihydro-1H-pyrrolo[1,2-a]pyrazin-2-yl]-3-morpholin-4-yl-propane-1,3-dione
37 2-(1-p-tolyl-3,4-dihydro-1H-pyrrolo[1,2-a]pyrazin-2-yl)-N-(3-trifluoromethyl-benzyl)-acetamide
38 N-pyridin-3-ylmethyl-2-(1-p-tolyl-3,4-dihydro-1H-pyrrolo[1,2-a]pyrazin-2-yl)-acetamide
39 2-[1-(2,4-difluoro-phenyl)-3,4-dihydro-1H-pyrrolo[1,2-a]pyrazin-2-yl]-N-furan-2-ylmethyl-acetamide
41 N-benzyl-2-(1-p-tolyl-3,4-dihydro-1H-pyrrolo[1,2-a]pyrazin-2-yl)-acetamide
42 N-(3,4-dimethyl-phenyl)-3-[1-(3-methoxy-phenyl)-3,4-dihydro-1H-pyrrolo[1,2-a]pyrazin-2-yl]-3-oxo-propionamide
43 4-[1-(3-chloro-phenyl)-3,4-dihydro-1H-pyrrolo[1,2-a]pyrazin-2-yl]-N-isopropyl-4-oxo-butyramide
44 N-(1-benzyl-piperidin-4-yl)-2-(1-p-tolyl-3,4-dihydro-1H-pyrrolo[1,2-a]pyrazin-2-yl)-acetamide
45 2-[1-(4-chloro-phenyl)-3,4-dihydro-1H-pyrrolo[1,2-a]pyrazin-2-yl]-1-[4-(2-chloro-phenyl)-piperazin-1-yl]-ethanone
46 N-(1-benzyl-piperidin-4-yl)-2-[1-(4-chloro-phenyl)-3,4-dihydro-1H-pyrrolo[1,2-a]pyrazin-2-yl]-acetamide
48 1-(4-benzo[1,3]dioxol-5-ylmethyl-piperazin-1-yl)-2-[1-(4-chloro-phenyl)-3,4-dihydro-1H-pyrrolo[1,2-a]pyrazin-2-yl]ethanone
49 N-phenethyl-2-(1-p-tolyl-3,4-dihydro-1H-pyrrolo[1,2-a]pyrazin-2-yl)-acetamide
50 2-[1-(3,4-dichloro-phenyl)-3,4-dihydro-1H-pyrrolo[1,2-a]pyrazin-2-yl]-N-(2-pyridin-2-yl-ethyl)-acetamide
51 1-(4-benzo[1,3]dioxol-5-ylmethyl-piperazin-1-yl)-2-(1-p-tolyl-3,4-dihydro-1H-pyrrolo[1,2-a]pyrazin-2-yl)-ethanone
52 2-[1-(3,4-dichloro-phenyl)-3,4-dihydro-1H-pyrrolo[1,2-a]pyrazin-2-yl]-N-pyridin-3-ylmethyl-acetamide
53 1-(4-benzo[1,3]dioxol-5-ylmethyl-piperazin-1-yl)-2-[1-(2-chloro-phenyl)-3,4-dihydro-1H-pyrrolo[1,2-a]pyrazin-2-yl]ethanone
54 1-(4-benzyl-piperazin-1-yl)-2-[1-(4-chloro-phenyl)-3,4-dihydro-1H-pyrrolo[1,2-a]pyrazin-2-yl]-ethanone
55 2-[1-(4-chloro-phenyl)-3,4-dihydro-1H-pyrrolo[1,2-a]pyrazin-2-yl]-N-phenethyl-acetamide
56 2-[1-(2-chloro-phenyl)-3,4-dihydro-1H-pyrrolo[1,2-a]pyrazin-2-yl]-N-phenethyl-acetamide
57 2-[1-(3,4-dichloro-phenyl)-3,4-dihydro-1H-pyrrolo[1,2-a]pyrazin-2-yl]-N-(4-fluoro-benzyl)-acetamide
58 1-(4-benzyl-piperazin-1-yl)-2-[1-(2-chloro-phenyl)-3,4-dihydro-1H-pyrrolo[1,2-a]pyrazin-2-yl]-ethanone
59 N-cyclohexyl-2-(1-p-tolyl-3,4-dihydro-1H-pyrrolo[1,2-a]pyrazin-2-yl)-acetamide
60 1-(4-benzyl-piperazin-1-yl)-2-(1-p-tolyl-3,4-dihydro-1H-pyrrolo[1,2-a]pyrazin-2-yl)-ethanone
61 2-[1-(4-chloro-phenyl)-3,4-dihydro-1H-pyrrolo[1,2-a]pyrazin-2-yl]-N-(1,2-dimethyl-propyl)-acetamide
62 N-(2-piperidin-1-yl-ethyl)-2-(1-p-tolyl-3,4-dihydro-1H-pyrrolo[1,2-a]pyrazin-2-yl)-acetamide
65 N-(4-fluoro-phenyl)-2-(1-p-tolyl-3,4-dihydro-1H-pyrrolo[1,2-a]pyrazin-2-yl)-acetamide
66 furan-2-carboxylic acid ethyl-[2-oxo-2-(1-p-tolyl-3,4-dihydro-1H-pyrrolo[1,2-a]pyrazin-2-yl)-ethyl]-amide
67 2-[1-(4-fluoro-phenyl)-3,4-dihydro-1H-pyrrolo[1,2-a]pyrazin-2-yl]-N-isopropyl-acetamide
68 2-[1-(3,4-dichloro-phenyl)-3,4-dihydro-1H-pyrrolo[1,2-a]pyrazin-2-yl]-N-isobutyl-acetamide
69 2-[1-(4-chloro-phenyl)-3,4-dihydro-1H-pyrrolo[1,2-a]pyrazin-2-yl]-N-(2-pyrrolidin-1-yl-ethyl)-acetamide
70 N-benzo[1,3]dioxol-5-ylmethyl-2-(1-p-tolyl-3,4-dihydro-1H-pyrrolo[1,2-a]pyrazin-2-yl)-acetamide
71 2-(1-(4-chlorophenyl)-3,4-dihydropyrrolo[1,2-a]pyrazin-2(1H)-yl)-N-(4-fluorobenzyl)acetamide
72 2-(1-(4-chlorophenyl)-3,4-dihydropyrrolo[1,2-a]pyrazin-2(1H)-yl)-N-(3-(trifluoromethyl)benzyl)acetamide
73 2-(1-(4-chlorophenyl)-3,4-dihydropyrrolo[1,2-a]pyrazin-2(1H)-yl)-1-(4-(4-methoxyphenyl)piperazin-1-yl)ethanone
74 N-(2,4-dichlorophenethyl)-2-(1-(3,4-dichlorophenyl)-3,4-dihydropyrrolo[1,2-a]pyrazin-2(1H)-yl)acetamide
75 1-(4-(3-chlorophenyl)piperazin-1-yl)-4-(1-m-tolyl-3,4-dihydropyrrolo[1,2-a]pyrazin-2(1H)-yl)butane-1,4-dione
76 4-oxo-4-(1-(thiophen-2-yl)-3,4-dihydropyrrolo[1,2-a]pyrazin-2(1H)-yl)-N-(3-(trifluoromethyl)benzyl)butanamide
77 4-oxo-4-(1-(pyridin-2-yl)-3,4-dihydropyrrolo[1,2-a]pyrazin-2(1H)-yl)-N-(3-(trifluoromethyl)benzyl)butanamide
78 4-(1-tert-butyl-3,4-dihydropyrrolo[1,2-a]pyrazin-2(1H)-yl)-4-oxo-N-(3-(trifluoromethyl)benzyl)butanamide
79 4-oxo-4-(1-(pyridin-4-yl)-3,4-dihydropyrrolo[1,2-a]pyrazin-2(1H)-yl)-N-(3-(trifluoromethyl)benzyl)butanamide
80 4-(1-benzyl-3,4-dihydropyrrolo[1,2-a]pyrazin-2(1H)-yl)-4-oxo-N-(1-(3-(trifluoromethyl)phenyl)ethyl)butanamide
81 4-oxo-4-(1-phenyl-3,4-dihydropyrrolo[1,2-a]pyrazin-2(1H)-yl)-N-(1-(3-(trifluoromethyl)phenyl)ethyl)butanamide
82 4-oxo-4-(1-(thiophen-2-yl)-3,4-dihydropyrrolo[1,2-a]pyrazin-2(1H)-yl)-N-(1-(3-(trifluoromethyl)phenyl)ethyl)butanamide
83 4-oxo-4-(1-phenyl-3,4-dihydropyrrolo[1,2-a]pyrazin-2(1H)-yl)-N-(thiophen-2-ylmethyl)butanamide
84 4-oxo-4-(1-phenyl-3,4-dihydropyrrolo[1,2-a]pyrazin-2(1H)-yl)-N-(1-(3-(pyridin-3-yl)phenyl)ethyl)butanamide
85 N-(4-fluorobenzyl)-4-(1-methyl-3,4-dihydropyrrolo[1,2-a]pyrazin-2(1H)-yl)-4-oxobutanamide
86 4-(1-methyl-3,4-dihydropyrrolo[1,2-a]pyrazin-2(1H)-yl-4-oxo-N-(3-(trifluoromethyl)benzyl)butanamide
87 N-(2-oxo-2-(1-phenyl-3,4-dihydropyrrolo[1,2-a]pyrazin-2(1H)-yl)ethyl)-3-(3-trifluoromethyl)phenyl)propanamide
88 N-(2-oxo-2-(1-phenyl-3,4-dihydropyrrolo[1,2-a]pyrazin-2(1H)-yl)ethyl)-4-phenylbutanamide
89 3-oxo-3-(1-phenyl-3,4-dihydropyrrolo[1,2-a]pyrazin-2(1H)-yl)-N-(3-(trifluoromethyl)benzyl)propanamide
90 3-oxo-3-(1-phenyl-3,4-dihydropyrrolo[1,2-a]pyrazin-2(1H)-yl)-N-(3-trifluoromethyl)phenyl)propanamide
91 2-(1-phenyl-3,4-dihydropyrrolo[1,2-a]pyrazin-2(1H)-yl)-N-(3-(trifluoromethyl)benzyl)acetamide
92 (E)-3-(2-fluorophenyl)-N-(2-oxo-2-(1-phenyl-3,4-dihydropyrrolo[1,2-a]pyrazin-2(1H)-yl)ethyl)acrylamide The substituted tetrahydropyrrolopyrazine compounds according to the invention and in each case the corresponding acids, bases, salts and solvates are suitable as pharmaceutical active compounds in pharmaceutical compositions. The present invention therefore also provides a pharmaceutical composition comprising at least one substituted tetrahydropyrrolopyrazine compound of formula I according to the invention, wherein $R^1$ through $R^7$ have the above-mentioned meanings, and optionally one or more pharmaceutically acceptable auxiliary substances.

These pharmaceutical compositions according to the invention are suitable for influencing KCNQ2/3 channels and exert an agonistic or antagonistic, in particular an agonistic, action. The pharmaceutical compositions according to the invention are preferably suitable for treatment of disorders or diseases which are at least partly mediated by KCNQ2/3 channels.

The pharmaceutical composition according to the invention is preferably suitable for treatment of one or more diseases chosen from the group consisting of pain, preferably pain chosen from the group consisting of acute pain, chronic pain, neuropathic pain, muscular pain and inflammatory pain, migraine; epilepsy, anxiety states and urinary incontinence. The pharmaceutical compositions according to the invention are particularly preferably suitable for treatment of pain, very particularly preferably chronic pain, neuropathic pain, inflammatory pain and muscular pain. The compounds according to the invention are further preferably suitable for treatment of epilepsy.

The present invention also provides the use of at least one substituted tetrahydropyrrolopyrazine compound according to the invention and optionally one or more pharmaceutically acceptable auxiliary substances for the treatment of disorders or diseases which are at least partly mediated by KCNQ2/3 channels.

Preference is given to the use of at least one substituted tetrahydropyrrolopyrazine compound according to the invention and optionally one or more pharmaceutically acceptable auxiliary substances for the treatment of pain, preferably pain chosen from the group consisting of acute pain, chronic pain, neuropathic pain, muscular pain and inflammatory pain; migraine; epilepsy, anxiety states and urinary incontinence. Particular preference is given to the use of at least one substituted tetrahydropyrrolopyrazine compound according to the invention and optionally one or more pharmaceutically acceptable auxiliary substances for the treatment of pain, very particularly preferably chronic pain, neuropathic pain, inflammatory pain and muscular pain. Particular preference is further given to the use of at least one substituted tetrahydropyrrolopyrazine compound according to the invention and optionally one or more pharmaceutically acceptable auxiliary substances for the treatment of epilepsy.

The activity against pain can be shown, for example, in the Bennett or Chung model described hereinbelow. The activity against epilepsy can be shown, for example, in the DBA/2 mouse model (De Sarro et al., Naunyn Schmiedeberg's Arch. Pharmacol. 2001, 363, 330-336).

The present invention also provides a process for the preparation of the substituted tetrahydropyrrolopyrazine compounds according to the invention. The chemicals and reaction components employed in the reactions described above are commercially obtainable or can in each case be prepared by conventional methods known to the person skilled in the art.

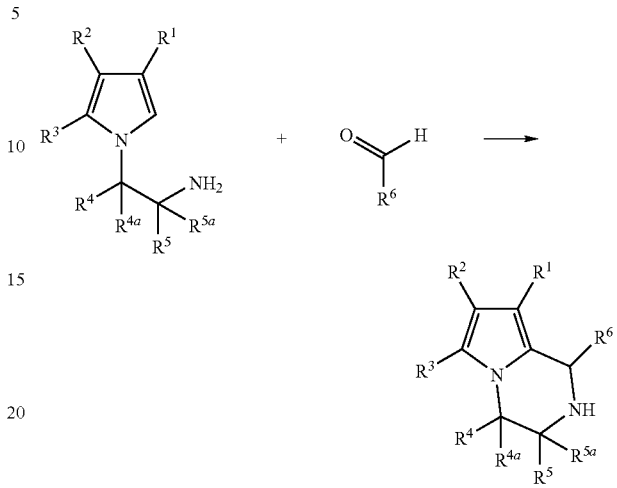

In this reaction a solution of the optionally substituted 2-(1H-pyrrol-1-yl)ethanamine and of the aldehyde of the formula $R^6C(=O)H$ a) in an organic acid, for example acetic acid, is stirred for 6-48 h at room temperature or b) in an alcohol, for example ethanol or methanol, with the addition of an organic acid, for example acetic acid or citric acid, is stirred at a temperature of 0-100° C., preferably 20° C. to 78° C., for 2-48 h
or c) in an organic solvent, for example toluene, benzene or DCM, is treated with benzotriazole and an acid, for example p-toluenesulfonic acid, and refluxed using a water separator.

After removal of the solvent, the residue can be taken up in an aqueous basic solution, for example sodium carbonate solution, sodium bicarbonate solution, potassium carbonate solution, sodium hydroxide solution or potassium hydroxide solution, and extracted with an organic solvent, for example DCM, chloroform, ethyl acetate or diethyl ether. Alternatively, the residue can be taken up in an organic solvent, for example ethyl acetate, DCM, chloroform or diethyl ether. The organic phase can be washed with an aqueous basic solution, for example sodium carbonate solution, sodium bicarbonate solution, potassium carbonate solution, sodium hydroxide solution or potassium hydroxide solution.

Preparation of tetrahydropyrrolopyrazines where $R^7=C(=O)(CH_2)_n(C=O)R^8$

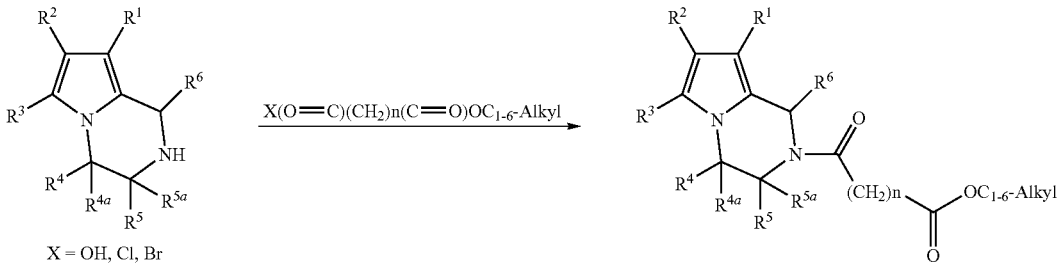

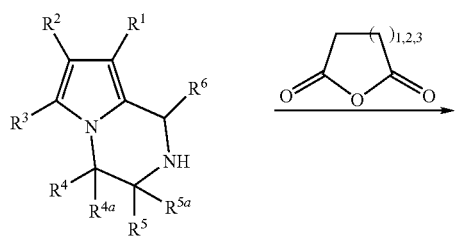
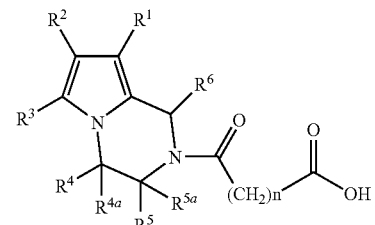

The corresponding tetrahydropyrrolopyrazine is reacted, with the addition of an organic base, for example triethylamine, diisopropylethylamine, diisopropylamine or pyridine, in an organic solvent, for example DCE or DCM, with an acid of the general formula HOOC(CH$_2$)$_n$(C=O)OC$_{1-6}$-alkyl, wherein C$_{1-6}$-alkyl in this case preferably represents ethyl, methyl or tert-butyl, at a temperature of 30-100° C., preferably 30-83° C., optionally using bases and optionally coupling reagents, in solvents, such as, for example, methanol, DMF or DCM. As bases there can be used, for example, sodium methanolate, TEA, DIEA or N-methylmorpholine. Suitable coupling reagents are, for example, EDCI, HOBt, DCC, CDI, HBTU, DMAP or pentafluorophenyldiphenyl phosphinate. The reaction time can vary between 1 h and 3 d. Acid chlorides or bromides of the general formula Cl(O=C)(CH$_2$)$_n$(C=O)C$_{1-6}$-alkyl and Br(O=C)(CH$_2$)$_n$(C=O)C$_{1-6}$-alkyl, respectively, can be reacted in solvents, such as, for example, DCM, benzene, toluene, THF, DMF, acetonitrile, pyridine, dioxane, water or 1-methyl-pyrrolidin-2-one, or mixtures of those solvents, using bases, for example pyridine, DIEA, TEA, N-methylmorpholine or sodium bicarbonate, optionally with addition of a coupling reagent, such as, for example, DCC.

The protective group C$_{1-6}$-alkyl can be removed with the aid of an acid, for example HCl, trifluoroacetic acid or p-toluenesulfonic acid, optionally in a suitable organic solvent, for example acetonitrile, diethyl ether, THF, DCM or toluene, at a temperature of −10-120° C. The use of aqueous inorganic bases, such as lithium hydroxide, potassium hydroxide, sodium hydroxide, sodium carbonate, sodium bicarbonate, potassium carbonate, in organic solvents, such as methanol, ethanol, dioxane, DCM, THF, diethyl ether, or in those solvents in the form of mixtures, is additionally possible.

The corresponding tetrahydropyrrolopyrazine can also be converted into the tetrahydropyrrolopyrazine acid derivative by reaction of the corresponding anhydride in solvents, such as, for example, DCM, chloroform, 1,2-dichloroethane, acetone, acetonitrile, dioxane, THF, DMF, diethyl ether, benzene, toluene, ethyl acetate, water, methanol, ethanol, propanol or i-propanol, by addition of bases, such as, for example, triethylamine, diethylamine, diisopropylethylamine, pyridine, NaH, optionally with the addition of 18-Crown-6, NaOH, KOH, sodium acetate, potassium acetate or potassium carbonate, or by addition of acids, such as, for example, sulfuric acid, optionally using coupling reagents, such as, for example, DMAP, DCC or DIC.

The tetrahydropyrrolopyrazine acid derivative prepared will be reacted, with the addition of a base, for example sodium methanolate, N-methylmorpholine, diisopropylamine, triethylamine or diisopropylethylamine, and of a coupling reagent, for example EDCI or CDI, DCC, HBTU, DMAP or pentafluorophenyldiphenyl phosphinate, and optionally hydroxybenzotriazole hydrate, with the corresponding amine NHR$^9$R$^{10}$ in an organic solvent, for example DMF, DCM or THF, at 0-100° C., preferably 20° C. to 69° C., to give compounds in which R$^7$ denotes C(=O)(CH$_2$)$_n$(C=O)NR$^9$R$^{10}$.

For the preparation of compounds in which R$^7$ denotes C(=O)(CH$_2$)$_n$(C=O)NH$_2$, the corresponding reaction is carried out with NH$_3$ in dioxane.

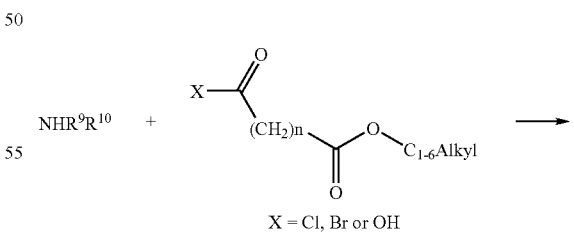

X = Cl, Br or OH

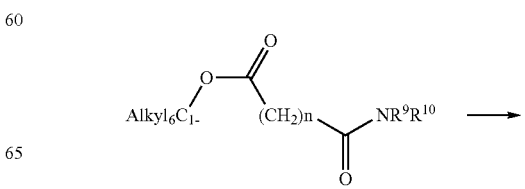

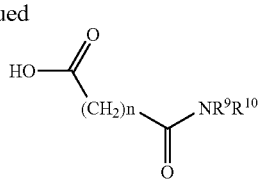

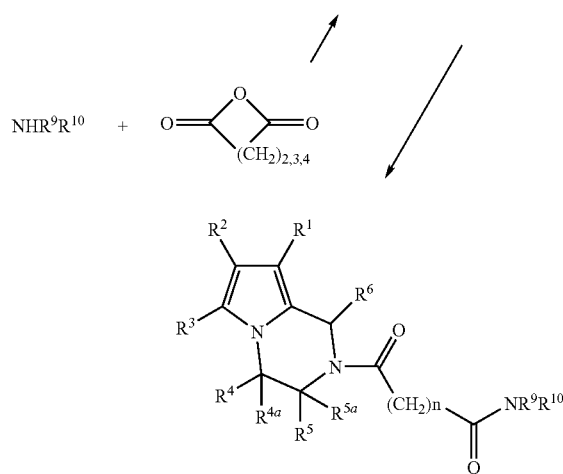

A further possibility consists in reacting the corresponding tetrahydropyrrolopyrazine with a structural unit of the formula HOOC(CH$_2$)$_n$(C=O)NR$^9$R$^{10}$. The mentioned structural unit is obtained by reaction of the corresponding amine of the formula NHR$^9$R$^{10}$ with a monoalkyldicarboxylic acid ester or a dicarboxylic acid alkyl ester chloride or bromide or by reaction with the corresponding carboxylic anhydride.

The reaction of the monoalkyldicarboxylic acid ester with the corresponding amine is carried out using bases and optionally coupling reagents in solvents such as, for example, methanol, DMF or DCM. As bases there can be used, for example, sodium methanolate, TEA, DIEA or N-methylmorpholine. Suitable coupling reagents are, for example, EDCI, HOBt, DCC, CDI, HBTU, DMAP or pentafluorophenyldiphenyl phosphinate. The reaction time can vary between 1 h and 3 d.

The dicarboxylic acid alkyl ester chlorides or bromides react in solvents such as, for example, DCM, benzene, toluene, THF, DMF, acetonitrile, pyridine, dioxane, water or 1-methyl-pyrrolidin-2-one, or mixtures of those solvents, using bases, for example pyridine, DIEA, TEA, N-methylmorpholine or sodium bicarbonate, optionally with the addition of a coupling reagent, such as, for example DCC.

The corresponding carboxylic anhydrides are converted into the corresponding structural units in solvents such as, for example, DCM, chloroform, 1,2-dichloroethane, acetone, acetonitrile, dioxane, THF, DMF, diethyl ether, benzene, toluene, ethyl acetate, water, methanol, ethanol, propanol or i-propanol, by addition of bases, such as, for example, triethylamine, diethylamine, diisopropylethylamine, pyridine, NaH, optionally with the addition of 18-Crown-6, NaOH, KOH, sodium acetate, potassium acetate or potassium carbonate, or by addition of acids, such as, for example, sulfuric acid, optionally using coupling reagents, such as, for example, DMAP, DCC or DIC.

The final coupling of the acid structural unit and the tetrahydropyrrolopyrazine is reacted to form the compounds with the addition of a base, for example sodium methanolate, N-methyl-morpholine, diisopropylamine, triethylamine or diisopropylethylamine, and optionally of a coupling reagent, EDCI, CDI, DCC, HBTU, DMAP or pentafluorophenyldiphenyl phosphinate, and optionally hydroxybenzotriazole hydrate, in an organic solvent, for example DMF, DCM or THF, at 0-100° C., preferably 20° C. to 69° C.

Preparation of tetrahydropyrrolopyrazines in which R$^7$ denotes (C=O)(CH$_2$)$_m$NR$^{11}$R$^{12}$

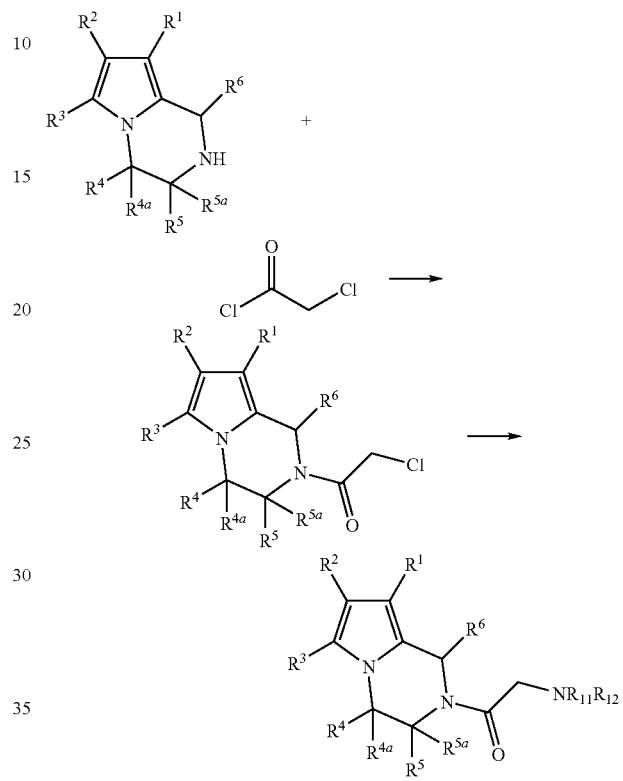

The tetrahydropyrrolopyrazine is reacted, with the addition of an organic base, for example triethylamine, diisopropylethylamine, diisopropylamine or pyridine, with chloroacetic acid chloride at a temperature of 40-100° C., preferably 40-83° C. The product formed is reacted with a primary or secondary amine in a reaction medium, preferably chosen from the group consisting of ethanol, n-butanol, toluene or chloroform, optionally with the addition of a basic salt, preferably Na$_2$CO$_3$ or K$_2$CO$_3$, optionally with the addition of an alkali metal halide, preferably potassium iodide or sodium iodide, optionally with the addition of a base, preferably chosen from the group consisting of triethylamine, diisopropylethylamine and 4-dimethylamino-pyridine, particularly preferably triethylamine, at temperatures of 0-160° C., preferably 20-120° C.

Acylation of the Monoalkylated Amines

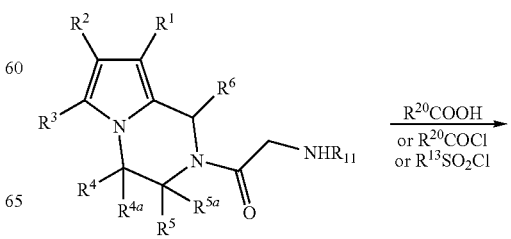

-continued

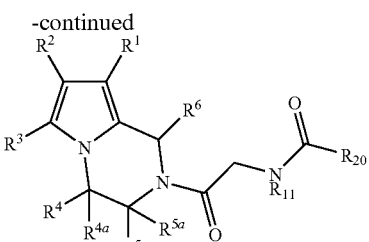

or

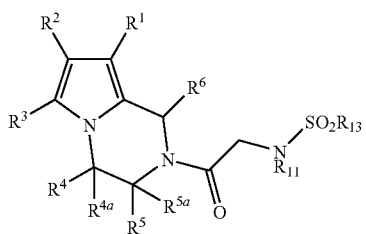

At room temperature, the acid of the formula R$^{20}$COOH, with the addition of a base, for example diisopropylamine, triethylamine or diisopropylethylamine, and of a coupling reagent, for example EDCI or CDI, and optionally hydroxybenzotriazole hydrate, is reacted with the corresponding tetrahydropyrrolopyrazine in an organic solvent, for example DCM or THF, at 0-100° C., preferably 20° C. to 69° C.

Alternatively, a tetrahydropyrrolopyrazine, with the addition of a base, for example triethylamine, diisopropylethylamine or diisopropylamine, in an organic solvent, for example DCE or DCM, is reacted with an acid chloride of the formula R$^{20}$(CO)Cl or R$^{13}$SO$_2$Cl at a temperature of 0-100° C., preferably 20° C. to 80° C.

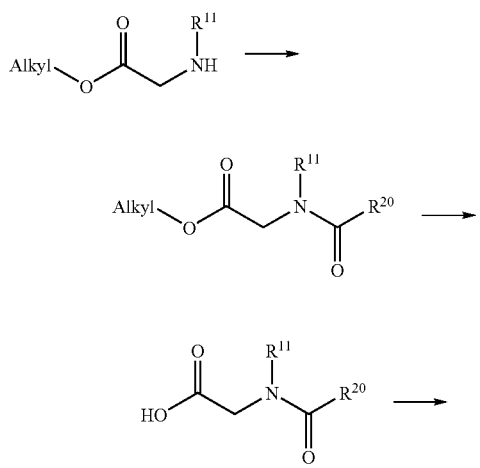

The products in which R$^{12}$=C(O)R$^{20}$ can likewise be obtained by reaction of the tetrahydropyrrolopyrazine with a glycine derivative. The glycine derivative is obtained by reacting the glycine alkyl ester with the corresponding acid of the formula R$^{20}$(CO)OH using bases and optionally coupling reagents in solvents, such as, for example, methanol, DMF or DCM. As bases there can be used, for example, sodium methanolate, TEA, DIEA or N-methyl-morpholine. Suitable coupling reagents are, for example, EDCI, HOBt, DCC, CDI, HBTU, DMAP or pentafluorophenyldiphenyl phosphinate. The reaction time can vary between 1 h and 3 d.

The glycine alkyl ester can also be reacted with the corresponding acid chloride or bromide of the formula R$^{20}$(CO)Cl or R$^{20}$(CO)Br, respectively. The carboxylic acid chlorides or bromides react in solvents such as, for example, DCM, benzene, toluene, THF, DMF, acetonitrile, pyridine, dioxane, water or 1-methyl-pyrrolidin-2-one, or mixtures of those solvents, using bases, for example pyridine, DIEA, TEA, N-methylmorpholine or sodium bicarbonate, optionally with the addition of a coupling reagent, such as, for example, DCC.

The alkyl ester is hydrolyzed with the aid of an acid, for example HCl, trifluoroacetic acid or p-toluenesulfonic acid, optionally in a suitable organic solvent, for example acetonitrile, diethyl ether, THF, DCM or toluene, at a temperature of −10-120° C. The use of aqueous inorganic bases, such as lithium hydroxide, potassium hydroxide, sodium hydroxide, sodium carbonate, sodium bicarbonate, potassium carbonate, in organic solvents, such as methanol, ethanol, dioxane, DCM, THF, diethyl ether, or in those solvents in the form of mixtures, is likewise possible.

The coupling of the glycine derivative to the corresponding tetrahydropyrrolopyrazine is carried out using bases and optionally coupling reagents in solvents, such as, for example, methanol, DMF or DCM. As bases there can be used, for example, sodium methanolate, TEA, DIEA or N-methylmorpholine. Suitable coupling reagents are, for example, EDCI, HOBt, DCC, CDI, HBTU, DMAP or pentafluorophenyldiphenyl phosphinate. The reaction time can vary between 1 h and 3 d.

Ureas of the Monoalkylated Amines

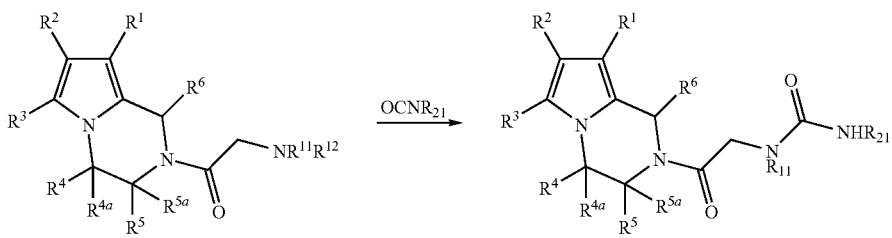

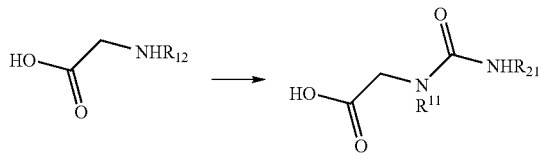

The corresponding tetrahydropyrrolopyrazine ($R^{11}$=H) is reacted in an organic solvent, for example DCE, DCM, chloroform, benzene, toluene, ethanol, acetone, diethyl ether, petroleum ether, dioxane or THF, with an isocyanate of the formula $OCNR^{21}$ at a temperature of from 20° C. to 110° C. to give compounds in which $R^7$ denotes $C(=O)CH_2NR^{11}(C=O)NHR^{21}$. The same products are obtained by reaction of the corresponding tetrahydropyrrolopyrazine with a functionalised glycine structural unit. The glycine structural unit is obtained by reacting glycine or N-alkylglycine with isocyanates of the formula $OCNR^{21}$ in solvents such as dioxane, water, acetone, diethyl ether or acetonitrile, or mixtures of those solvents, with the addition of a base, such as, for example, triethylamine, NaOH, KOH or $K_2CO_3$.

The coupling of the two structural units is carried out with the addition of a base, for example sodium methanolate, N-methylmorpholine, diisopropylamine, triethylamine or diisopropylethylamine, and optionally of a coupling reagent, such as, for example, EDCI, CDI, DCC, HBTU, DMAP or pentafluorophenyldiphenyl phosphinate, and optionally hydroxybenzotriazole hydrate, in an organic solvent, for example DMF, DCM or THF, at 0-100° C., preferably 20° C. to 69° C.

Preparation of tetrahydropyrrolopyrazines in which $R^7$ denotes $CH_2C(=O)R^8$

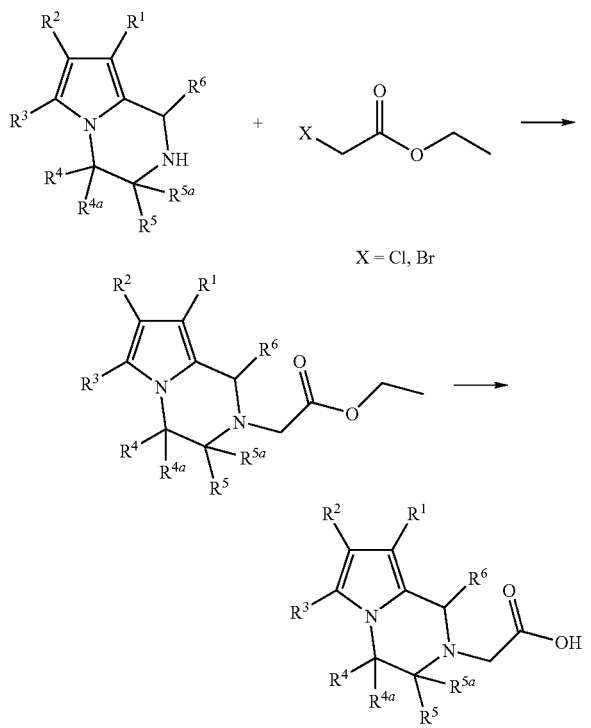

The tetrahydropyrrolopyrazine is reacted, in an organic solvent, for example acetonitrile, benzene, toluene, ethanol, DMF, THF or dioxane, with the addition of a base, for example potassium carbonate, NaOH, KOH, sodium amide, sodium ethanolate, potassium tert-butylate, sodium amide, sodium hydride, triethylamine or diisopropylethylamine, with ethyl bromoacetate at 20° C. to 160° C. The ester can be split off with the aid of an acid, for example HCl, trifluoroacetic acid or p-toluenesulfonic acid, optionally in a suitable organic solvent, for example acetonitrile, diethyl ether, THF, DCM or toluene, at a temperature of −10-120° C.

The use of aqueous inorganic bases, such as lithium hydroxide, potassium hydroxide, sodium hydroxide, sodium carbonate, sodium bicarbonate, potassium carbonate, in organic solvents, such as methanol, dioxane, DCM, THF, diethyl ether, or in those solvents in the form of mixtures, is additionally possible.

Preparation of tetrahydropyrrolopyrazines in which $R^7$ denotes $CH_2(C=O)NR^9R^{10}$

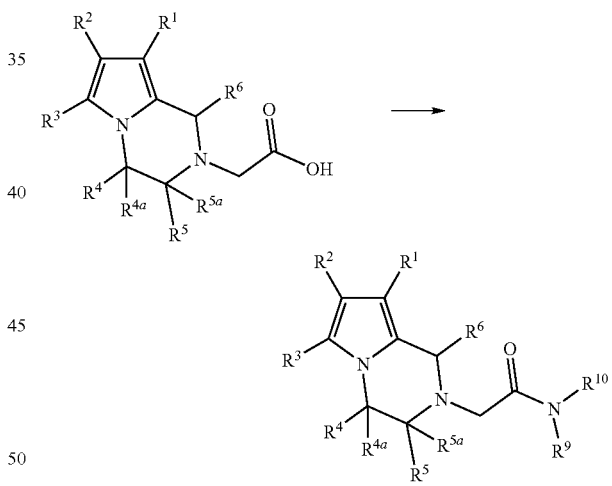

The tetrahydropyrrolopyrazine acid derivative can be reacted, with the addition of a base, for example diisopropylamine, triethylamine or diisopropylethylamine, and of a coupling reagent, for example EDCI or CDI, and optionally hydroxybenzotriazole hydrate, with the corresponding amine $NHR^9R^{10}$ in an organic solvent, for example DCM or THF, at 0-100° C., preferably 20° C. to 69° C., to give compounds in which $R^7$ denotes $CH_2(C=O)NR^9R^{10}$. For the preparation of compounds in which $R^7$ denotes $CH_2(C=O)NH_2$, the corresponding reaction is carried out with $NH_3$ in dioxane.

The reactions described above can furthermore in each case be carried out under conventional conditions familiar to the person skilled in the art, for example in respect of pressure, temperature, inert gas atmosphere or sequence of addition of the components. The optimum process procedure under the particular conditions can optionally be determined by the person skilled in the art by simple preliminary experiments.

All the process steps described above and in each case also the purification and/or isolation of intermediate or end products can be carried out in part or entirely under an inert gas atmosphere, preferably under a nitrogen atmosphere or argon atmosphere.

The substituted tetrahydropyrrolopyrazine compounds according to the invention can be isolated both in the form of their free bases, their free acids and also in each case in the form of corresponding salts, in particular physiologically acceptable salts.

The free bases of the particular substituted tetrahydropyrrolopyrazine compounds according to the invention can be converted, for example by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, maleic acid, malic acid, succinic acid, tartaric acid, mandelic acid, fumaric acid, lactic acid, citric acid, glutamic acid or aspartic acid, into the corresponding salts, preferably physiologically acceptable salts.

The free bases of the particular substituted tetrahydropyrrolopyrazine compounds according to the invention can likewise be converted with the free acid or a salt of a sugar substitute, such as e.g. saccharin, cyclamate or acesulfame, into the corresponding physiologically acceptable salts.

Correspondingly, the free acids of the substituted tetrahydropyrrolopyrazine compounds according to the invention can be converted by reaction with a suitable base into the corresponding physiologically acceptable salts. Examples which may be mentioned are the alkali metal salts, alkaline earth metal salts or ammonium salts $[NH_xR_{4-x}]^+$, wherein x=0, 1, 2, 3 or 4, and R represents linear or branched $C_{1-4}$-alkyl.

The substituted tetrahydropyrrolopyrazine compounds according to the invention can optionally, like the corresponding acids, the corresponding bases or salts of these compounds, also be obtained in the form of their solvates, preferably in the form of their hydrates, by conventional methods known to the person skilled in the art.

If the substituted tetrahydropyrrolopyrazine compounds according to the invention are obtained in the form of a mixture of their stereoisomers, preferably in the form of their racemates or other mixtures of their various enantiomers and/or diastereomers, after their preparation, these can be separated by conventional processes known to the person skilled in the art and optionally isolated. Examples which may be mentioned include chromatographic separation processes, in particular liquid chromatography processes under normal pressure or under elevated pressure, preferably MPLC and HPLC processes, and processes of fractional crystallization. In this context, in particular, individual enantiomers, e.g. diastereomeric salts formed by means of HPLC on a chiral stationary phase or by means of crystallization with chiral acids, for example (+)-tartaric acid, (−)-tartaric acid or (+)-10-camphorsulfonic acid, can be separated from one another.

The pharmaceutical composition according to the invention can be in a liquid, semi-solid or solid medicament form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, optionally pressed to tablets, filled into capsules or suspended in a liquid, and can also be administered as such. In addition to at least one substituted tetrahydropyrrolopyrazine compound according to the invention, the pharmaceutical composition according to the invention conventionally comprises further physiologically acceptable pharmaceutical auxiliary substances, which can preferably be chosen from the group consisting of carrier materials, fillers, solvents, diluents, surface-active substances, dyestuffs, preservatives, disintegrating agents, slip agents, lubricants, aromas and binders.

The choice of the physiologically acceptable auxiliary substances and the amounts thereof to be employed depends on whether the pharmaceutical composition is to be administered orally, subcutaneously, parenterally, intravenously, intraperitoneally, intradermally, intramuscularly, intranasally, buccally, rectally or locally, for example on infections on the skin, the mucous membranes and on the eyes. Formulations in the form of tablets, coated tablets, capsules, granules, pellets, drops, juices and syrups are preferably suitable for oral administration, and solutions, suspensions, easily reconstitutable dry formulations and sprays are suitable for parenteral, topical and inhalatory administration. The substituted tetrahydropyrrolopyrazine compounds employed in the pharmaceutical composition according to the invention can be in a depot, in dissolved form or in a plaster, optionally with addition of agents which promote penetration through the skin, as suitable formulations for percutaneous administration. Formulation forms which can be used orally or percutaneously can also release the particular substituted tetrahydropyrrolopyrazine compound according to the invention in a delayed manner. The preparation of the pharmaceutical compositions according to the invention is carried out with the aid of conventional means, devices, methods and processes known from the prior art, such as are described, for example, in "Remingtons Pharmaceutical Sciences", editor A. R. Gennaro, 17th edition, Mack Publishing Company, Easton, Pa., 1985, in particular in part 8, chapter 76 to 93. The corresponding description is incorporated herein by reference and forms part of the disclosure.

The amount of the particular substituted tetrahydropyrrolopyrazine compound according to the invention to be administered to the patient can vary and depends, for example, on the weight or age of the patient and on the mode of administration, the indication and the severity of the disease. From 0.005 to 100 mg/kg, preferably from 0.05 to 75 mg/kg of body weight of the patient of at least one such compound according to the invention are conventionally administered.

The invention is explained in further detail hereinafter with reference to illustrative examples. These examples are merely illustrative and do not limit the overall inventive concept. In the examples, $R^{4a}$, $R^{5a}$ and $R^{6a}$ in each case denote H.

EXAMPLES

Synthesis of 2-(1H-pyrrol-1-yl)ethanamine

NaOH (9.4 g; 0.23 mol) and tetrabutylammonium hydrogen sulfate (0.8 g; 2.36 mmol) were added to a solution of pyrrole (0.06 mol) in acetonitrile (33 ml) and the mixture was stirred for 30 minutes at room temperature. After addition of 2-chloroethylamine hydrochloride (8.2 g; 0.07 mol), the mixture was heated under reflux for 24 h. After cooling, the insoluble inorganic residue was filtered out, and the solvent was removed under reduced pressure. The crude product was obtained, which was used for further reactions without further purification.

Synthesis of the 1-aryl-1,2,3,4-tetrahydropyrrolo[1,2-a]pyrazines

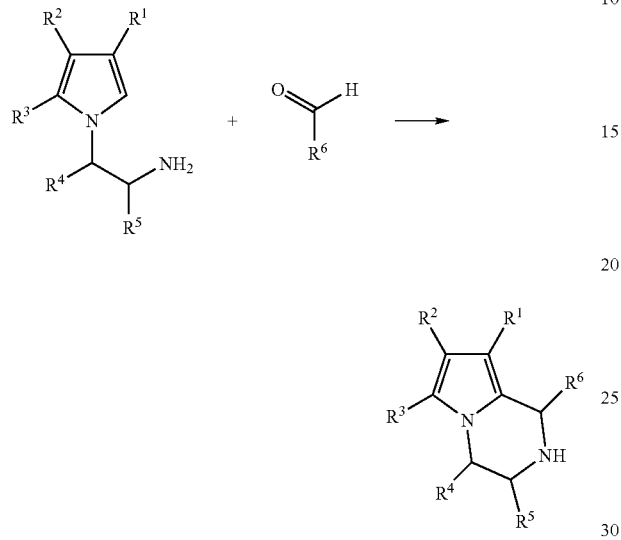

Method A

A solution of 2-(1H-pyrrol-1-ypethanamine (0.1 mol) and the corresponding aldehyde (0.1 mol) in acetic acid (250 ml) was stirred for 48 h at room temperature. When the reaction had ended, the solvent was removed on a rotary evaporator and the residue was taken up in aqueous sodium carbonate solution (10%) and extracted with DCM. The organic phase was then dried over MgSO$_4$ and concentrated in vacuo. Purification was carried out by column chromatography on neutral Al$_2$O$_3$ or by washing with 2-propanol or by crystallization with 2-propanol/n-hexane.

Method B

Acetic acid (0.3 ml) was added to a solution of 2-(1H-pyrrol-1-yl)ethanamine (0.05 mol) and the corresponding aldehyde (0.05 mol) in ethanol (25 ml) and the mixture was heated under reflux for 10 min. It was then subsequently stirred for a further 1 h at room temperature. The reaction mixture was concentrated on a rotary evaporator and the residue was taken up in ethyl acetate. The organic phase was washed with NaHCO$_3$ solution, dried over MgSO$_4$ and concentrated. Purification was carried out by column chromatography over neutral Al$_2$O$_3$.

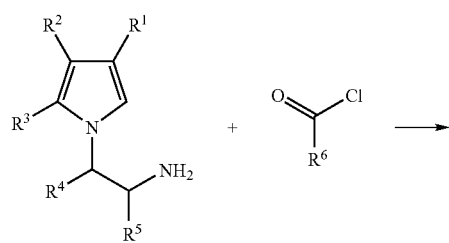

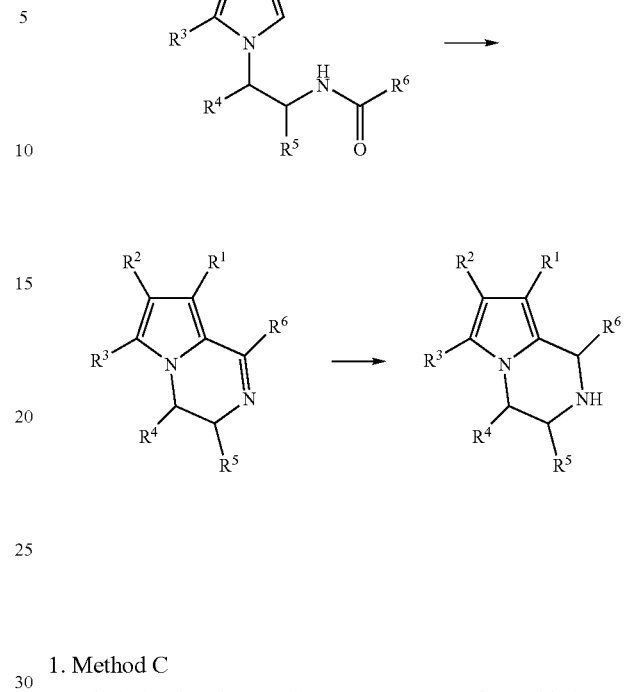

1. Method C

Triethylamine (19.5 ml, 140 mmol) was first added to a solution of 2-(1H-pyrrol-1-yl)ethanamine (8.5 g, 77.2 mmol) in DCM (250 ml), and the mixture was cooled to 0° C. The corresponding acid chloride (84.9 mmol) was then added, and stirring was carried out overnight at room temperature. The reaction mixture was concentrated to dryness under reduced pressure. The residue was taken up in DCM (150 ml), washed with aqueous NaOH solution (1 M, 150 ml) and concentrated to dryness. The resulting amide was purified by column chromatography over silica gel (mobile phase DCM/MeOH, 95:5).

The corresponding amide (50.7 mmol) was added to POCl$_3$ (50 ml) at room temperature, and the mixture was heated for 2 h under reflux. After cooling to room temperature, concentration to dryness was carried out and the resulting residue was taken up in DCM (300 ml) and washed with aqueous NH$_4$OH solution (10%, 300 ml). The organic phase was dried over sodium sulfate and then concentrated to dryness. Purification of the imine formed was carried out by column chromatography over silica gel (mobile phase: DCM/7 M NH$_3$ in MeOH, 95:5).

NaBH$_4$ (2.57 g, 67.8 mmol) was added slowly to a solution of the imine (22.6 mmol) in MeOH/water (10:1, 150 ml), and the mixture was stirred overnight at room temperature. Because the reaction was still incomplete (TLC control), further NaBH$_4$ (0.86 g, 22.6 mmol) was added and stirring was again carried out overnight. The reaction mixture was then concentrated and the residue was taken up in NH$_4$OH (10%, 450 ml) and extracted with DCM (450 ml). The organic phase was dried over sodium sulfate and concentrated. The crude product was purified by column chromatography over silica gel (mobile phase: DCM/7 M NH$_3$ in MeOH, 98:2).

The following tetrahydropyrrolopyrazines were used for synthesis of the compounds in the examples:

| No. | Name | Structure | Method |
|-----|------|-----------|--------|
| A1 | 1-(3-methoxyphenyl)-1,2,3,4-tetrahydropyrrolo[1,2-a]pyrazine | 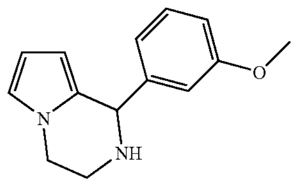 | B |
| A2 | 1-phenyl-1,2,3,4-tetrahydropyrrolo[1,2-a]pyrazine | 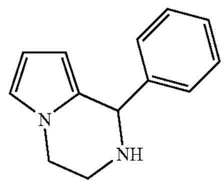 | A |
| A3 | 1-(thiophen-2-yl)-1,2,3,4-tetrahydropyrrolo[1,2-a]pyrazine | 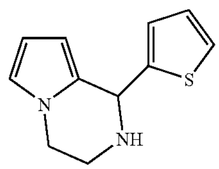 | B |
| A4 | 1-(3-fluorophenyl)-1,2,3,4-tetrahydropyrrolo[1,2-a]pyrazine | 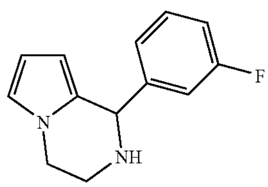 | B |
| A5 | 1-benzyl-1,2,3,4-tetrahydropyrrole-[1,2-a]pyrazine | 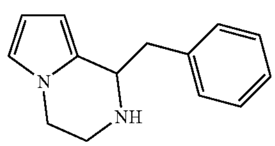 | B |
| A6 | 1-p-tolyl-1,2,3,4-tetrahydropyrrole-[1,2-a]pyrazine | 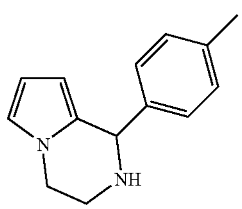 | A |
| A7 | 1-(4-chlorophenyl)-1,2,3,4-tetrahydropyrrolo[1,2-a]pyrazine | 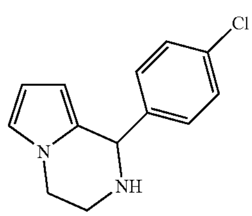 | A |
| A8 | 1-(4-fluorophenyl)-1,2,3,4-tetrahydropyrrolo[1,2-a]pyrazine | 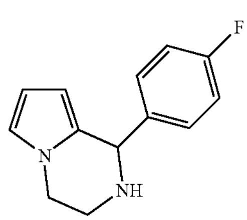 | A |

-continued

| No. | Name | Structure | Method |
|-----|------|-----------|--------|
| A9  | 1-(2,4-difluorophenyl)-1,2,3,4-tetrahydropyrrolo[1,2-a]pyrazine | 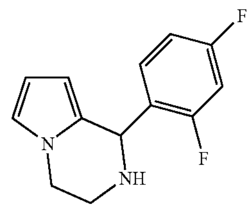 | A |
| A10 | 1-(2-fluorophenyl)-1,2,3,4-tetrahydropyrrolo[1,2-a]pyrazine | 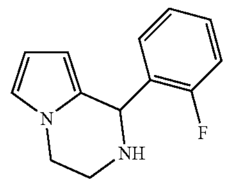 | A |
| A11 | 1-(3,4-dichlorophenyl)-1,2,3,4-tetrahydropyrrolo[1,2-a]pyrazine | 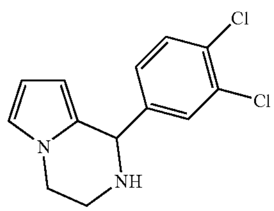 | A |
| A12 | 1-(2-chlorophenyl)-1,2,3,4-tetrahydropyrrolo[1,2-a]pyrazine | 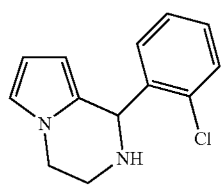 | A |
| A13 | 1-(2-methoxyphenyl)-1,2,3,4-tetrahydropyrrolo[1,2-a]pyrazine | 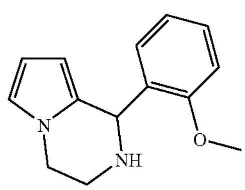 | A |
| A14 | 1-m-tolyl-1,2,3,4-tetrahydropyrrole-[1,2-a]pyrazine | 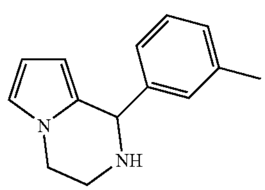 | A |
| A15 | 1-(furan-3-yl)-1,2,3,4-tetrahydro-pyrrolo[1,2-a]pyrazine | 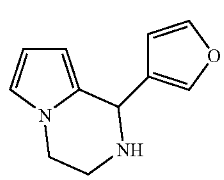 | A |
| A16 | 1-(2,3-dihydrobenzo[b][1,4]dioxin-6-yl)-1,2,3,4-tetrahydropyrrolo[1,2-a]pyrazine | 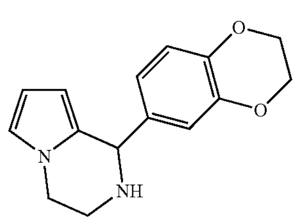 | A |

-continued

| No. | Name | Structure | Method |
|-----|------|-----------|--------|
| A17 | 1-(3-chlorophenyl)-1,2,3,4-tetrahydropyrrolo[1,2-a]pyrazine | 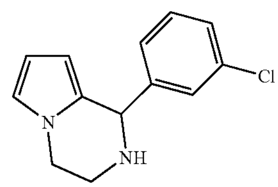 | A |
| A18 | 1-(4-isopropylphenyl)-1,2,3,4-tetrahydropyrrolo[1,2-a]pyrazine | 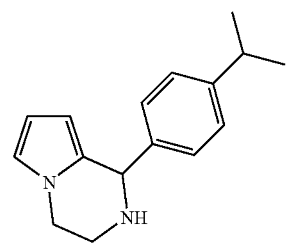 | A |
| A19 | 1-(pyridin-2-yl)-1,2,3,4-tetrahydropyrrolo[1,2-a]pyrazine | 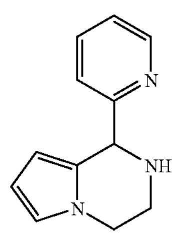 | B |
| A20 | 1-(pyridin-4-yl)-1,2,3,4-tetrahydropyrrolo[1,2-a]pyrazine | 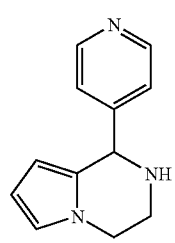 | C |
| A21 | 1-methyl-1,2,3,4-tetrahydropyrrolo[1,2-a]pyrazine | 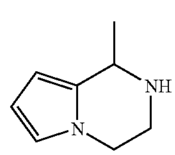 | B |
| A22 | 1-tert-butyl-1,2,3,4-tetrahydropyrrolo[1,2-a]pyrazine | 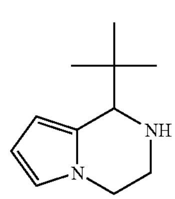 | B |

N-Acylation with Malonic Acid Monoethyl Ester Chloride or Succinic Acid Monoethyl Ester Chloride

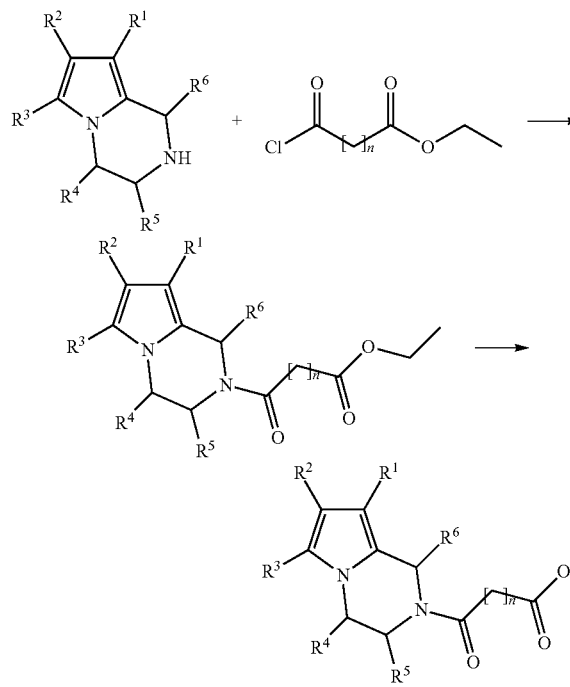

The corresponding 1-aryl-tetrahydropyrrolopyrazine (12.0 mmol) was introduced into a round-bottomed flask provided with a CaCl$_2$ drying tube and was dissolved in DCE (40 ml). TEA (1.2-2 mol-eq., based on the acid chloride) was added to this very well-stirred solution and 1.2-2 mol-eq. (based on the 1-aryl-tetrahydropyrrolopyrazine) of the corresponding acid chloride were then added, the round-bottomed flask was flushed with nitrogen and the reaction mixture was heated gently (approx. 40° C., TLC control) for 2-4 h. When the reaction had ended, the solution was diluted with DCE (approx. 25 ml) and extracted twice with water (2×10 ml). The aqueous phase was extracted twice more with DCE (2×10 ml) and the combined organic phases were dried over MgSO$_4$ and concentrated in vacuo. The crude product was used for further reactions without further purification. Yield: 80-90%.

The crude product of the acylation with malonic acid monoethyl ester chloride or succinic acid monoethyl ester chloride (approx. 10 mmol) was dissolved in a mixture of ethanol/water and NaOH (12 ml/3 ml/1.2 mol-eq. of solid NaOH, based on the ester) and the solution was stirred under a nitrogen atmosphere at room temperature until the reaction had ended (TLC control). The ethanol was removed in vacuo and the oil formed was dissolved in water (approx. 20 ml) and washed with either ethyl acetate or diethyl ether. The basic aqueous phase was freed of residues of the organic solvent on a rotary evaporator and, after cooling to below 10° C. in an ice-bath, was acidified (approx. pH 4-6, depending on the calculated logD value) with 3% strength aqueous HCl and extracted with DCM (2×25 ml). After drying over MgSO$_4$, the solvent was removed under reduced pressure.

Purification was carried out either by column chromatography (silica gel, mobile phase chloroform) or by dissolving in chloroform, or the crude product was dissolved in chloroform, silica gel was added and the mixture was then filtered. The residue was then recrystallized from 2-propanol/n-hexane. Yield: 35%—quantitative Amidation of the Malonic Acid and Succinic Acid Derivatives

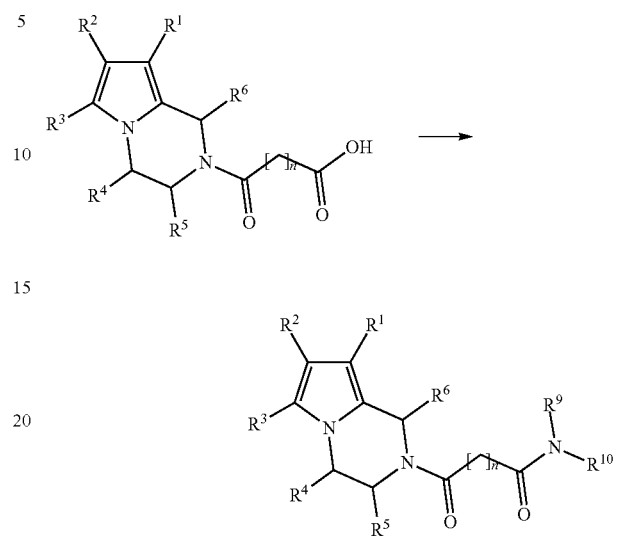

Automated Synthesis

A solution of the corresponding malonic acid or succinic acid derivative (250 µmol, 0.1-0.2 M in DCE, 1.25-2.5 ml) in a conical screw-cap glass was first initially introduced with the aid of a Cavro RSP 9000 robot system into a reactor (6×8Matrix) with the possibility of heating and stirring. The solution was prepared by mixing the corresponding malonic acid or succinic acid derivative, which had been dried in a vacuum drying cabinet, with 1.05 mol-eq. of 1,1'-carbonyldiimidazole in DCE and then leaving the mixture to stand under anhydrous conditions at room temperature for 1.5 h. The solution was then diluted such that a 0.1-0.2 molar solution was present.

The corresponding amine (275 µmol, 0.5 M, 0.55 ml) was added to this solution and the reaction vessel was closed. The reaction was as a rule carried out at room temperature, only aromatic amines had to be heated to 60° C.

The mixture was worked up by washing first with K$_2$CO$_3$ solution (5% in water, 1 ml) and then with water (1 ml). If traces of amine were still detected in the subsequent TLC control, the mixture was washed first with HCl solution (3% in water, 1 ml), then with K$_2$CO$_3$ solution (5% in water, 1 ml) and subsequently with water (1 ml). The organic phase was diluted with ethanol (0.5 ml) and transferred into tared glasses. The solvent was then stripped off to constant weight in vacuo.

Synthesis of Monoalkylated Amines

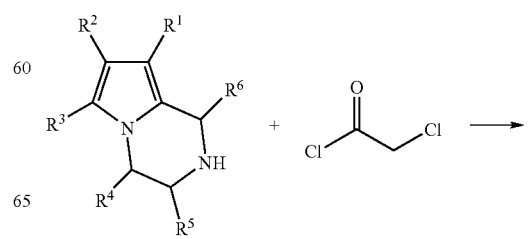

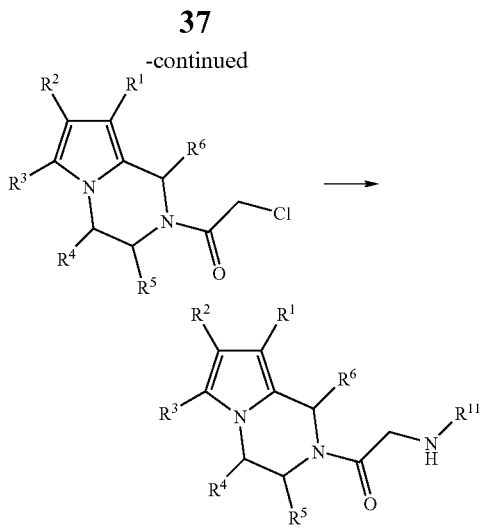

The corresponding 1-aryl-tetrahydropyrrolopyrazine (72 mmol) was introduced into a round-bottomed flask provided with a $CaCl_2$ drying tube and was dissolved in DCE (200 ml). TEA (2 mol-eq., based on the acid chloride) was added to this very well-stirred solution and 1.2 mol-eq. (based on the 1-aryl-tetrahydropyrrolopyrazine) of chloroacetic acid chloride were then added, the round-bottomed flask was flushed with nitrogen and the reaction mixture was heated gently (approx. 40° C., TLC control) for 2-3 hours.

When the reaction had ended, the solution was diluted with DCE (approx. 120 ml) and extracted twice with water (2×10 ml). The aqueous phase was extracted twice more with DCE (2×50 ml) and the combined organic phases were dried over $MgSO_4$ and concentrated in vacuo. The crude product was used for further reactions without further purification.

The corresponding 1-aryl-tetrahydropyrrolopyrazine (8-12 mmol) and the corresponding primary amine (20-30 ml, approx. 25-40 mol-eq.) were combined in a 100 ml round-bottomed flask provided with a $CaCl_2$ drying tube. The reaction mixture was stirred overnight at room temperature until the reaction was complete. The excess amine was stripped off in vacuo and the oil which remained was taken up in diethyl ether (50 ml) and extracted twice with acetic acid (3% in water, in each case 50 ml). The combined aqueous phases were cooled in an ice-bath and adjusted to approx. pH 8-9 with $Na_2CO_3$ solution (10% in water). The mixture was then extracted four times with 50 ml of DCM each time and the combined organic phases were washed with water, dried over $MgSO_4$ and concentrated in vacuo. As a rule, it was possible to use the product further without further purification. In some cases, purification was carried out by column chromatography (silica gel, $CHCl_3$). Yield: 50-75%

Acylation of the Monoalkylated Amines

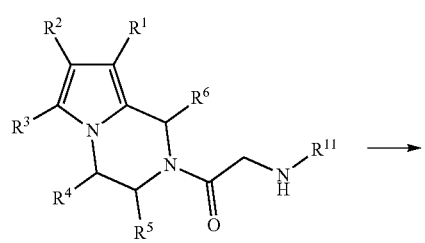

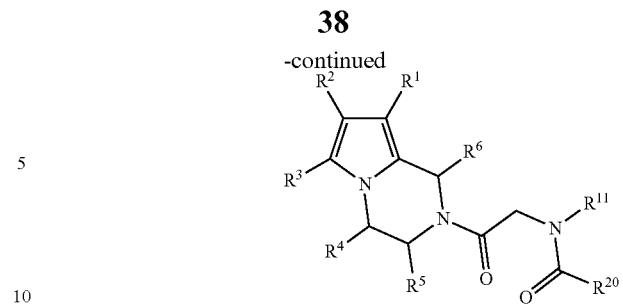

Automated Synthesis

A solution of the corresponding monoalkylated amine (250 μmol, 0.1-0.2 M in DCE, 1.25-2.5 ml) in a conical screw-cap glass was first initially introduced with the aid of a Cavro RSP 9000 robot system into a reactor (6×8Matrix) with the possibility of heating and stirring and subsequently first a solution of TEA (500 μmol, 1 M in DCE, 0.5 ml) and then a solution of the corresponding carboxylic acid chloride (275 μmol, 0.5 M in DCE, 0.55 ml) were added, the glass was closed and the mixture was stirred at room temperature until the reaction was complete (TLC control).

Purification was carried out with the aid of the Cavro RSP 9000 robot system. For the purification, $K_2CO_3$ solution (5% in water, 1 ml) was first pipetted in to remove residues of the carboxylic acids. The organic phase was then washed with water (1 ml). If traces of the carboxylic acid were still detected according to the TLC control, tris-(aminoethyl)-amine scavenger resin was used. To separate off any traces of the 1-aryl-tetrahydropyrrolopyrazine present, the organic phase was washed with HCl solution (3% in water, 1 ml) and then with $K_2CO_3$ solution (5% in water, 1 ml). The organic phase was diluted with ethanol (0.5 ml) and transferred into tared glasses. The solvent was then stripped off to constant weight in vacuo.

Sulfonylation of the Monoalkylated Amines

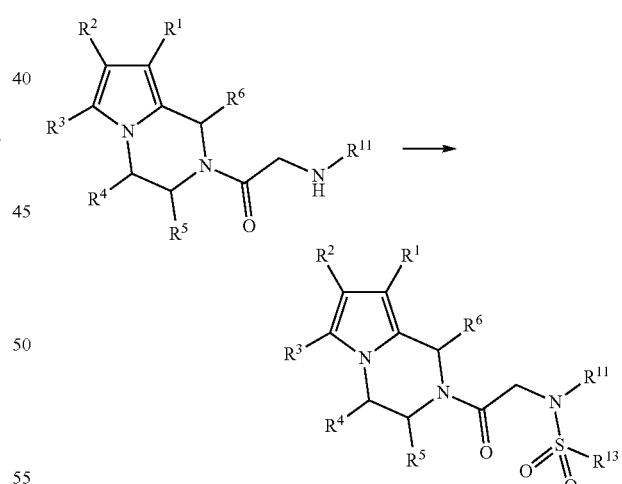

Automated Synthesis

A solution of the corresponding monoalkylated amine (250 mmol, 0.1-0.2 M in DCE, 1.25-2.5 ml) in a conical screw-cap glass was first initially introduced with the aid of a Cavro RSP 9000 robot system into a reactor (6×8Matrix) with the possibility of heating and stirring and subsequently first a solution of TEA (500 μmol, 1 M in DCE, 0.5 ml) and then a solution of the corresponding sulfonic acid chloride (275 μmol, 0.5 M in DCE, 0.55 ml) were added, the glass was closed and the mixture was stirred at room temperature until the reaction was complete (TLC control).

Purification was carried out with the aid of the Cavro RSP 9000 robot system. For the purification, $K_2CO_3$ solution (5% in water, 1 ml) was first pipetted in to remove residues of the sulfonic acids. The organic phase was then washed with water (1 ml). If traces of the sulfonic acid were still detected according to the TLC control, tris-(aminoethyl)-amine scavenger resin was used. To separate off any traces of the 1-aryl-tetrahydropyrrolopyrazine present, the organic phase was washed with HCl solution (3% in water, 1 ml) and then with $K_2CO_3$ solution (5% in water, 1 ml). The organic phase was diluted with ethanol (0.5 ml) and transferred into tared glasses. The solvent was then stripped off to constant weight in vacuo.

Ureas of the Monoalkylated Amines

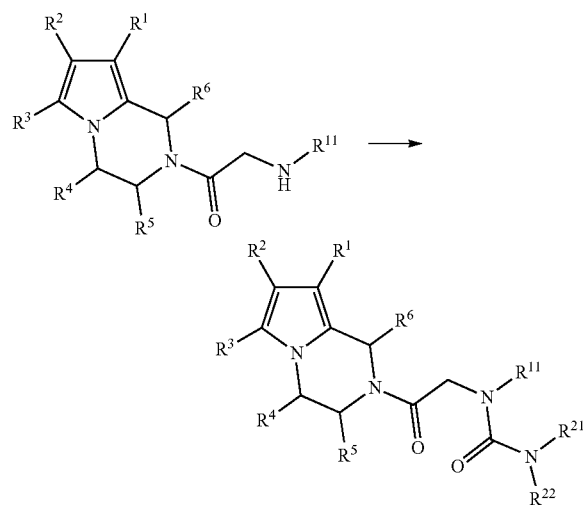

A solution of the corresponding monoalkylated amine (250 µmol, 0.1-0.2 M in DCE, 1.25-2.5 ml) in a conical screw-cap glass was first initially introduced with the aid of a Cavro RSP 9000 robot system into a reactor (6×8Matrix) with the possibility of heating and stirring and a solution of the corresponding isocyanate (250 µmol, 0.5 M, 0.5 ml) was then added, the glass was closed and the mixture was stirred at room temperature until the reaction was complete (TLC control), further isocyanate solution being added if appropriate.

Purification was carried out with the aid of the Cavro RSP 9000 robot system. To separate off any traces of the 1-aryl-tetrahydropyrrolopyrazine present, the organic phase was washed with HCl solution (3% in water, 1 ml) and then first with $K_2CO_3$ solution (5% in water, 1 ml) and then with water (1 ml). The organic phase was diluted with ethanol (0.5 ml) and transferred into tared glasses. The solvent was then stripped off to constant weight in vacuo.

N-Alkylation on the 1-aryltetrahydropyrrolopyrazine Matrix

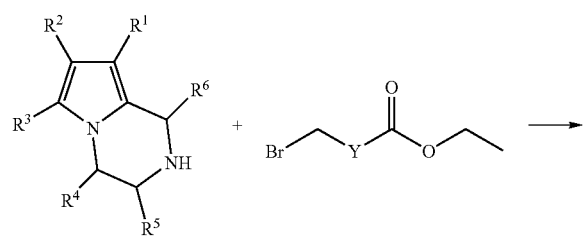

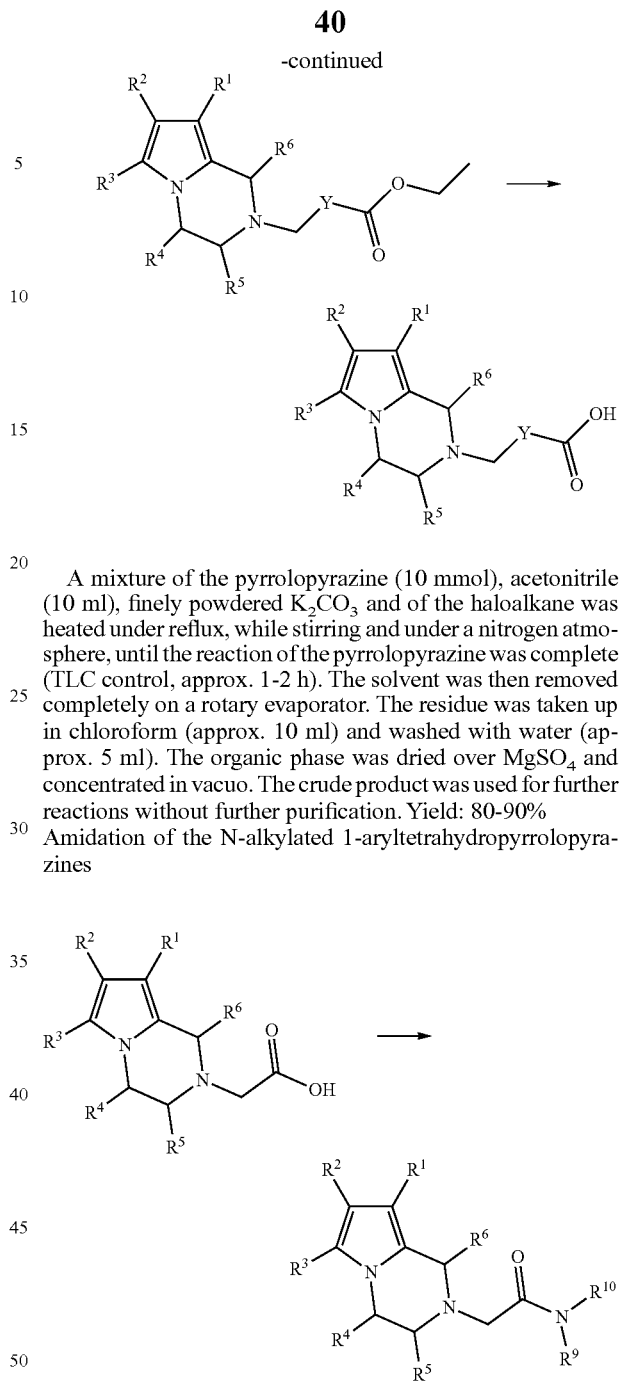

A mixture of the pyrrolopyrazine (10 mmol), acetonitrile (10 ml), finely powdered $K_2CO_3$ and of the haloalkane was heated under reflux, while stirring and under a nitrogen atmosphere, until the reaction of the pyrrolopyrazine was complete (TLC control, approx. 1-2 h). The solvent was then removed completely on a rotary evaporator. The residue was taken up in chloroform (approx. 10 ml) and washed with water (approx. 5 ml). The organic phase was dried over $MgSO_4$ and concentrated in vacuo. The crude product was used for further reactions without further purification. Yield: 80-90%

Amidation of the N-alkylated 1-aryltetrahydropyrrolopyrazines

Automated Synthesis

A solution of the corresponding malonic acid or succinic acid derivative (250 µmol, 0.1-0.2 M in DCE, 1.25-2.5 ml) in a conical screw-cap glass was first initially introduced with the aid of a Cavro RSP 9000 robot system into a reactor (6×8Matrix) with the possibility of heating and stirring. The solution was prepared by mixing the corresponding malonic acid or succinic acid derivative, which had been dried in a vacuum drying cabinet, with 1.05 mol-eq. of 1,1'-carbonyl-diimidazole in DCE and then leaving the mixture to stand under anhydrous conditions at room temperature for 1.5 h. The solution was then diluted such that a 0.1-0.2 molar solution was present.

The corresponding amine (275 µmol, 0.5 M, 0.55 ml) was added to this solution and the reaction vessel was closed. The reaction was as a rule carried out at room temperature, only aromatic amines had to be heated to 60° C.

For working up, the mixture was washed first with $K_2CO_3$ solution (5% in water, 1 ml) and then with water (1 ml). If traces of amine were still detected in the subsequent TLC control, the mixture was washed first with HCl solution (3% in water, 1 ml), then with $K_2CO_3$ solution (5% in water, 1 ml) and subsequently with water (1 ml).

The organic phase was diluted with ethanol (0.5 ml) and transferred into tared glasses. The solvent was then stripped off to constant weight in vacuo.

2-[1-(2,3-dihydro-benzo[1,4]dioxin-6-yl)-3,4-dihydro-1H-pyrrolo[1,2-a]pyrazin-2-yl]-N-(3-trifluoromethyl-benzyl)-acetamide 8

1H NMR (600 MHz, DMSO-$d_6$) d ppm 2.69-2.96 (m, 2H) 2.96-3.16 (m, 2H) 3.86-4.09 (m, 1H) 4.14-4.28 (m, 5H) 4.35 (m, 2H) 4.51 (s, 1H) 5.17 (br. s., 1H) 5.90 (t, J=3.02 Hz, 1H) 6.62 (br. s., 1H) 6.77 (d, J=8.31 Hz, 1H) 6.86 (dd, J=8.31, 1.51 Hz, 1H) 6.92 (d, J=2.27 Hz, 1H) 7.49-7.63 (m, 4H) 8.62 (t, J=6.04 Hz, 1H)

The following examples were synthesized in accordance with the instructions given above and purified via HPLC. The analysis was carried out via HPLC-MS. In all cases, the mass was detected via ESI-MS; the purity was above 85%.

| No. | Name | Mass |
|---|---|---|
| 1 | 4-[1-(4-chloro-phenyl)-3,4-dihydro-1H-pyrrolo[1,2-a]pyrazin-2-yl]-4-oxo-N-(3-trifluoromethyl-benzyl)-butyramide | 489.1 |
| 2 | 4-oxo-4-(1-phenyl-3,4-dihydro-1H-pyrrolo[1,2-a]pyrazin-2-yl)-N-(3-trifluoromethyl-benzyl)-butyramide | 455.2 |
| 3 | N-sec-butyl-2-[1-(2-methoxy-phenyl)-3,4-dihydro-1H-pyrrolo[1,2-a]pyrazin-2-yl]-acetamide | 341.2 |
| 4 | N-cyclopropyl-3-[1-(3-fluoro-phenyl)-3,4-dihydro-1H-pyrrolo[1,2-a]pyrazin-2-yl]-3-oxo-propionamide | 341.2 |
| 5 | 4-oxo-4-(1-m-tolyl-3,4-dihydro-1H-pyrrolo[1,2-a]pyrazin-2-yl)-N-(3-trifluoromethyl-benzyl)-butyramide | 469.2 |
| 6 | 3-{2-[1-(2-chloro-phenyl)-3,4-dihydro-1H-pyrrolo[1,2-a]pyrazin-2-yl]-2-oxo-ethyl}-1,1-dimethyl-urea | 360.1 |
| 7 | 4-[1-(4-fluoro-phenyl)-3,4-dihydro-1H-pyrrolo[1,2-a]pyrazin-2-yl]-N-isobutyl-4-oxo-butyramide | 371.2 |
| 8 | 2-[1-(2,3-dihydro-benzo[1,4]dioxin-6-yl)-3,4-dihydro-1H-pyrrolo[1,2-a]pyrazin-2-yl]-N-(3-trifluoromethyl-benzyl)-acetamide | 471.2 |
| 9 | 2-[1-(2,3-dihydro-benzo[1,4]dioxin-6-yl)-3,4-dihydro-1H-pyrrolo[1,2-a]pyrazin-2-yl]-N-p-tolyl-acetamide | 403.2 |
| 10 | 3-tert-butyl-1-{2-[1-(2,4-difluoro-phenyl)-3,4-dihydro-1H-pyrrolo[1,2-a]pyrazin-2-yl]-2-oxo-ethyl}-1-isopropyl-urea | 432.2 |
| 11 | 2-[1-(2,3-dihydro-benzo[1,4]dioxin-6-yl)-3,4-dihydro-1H-pyrrolo[1,2-a]pyrazin-2-yl]-N-isopropyl-acetamide | 355.2 |
| 12 | 3-tert-butyl-1-isopropyl-1-[2-oxo-2-(1-m-tolyl-3,4-dihydro-1H-pyrrolo[1,2-a]pyrazin-2-yl)-ethyl]-urea | 410.3 |
| 13 | N-cyclopropyl-N-[2-(1-furan-3-yl-3,4-dihydro-1H-pyrrolo[1,2-a]pyrazin-2-yl)-2-oxo-ethyl]-4-methyl-benzamide | 403.2 |
| 14 | cyclopropanecarboxylic acid {2-[1-(3,4-dichloro-phenyl)-3,4-dihydro-1H-pyrrolo[1,2-a]pyrazin-2-yl]-2-oxo-ethyl}-isopropyl-amide | 433.1 |
| 15 | 1-cyclopropyl-1-{2-[1-(2,4-difluoro-phenyl)-3,4-dihydro-1H-pyrrolo[1,2-a]pyrazin-2-yl]-2-oxo-ethyl}-3-isopropyl-urea | 416.2 |
| 16 | 1-(4-acetyl-piperazin-1-yl)-2-[1-(2,4-difluoro-phenyl)-3,4-dihydro-1H-pyrrolo[1,2-a]pyrazin-2-yl]-ethanone | 402.2 |
| 17 | furan-2-carboxylic acid cyclopropyl-{2-[1-(3,4-dichloro-phenyl)-3,4-dihydro-1H-pyrrolo[1,2-a]pyrazin-2-yl]-2-oxo-ethyl}-amide | 457.1 |
| 18 | N-tert-butyl-N-[2-oxo-2-(1-p-tolyl-3,4-dihydro-1H-pyrrolo[1,2-a]pyrazin-2-yl)-ethyl]-isobutyramide | 395.3 |
| 19 | N-cyclopropyl-N-{2-[1-(3,4-dichloro-phenyl)-3,4-dihydro-1H-pyrrolo[1,2-a]pyrazin-2-yl]-2-oxo-ethyl}-isobutyramide | 433.1 |
| 20 | 2-(1-(3-methoxyphenyl)-3,4-dihydropyrrolo[1,2-a]pyrazin-2(1H)-yl)-N-(3-(trifluoromethyl)benzyl)acetamide | 443.2 |
| 21 | 1-ethyl-3,3-dimethyl-1-[2-oxo-2-(1-phenyl-3,4-dihydro-1H-pyrrolo[1,2-a]pyrazin-2-yl)-ethyl]-urea | 354.2 |
| 22 | quinoline-8-sulfonic acid {2-[1-(2,4-difluoro-phenyl)-3,4-dihydro-1H-pyrrolo[1,2-a]pyrazin-2-yl]-2-oxo-ethyl}-ethyl-amide | 510.2 |
| 23 | N-cyclopropyl-2-(1-p-tolyl-3,4-dihydro-1H-pyrrolo[1,2-a]pyrazin-2-yl)-acetamide | 309.2 |
| 24 | cyclopropanecarboxylic acid tert-butyl-[2-oxo-2-(1-p-tolyl-3,4-dihydro-1H-pyrrolo[1,2-a]pyrazin-2-yl)-ethyl]-amide | 393.2 |
| 25 | furan-2-carboxylic acid tert-butyl-{2-[1-(3,4-dichloro-phenyl)-3,4-dihydro-1H-pyrrolo[1,2-a]pyrazin-2-yl]-2-oxo-ethyl}-amide | 473.1 |
| 26 | 2-[1-(2-chloro-phenyl)-3,4-dihydro-1H-pyrrolo[1,2-a]pyrazin-2-yl]-1-piperidin-1-yl-ethanone | 357.2 |
| 27 | 2-phenyl-cyclopropanecarboxylic acid ethyl-[2-oxo-2-(1-phenyl-3,4-dihydro-1H-pyrrolo[1,2-a]pyrazin-2-yl)-ethyl]-amide | 427.2 |
| 29 | N-(4-fluoro-phenyl)-4-[1-(3-methoxy-phenyl)-3,4-dihydro-1H-pyrrolo[1,2-a]pyrazin-2-yl]-4-oxo-butyramide | 421.2 |
| 30 | N-ethyl-N-[2-oxo-2-(1-phenyl-3,4-dihydro-1H-pyrrolo[1,2-a]pyrazin-2-yl)-ethyl]-butyramide | 353.2 |
| 31 | N-(1,2-dimethyl-propyl)-2-(1-p-tolyl-3,4-dihydro-1H-pyrrolo[1,2-a]pyrazin-2-yl)-acetamide | 339.2 |
| 32 | N-sec-butyl-2-(1-p-tolyl-3,4-dihydro-1H-pyrrolo[1,2-a]pyrazin-2-yl)-acetamide | 325.2 |
| 33 | N-{2-[1-(3,4-dichloro-phenyl)-3,4-dihydro-1H-pyrrolo[1,2-a]pyrazin-2-yl]-2-oxo-ethyl}-N-ethyl-isobutyramide | 421.1 |
| 34 | 4-[1-(3-methoxy-phenyl)-3,4-dihydro-1H-pyrrolo[1,2-a]pyrazin-2-yl]-4-oxo-N-pyridin-4-ylmethyl-butyramide | 418.2 |
| 35 | furan-2-carboxylic acid isopropyl-{2-[1-(4-isopropyl-phenyl)-3,4-dihydro-1H-pyrrolo[1,2-a]pyrazin-2-yl]-2-oxo-ethyl}-amide | 433.2 |
| 36 | 1-[1-(3-methoxy-phenyl)-3,4-dihydro-1H-pyrrolo[1,2-a]pyrazin-2-yl]-3-morpholin-4-yl-propane-1,3-dione | 383.2 |
| 37 | 2-(1-p-tolyl-3,4-dihydro-1H-pyrrolo[1,2-a]pyrazin-2-yl)-N-(3-trifluoromethyl-benzyl)-acetamide | 427.2 |
| 38 | N-pyridin-3-ylmethyl-2-(1-p-tolyl-3,4-dihydro-1H-pyrrolo[1,2-a]pyrazin-2-yl)-acetamide | 360.2 |
| 39 | 2-[1-(2,4-difluoro-phenyl)-3,4-dihydro-1H-pyrrolo[1,2-a]pyrazin-2-yl]-N-furan-2-ylmethyl-acetamide | 371.1 |
| 41 | N-benzyl-2-(1-p-tolyl-3,4-dihydro-1H-pyrrolo[1,2-a]pyrazin-2-yl)-acetamide | 359.2 |
| 42 | N-(3,4-dimethyl-phenyl)-3-[1-(3-methoxy-phenyl)-3,4-dihydro-1H-pyrrolo[1,2-a]pyrazin-2-yl]-3-oxo-propionamide | 417.2 |
| 43 | 4-[1-(3-chloro-phenyl)-3,4-dihydro-1H-pyrrolo[1,2-a]pyrazin-2-yl]-N-isopropyl-4-oxo-butyramide | 373.2 |
| 44 | N-(1-benzyl-piperidin-4-yl)-2-(1-p-tolyl-3,4-dihydro-1H-pyrrolo[1,2-a]pyrazin-2-yl)-acetamide | 442.3 |
| 45 | 2-[1-(4-chloro-phenyl)-3,4-dihydro-1H-pyrrolo[1,2-a]pyrazin-2-yl]-1-[4-(2-chloro-phenyl)-piperazin-1-yl]-ethanone | 468.1 |
| 46 | N-(1-benzyl-piperidin-4-yl)-2-[1-(4-chloro-phenyl)-3,4-dihydro-1H-pyrrolo[1,2-a]pyrazin-2-yl]-acetamide | 462.2 |
| 48 | 1-(4-benzo[1,3]dioxol-5-ylmethyl-piperazin-1-yl)-2-[1-(4-chloro-phenyl)-3,4-dihydro-1H-pyrrolo[1,2-a]pyrazin-2-yl]-ethanone | 492.2 |
| 49 | N-phenethyl-2-(1-p-tolyl-3,4-dihydro-1H-pyrrolo[1,2-a]pyrazin-2-yl)-acetamide | 373.2 |
| 50 | 2-[1-(3,4-dichloro-phenyl)-3,4-dihydro-1H-pyrrolo[1,2-a]pyrazin-2-yl]-N-(2-pyridin-2-yl-ethyl)-acetamide | 428.1 |
| 51 | 1-(4-benzo[1,3]dioxol-5-ylmethyl-piperazin-1-yl)-2-(1-p-tolyl-3,4-dihydro-1H-pyrrolo[1,2-a]pyrazin-2-yl)-ethanone | 472.2 |
| 52 | 2-[1-(3,4-dichloro-phenyl)-3,4-dihydro-1H-pyrrolo[1,2-a]pyrazin-2-yl]-N-pyridin-3-ylmethyl-acetamide | 414.1 |
| 53 | 1-(4-benzo[1,3]dioxol-5-ylmethyl-piperazin-1-yl)-2-[1-(2-chloro-phenyl)-3,4-dihydro-1H-pyrrolo[1,2-a]pyrazin-2-yl]-ethanone | 492.2 |
| 54 | 1-(4-benzyl-piperazin-1-yl)-2-[1-(4-chloro-phenyl)-3,4-dihydro-1H-pyrrolo[1,2-a]pyrazin-2-yl]-ethanone | 448.2 |
| 55 | 2-[1-(4-chloro-phenyl)-3,4-dihydro-1H-pyrrolo[1,2-a]pyrazin-2-yl]-N-phenethyl-acetamide | 393.2 |
| 56 | 2-[1-(2-chloro-phenyl)-3,4-dihydro-1H-pyrrolo[1,2-a]pyrazin-2-yl]-N-phenethyl-acetamide | 393.2 |
| 57 | 2-[1-(3,4-dichloro-phenyl)-3,4-dihydro-1H-pyrrolo[1,2-a]pyrazin-2-yl]-N-(4-fluoro-benzyl)-acetamide | 431.1 |
| 58 | 1-(4-benzyl-piperazin-1-yl)-2-[1-(2-chloro-phenyl)-3,4-dihydro-1H-pyrrolo[1,2-a]pyrazin-2-yl]-ethanone | 448.2 |
| 59 | N-cyclohexyl-2-(1-p-tolyl-3,4-dihydro-1H-pyrrolo[1,2-a]pyrazin-2-yl)-acetamide | 351.2 |

-continued

| No. | Name | Mass |
|---|---|---|
| 60 | 1-(4-benzyl-piperazin-1-yl)-2-(1-p-tolyl-3,4-dihydro-1H-pyrrolo[1,2-a]pyrazin-2-yl)-ethanone | 428.3 |
| 61 | 2-[1-(4-chloro-phenyl)-3,4-dihydro-1H-pyrrolo[1,2-a]pyrazin-2-yl]-N-(1,2-dimethyl-propyl)-acetamide | 359.2 |
| 62 | N-(2-piperidin-1-yl-ethyl)-2-(1-p-tolyl-3,4-dihydro-1H-pyrrolo[1,2-a]pyrazin-2-yl)-acetamide | 380.3 |
| 65 | N-(4-fluoro-phenyl)-2-(1-p-tolyl-3,4-dihydro-1H-pyrrolo[1,2-a]pyrazin-2-yl)-acetamide | 363.2 |
| 66 | furan-2-carboxylic acid ethyl-[2-oxo-2-(1-p-tolyl-3,4-dihydro-1H-pyrrolo[1,2-a]pyrazin-2-yl)-ethyl]-amide | 391.2 |
| 67 | 2-[1-(4-fluoro-phenyl)-3,4-dihydro-1H-pyrrolo[1,2-a]pyrazin-2-yl]-N-isopropyl-acetamide | 315.2 |
| 68 | 2-[1-(3,4-dichloro-phenyl)-3,4-dihydro-1H-pyrrolo[1,2-a]pyrazin-2-yl]-N-isobutyl-acetamide | 379.1 |
| 69 | 2-[1-(4-chloro-phenyl)-3,4-dihydro-1H-pyrrolo[1,2-a]pyrazin-2-yl]-N-(2-pyrrolidin-1-yl-ethyl)-acetamide | 386.2 |
| 70 | N-benzo[1,3]dioxol-5-ylmethyl-2-(1-p-tolyl-3,4-dihydro-1H-pyrrolo[1,2-a]pyrazin-2-yl)-acetamide | 403.2 |
| 71 | 2-(1-(4-chlorophenyl)-3,4-dihydropyrrolo[1,2-a]pyrazin-2(1H)-yl)-N-(4-fluorobenzyl)acetamide | 397.1 |
| 72 | 2-(1-(4-chlorophenyl)-3,4-dihydropyrrolo[1,2-a]pyrazin-2(1H)-yl)-N-(3-(trifluoromethyl)benzyl)acetamide | 447.1 |
| 73 | 2-(1-(4-chlorophenyl)-3,4-dihydropyrrolo[1,2-a]pyrazin-2(1H)-yl)-1-(4-(4-methoxyphenyl)piperazin-1-yl)ethanone | 464.2 |
| 74 | N-(2,4-dichlorophenethyl)-2-(1-(3,4-dichlorophenyl)-3,4-dihydropyrrolo[1,2-a]pyrazin-2(1H)-yl)acetamide | 495.0 |
| 75 | 1-(4-(3-chlorophenyl)piperazin-1-yl)-4-(1-m-tolyl-3,4-dihydropyrrolo[1,2-a]pyrazin-2(1H)-yl)butane-1,4-dione | 490.2 |

Synthesis of the compounds of Examples 76 to 82, 87, 88 and 92

Synthesis of 4-oxo-4-(3-(trifluoromethyl)benzylamino)butanoic acid (S1)

A solution of 15.0 g (85.6 mmol) of 3-(trifluoromethyl) phenyl)methylamine in ether (18 ml) was added dropwise in the course of 30 min to a suspension of 7.54 g (75.4 mmol) of succinic anhydride in ether (89 ml). Stirring was then carried out for 72 h at RT. The resulting precipitate was filtered off with suction and then washed with ether. The residue was dried and then crystallized from ether. CC (EA/MeOH 2:1) of the crystallization product yielded 13.2 g (47.9 mmol, 64%) of 4-oxo-4-(3-(trifluoromethyl)benzylamino)butanoic acid (S1).

Synthesis of 4-oxo-4-(1-(3-(trifluoromethyl)phenyl) ethylamino)butanoic acid (S2)

A solution of 5.0 g (26.5 mmol) of 1-(3-(trifluoromethyl) phenyl)ethylamine in ether (6 ml) was added dropwise in the course of 30 min to a suspension of 2.33 g (23.3 mmol) of succinic anhydride in ether (28 ml). Stirring was then carried out for 72 h at RT. The resulting precipitate was filtered off with suction and dried for 1 h in vacuo at 40° C. CC (EA/MeOH 1:4) of the residue yielded 3.68 g (12.7 mmol, 55%) of 4-oxo-4-(1-(3-(trifluoromethyl)phenyl)ethylamino)-butanoic acid (S2).

Synthesis of (E)-2-(3-(2-fluorophenyl)acrylamido)acetic acid S7 a) Synthesis of (E)-2-(3-(2-fluorophenyl)acrylamido) acetic acid methyl ester (3.9 g, 24.0 mmol) of CDI were added to a solution of (3.3 g, 20.0 mmol) of T-fluorocinnamic acid in DCE (60 ml), and the reaction solution was stirred for 2 h at RT. (2.76 g, 22.0 mmol) of glycine methyl ester hydrochloride and (4.37 g, 25.0 mmol) of diisopropylethylamine were then added and stirring was carried out for a further 5 h at RT. The mixture was then diluted with DCM (20 ml) and washed with water. The organic phase was dried over MgSO$_4$, filtered and concentrated in vacuo. CC (DCE/ethanol 20:1) with the residue yielded 2.4 g (10.1 mmol, 51%) of (E)-2-(3-(2-fluorophenyl) acrylamido)acetic acid methyl ester.

b) Synthesis of (E)-2-(3-(2-fluorophenyl)acrylamido)acetic acid

A solution of (400 mg, 10.0 mmol) of sodium hydroxide in water (2 ml) was added to a solution of (2.34 g, 9.9 mmol) of (E)-2-(3-(2-fluorophenyl)acrylamido)acetic acid methyl ester in ethanol (50 ml). The reaction solution was stirred for 1 h at RT and then concentrated in vacuo. The residue was taken up in water and washed twice with ethyl acetate. The aqueous phase was then adjusted carefully to pH 4 with 3% hydrochloric acid, and extraction with ethyl acetate was carried out. The organic phase was concentrated in vacuo, 1.22 g (5.5 mmol, 55%) of (E)-2-(3-(2-fluorophenyl)acrylamido) acetic acid (S7) being obtained as residue.

2-Amino-1-(1-phenyl-3,4-dihydropyrrolo[1,2-a] pyrazin-2(1H)-yl)ethanone A23 a) Synthesis of tert-butyl 2-oxo-2-(1-phenyl-3,4-dihydropyrrolo[1,2-a]pyrazin-2(1H)-yl)ethylcarbamate (1.1 g, 7.0 mmol) of CDI were added to a solution of Boc-glycine (1.2 g, 6.7 mmol) in DCE (20 ml), and stirring was carried out for 100 min at RT. (1.3 g, 6.7 mmol) of 1-phenyl-1,2,3,4-tetrahydropyrrolo[1,2-a]pyrazine (A2) were then added, and stirring was carried out for a further 2 h at RT. The mixture was then heated for 2 h at 50° C. (450 mg, 2 mmol) of Boc-glycine imidazolide were subsequently added, and the mixture was heated for 2 h under reflux. After cooling to RT, washing was carried out with, in succession, a 5% aq. sodium carbonate solution, a 5% aq. citric acid solution, water and brine. The organic phase was dried over MgSO$_4$, filtered and concentrated in vacuo. CC (DCE) with the residue yielded 1.4 g (4.1 mmol, 61%) of tert-butyl 2-oxo-2-(1-phenyl-3,4-dihydropyrrolo[1,2-a]pyrazin-2(1H)-yl)ethylcarbamate.

b) Synthesis of 2-amino-1-(1-phenyl-3,4-dihydropyrrolo[1,2-a]pyrazin-2(1H)-yl)ethanone TFA (20 ml) was added to a solution of (1.6 g, 4.6 mmol) of tert-butyl 2-oxo-2-(1-phenyl-3,4-dihydropyrrolo[1,2-a] pyrazin-2(1H)-yl)ethylcarbamate in DCM (20 ml), and stirring was carried out for 1 h at RT. The mixture was then diluted with water, while cooling (ice-bath), and adjusted to pH 10 with 20% aq. potassium carbonate solution. The aqueous phase was saturated with sodium chloride, and extraction with chloroform was then carried out. The organic phase was dried over MgSO$_4$, filtered and concentrated in vacuo. CC (DCE/EtOH/conc. aq. NH$_3$ 5:1:0.06) yielded 298 mg (1.2 mmol, 26%) of 2-amino-1-(1-phenyl-3,4-dihydropyrrolo[1, 2-a]pyrazin-2(1H)-yl)ethanone (A23).
2. Acylation Reactions
3. Method A
The corresponding tetrahydropyrrolopyrazine (1.1 mmol), NEt$_3$ (263 µl, 1.9 mmol) and HATU (380 mg, 1.0 mmol) were added to a solution of the corresponding butanoic acid derivative (S1 or S2). The reaction solution was stirred for 2 d at RT and then concentrated in vacuo. The crude products were purified by CC (EA/DCM 1:9→1:1).

4. Method B

CDI (286 mg, 1.76 mmol) was added to a solution of (1.68 mmol) of the corresponding acid in DCM (27 ml), and stirring was carried out for 1 h at RT. The corresponding amine (1.68 mmol) was then added, and stirring was carried out for a further 16 h at RT. A 4N aq. ammonium chloride solution was then added and the phases were separated. The aqueous phase was extracted twice more with DCM. The organic phases were combined and washed with a 1M sodium bicarbonate solution, dried over MgSO$_4$ and concentrated in vacuo. The crude product was purified by CC (ethyl acetate).

5. Method C

The corresponding acid (1.05 mmol) and PS diimide (1.18 g, ~1.4 mmol) were added to a solution of the corresponding amine structural unit (0.7 mmol) in DCM (20 ml). Shaking was then carried out for 2 h at RT. The resin was then filtered off and washed several times with DCM and MeOH. The filtrate was concentrated in vacuo. CC (DCE/ethanol 20:1) with the residue yielded the corresponding product.

A. Synthesis of the Compounds of Examples 76 to 82

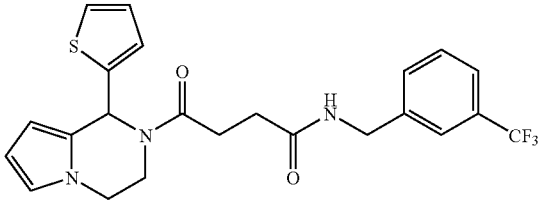

| Ex. | Structure and name | Precursor | Method | Yeild [mg] | % | MS m/z [M + H]$^+$ |
|---|---|---|---|---|---|---|
| 76 | 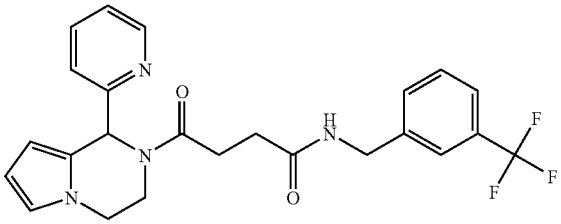 4-oxo-4-(1-(thiophen-2-yl)-3,4-dihydropyrrolo[1,2-a]pyrazin-2(1H)-yl)-N-(3-(trifluoromethyl)-benzyl)butanamide | S1 | A | 443 | 96 | 461.1 |
| 77 | 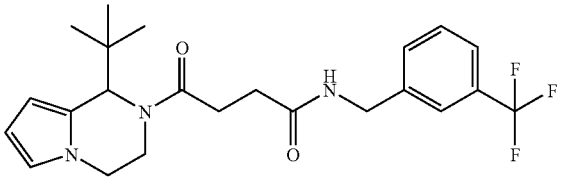 4-oxo-4-(1-(pyridin-2-yl)-3,4-dihydropyrrolo[1,2-a]pyrazin-2(1H)-yl)-N-(3-(trifluoromethyl)-benzyl)butanamide | S1 | A | 388 | 85 | 457.7 |
| 78 | 4-(1-tert-butyl-3,4-dihydropyrrolo[1,2-a]pyrazin-2(1H)-yl)-4-oxo-N-(3-(trifluoromethyl)benzyl)butanamide | S1 | A | 690 | 99 | 436.2 |

-continued
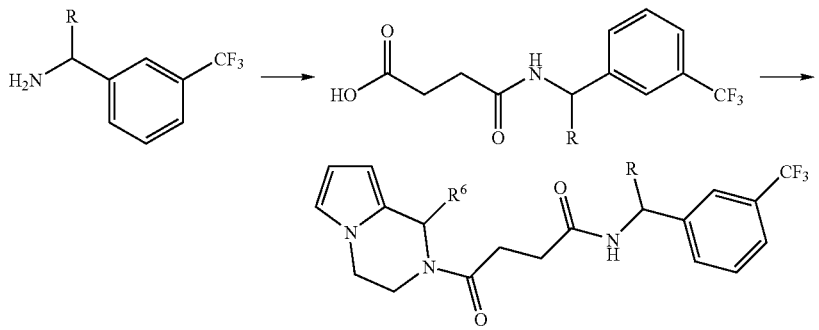
| Ex. | Structure and name | Precursor | Method | Yeild [mg] | % | MS m/z [M + H]+ |
|---|---|---|---|---|---|---|
| 79 | 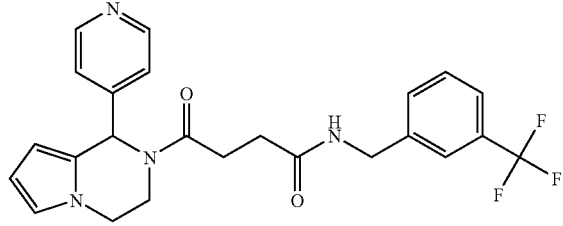  4-oxo-4-(1-(pyridin-4-yl)-3,4-dihydropyrrolo[1,2-a]pyrazin-2(1H)-yl)-N-(3-(trifluoromethyl)-benzyl)butanamide | S1 | A | 727 | 69 | 457.1 |
| 80 | 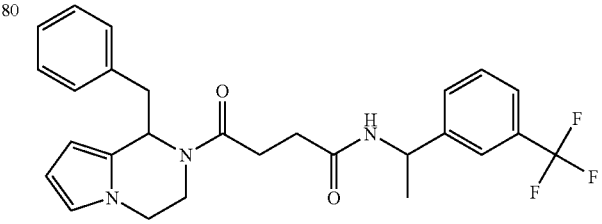  4-(1-benzyl-3,4-dihydropyrrolo[1,2-a]pyrazin-2(1H)-yl)-4-oxo-N-(1-(3-(trifluoromethyl)phenyl)-ethyl)butanamide | S2 | A | 181 | 51 | 484.2 |
| 81 | 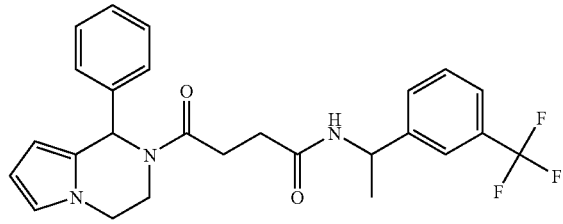  4-oxo-4-(1-phenyl-3,4-dihydropyrrolo[1,2-a]pyrazin-2(1H)-yl)-N-(1-(3-(trifluoromethyl)phenyl)ethyl)butanamide | S2 | A | 127 | 27 | 470.1 |

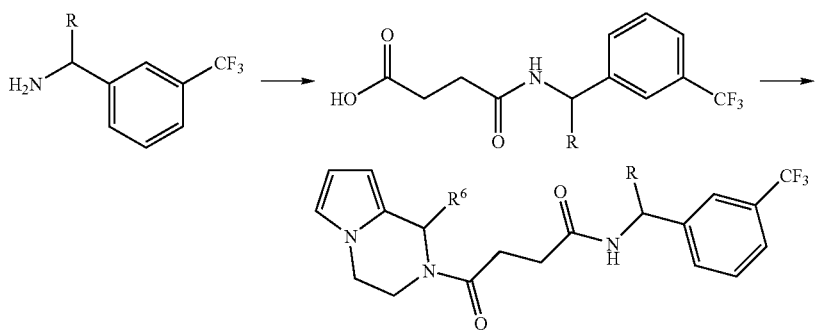
| Ex. | Structure and name | Precursor | Method | Yield [mg] | % | MS m/z [M + H]+ |
|---|---|---|---|---|---|---|
| 82 | 4-oxo-4-(1-(thiophen-2-yl)-3,4-dihydropyrrolo[1,2-a]pyrazin-2(1H)-yl)-N-(1-(3-(trifluoromethyl)phenyl)ethyl)butanamide | S2 | A | 320 | 90 | 476.1 |
6. Synthesis of the Compounds of Examples 87 and 88
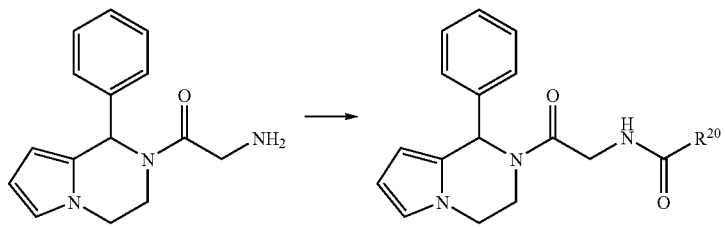
| Ex. | Structure and name | Precursor | Method | Yield [mg] | % | MS m/z [M + H]+ |
|---|---|---|---|---|---|---|
| 87 | N-(2-oxo-2-(1-phenyl-3,4-dihydropyrrolo[1,2-a]pyrazin-2(1H)-yl)ethyl)-3-(3-(trifluoromethyl)-phenyl)propanamide | A23 | B | 127 | 38 | 456.2 |

-continued
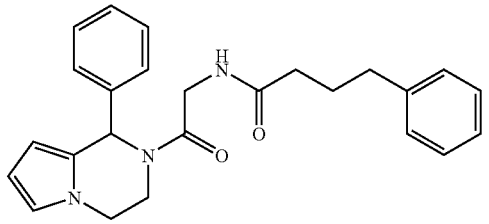
| Ex. | Structure and name | Precursor | Method | Yeild [mg] | % | MS m/z [M + H]+ |
|---|---|---|---|---|---|---|
| 88 | N-(2-oxo-2-(1-(phenyl-3,4-dihydropyrrolo[1,2-a]pyrazin-2(1H)-yl)ethyl)4-phenylbutanamide | A23 | C | 139 | 49 | 401.2 |
7. Synthesis of the Compound of Example 92
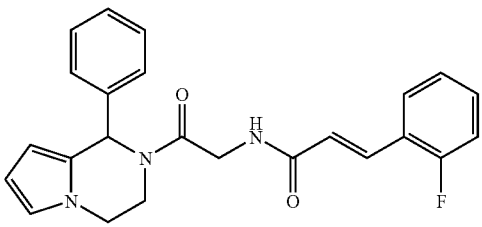
| Ex. | Structure and name | Precursor | Method | Yeild [mg] | % | MS m/z [M + H]+ |
|---|---|---|---|---|---|---|
| 92 | (E)-3-(2-fluorophenyl)-N-(2-oxo-2-(1-phenyl-3,4-dihydropyrrolo[1,2-a]pyrazin-2(1H)-yl)ethyl)-acrylamide | A2 | C | 109 | 29 | 404.2 |

A. Synthesis of the Compounds of Examples 83 to 86, 89 and 90

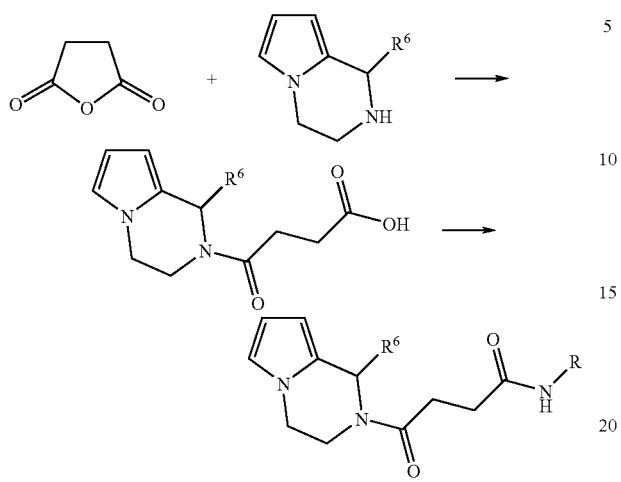

Synthesis of 4-oxo-4-(1-phenyl-3,4-dihydropyrrolo[1,2-a]pyrazin-2(1H)-yl)butanoic acid (S3)

1-Phenyl-1,2,3,4-tetrahydropyrrolo[1,2-a]pyrazine (A2) (396 mg, 2.0 mmol) and NEt₃ (277 µl, 2.0 mmol) were added to a suspension of succinic anhydride (176 mg, 1.76 mmol) in MeCN (28 ml), and stirring was carried out for 16 h at RT. The mixture was then diluted with EA (30 ml) and washed with 2N hydrochloric acid (2×5 ml). The organic phase was dried over MgSO₄, filtered and concentrated in vacuo. The resulting residue was taken up in EA (50 ml) and again washed with 2N hydrochloric acid (20 ml) and then with a sat. aq. sodium carbonate solution (2×30 ml). The organic phase was again dried over MgSO₄, filtered and concentrated in vacuo. CC (EA/MeOH 3:1) with the residue yielded 230 mg (0.77 mmol, 44%) of 4-oxo-4-(1-phenyl-3,4-dihydropyrrolo[1,2-a]pyrazin-2(1H)-yl)butanoic acid (S3).

Synthesis of 4-(1-methyl-3,4-dihydropyrrolo[1,2-a]pyrazin-2(1H)-yl)-4-oxobutanoic acid S4

A solution of (190 mg, 1.4 mmol) of 1-methyl-1,2,3,4-tetrahydropyrrolo[1,2-a]pyrazine (A21) in THF (10 ml) was added dropwise in the course of 30 min to a suspension of (558 mg, 5.6 mmol) of succinic anhydride in THF (10 ml). The mixture was then stirred for 2 h at RT and concentrated in vacuo. The residue was taken up in chloroform, washed with water and brine, dried over MgSO₄ and concentrated in vacuo. 257 mg (0.92 mmol, 54%) of 4-(1-methyl-3,4-dihydropyrrolo[1,2-a]pyrazin-2(1H)-yl)-4-oxobutanoic acid (S4) were obtained.

Synthesis of 3-oxo-3-(1-phenyl-3,4-dihydropyrrolo[1,2-a]pyrazin-2(1H)-yl)propanoic acid S5

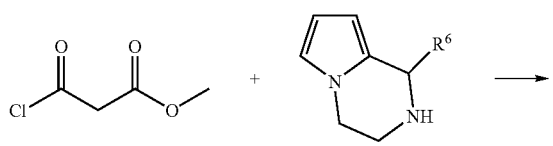

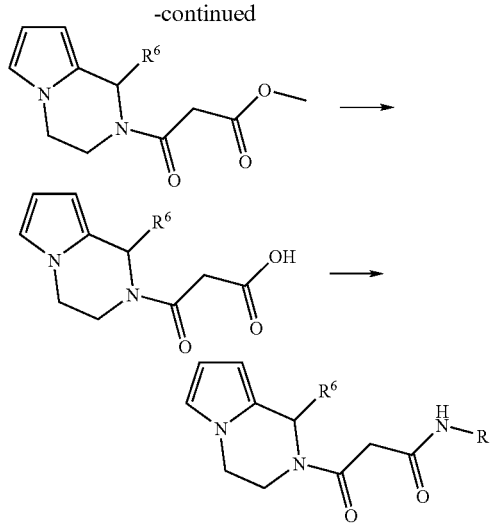

a) Synthesis of 3-oxo-3-(1-phenyl-3,4-dihydropyrrolo[1,2-a]pyrazin-2(1H)-yl)propanoic acid methyl ester A solution of (852 µl, 7.9 mmol) of methyl-malonyl chloride in DCM (5 ml) was added dropwise, with vigorous stirring and while cooling (ice-bath), to a solution of (1.5 g, 7.6 mmol) of 1-phenyl-1,2,3,4-tetrahydropyrrolo[1,2-a]pyrazine (A2) and (1.27 ml, 9.1 mmol) of NEt₃ in DCM (35 ml). Stirring was then carried out for 60 min at RT. The mixture was then washed with water and brine, and the organic phase was dried over MgSO₄, filtered and concentrated in vacuo. CC (chloroform/ethyl acetate 10:1) yielded 1.26 g (4.2 mmol, 55%) of 3-oxo-3-(1-phenyl-3,4-dihydropyrrolo[1,2-a]pyrazin-2(1H)-yl)propanoic acid methyl ester.

b) Synthesis of 3-oxo-3-(1-phenyl-3,4-dihydropyrrolo[1,2-a]pyrazin-2(1H)-yl)propanoic acid A solution of (260 mg, 4.6 mmol) of potassium hydroxide in water (10 ml) was added to a solution of (41.26 g, 0.2 mmol, 55%) of 3-oxo-3-(1-phenyl-3,4-dihydropyrrolo[1,2-a]pyrazin-2(1H)-yl)propanoic acid methyl ester in ethanol (20 ml). The reaction solution was stirred for 3 h at RT and then concentrated in vacuo. The residue was taken up in water and washed twice with ethyl acetate. The aqueous phase was then adjusted to pH 4 with 20% hydrochloric acid and extracted with dichloromethane. The organic phase was concentrated in vacuo, 1.03 g (3.8 mmol, 86%) of 3-oxo-3-(1-phenyl-3,4-dihydropyrrolo[1,2-a]pyrazin-2(1H)-yl)propanoic acid (S5) being obtained as residue.

8. Acylation

CDI (286 mg, 1.76 mmol) was added to a solution of (1.68 mmol) of the corresponding acid S3, S4 or S5 in DCM (27 ml), and stirring was carried out for 1 h at RT. The corresponding amine (1.68 mmol) was then added, and stirring was continued for a further 16 h at RT. A 4N aq. ammonium chloride solution was then added, and the phases were separated. The aqueous phase was extracted twice with DCM. The organic phases were combined and washed with a 1M sodium bicarbonate solution, dried over MgSO₄ and concentrated in vacuo. The crude product was purified by CC (ethyl acetate).

| Example | Structure and name | Precursor | Yield [mg] | MS m/z |
|---|---|---|---|---|
| 83 | 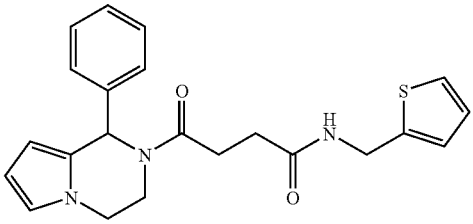<br>oxo-4-(1-phenyl-3,4-dihydropyrrolo[1,2-a]pyrazin-2(1H)-yl)-N-(thiophen-2-ylmethyl)butanamide | S3 | 122 | 394.2 |
| 84 | 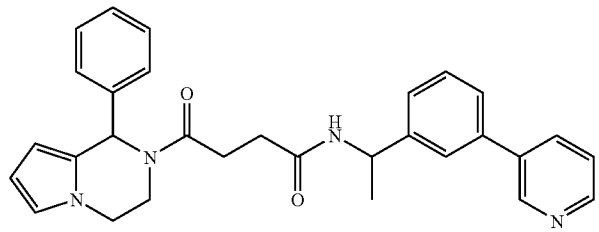<br>4-oxo-4-(1-phenyl-3,4-dihydropyrrolo[1,2-a]pyrazin-2(1H)-yl)-N-(1-(3-(pyridin-3-yl)ethyl)butanamide | S3 | 477 | 479.2 |
| 85 | 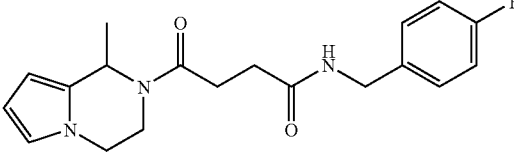<br>N-(4-fluorobenzyl)-4-(1-methyl-3,4-dihydropyrrolo[1,2-a]pyrazin-2(1H)-yl)-4-oxobutanamide | S4 | 201 | 344.1 |
| 86 | 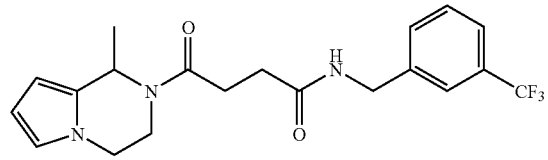<br>4-(1-methyl-3,4-dihydropyrrolo[1,2-a]pyrazin-2(1H)-yl)-4-oxo-N-(3-(trifluoromethyl)benzyl)butanamide | S4 | 341 | 394.1 |
| 89 | 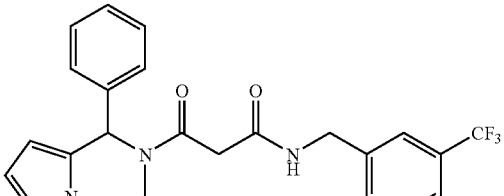<br>3-oxo-3-(1-phenyl-3,4-dihydropyrrolo[1,2-a]pyrazin-2(1H)-yl)-N-(3-(trifluoromethyl)benzyl)propanamide | S5 | 340 | 442.2 |

| Example | Structure and name | Precursor | Yield [mg] | MS m/z |
|---|---|---|---|---|
| 90 | 3-oxo-3-(1-phenyl-3,4-dihydropyrrolo[1,2-a]pyrazin-2(1H)-yl)-N-(3-(trifluoromethyl)benzyl)propanamide | S5 | 541 | 428.2 |

9. Synthesis of the Compound of Example 91

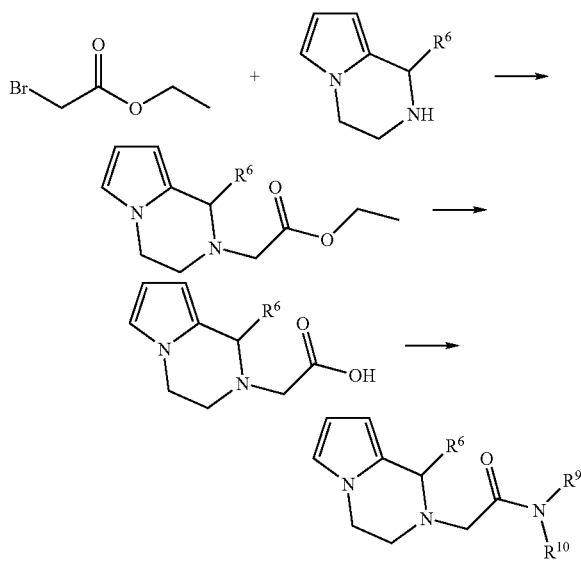

2-(1-Phenyl-3,4-dihydropyrrolo[1,2-a]pyrazin-2(1H)-yl)acetic acid a) Synthesis of 2-(1-phenyl-3,4-dihydropyrrolo[1,2-a]pyrazin-2(1H)-yl)acetic acid methyl ester A mixture of (1.0 g, 5.0 mmol) of 1-phenyl-1,2,3,4-tetrahydropyrrolo[1,2-a]pyrazine, 2-bromoacetic acid ethyl ester (587 µl, 5.3 mmol) and potassium carbonate (1.74 g, 12.6 mmol) in acetonitrile (20 ml) was heated for 2 h under reflux. Water (10 ml) and EA (20 ml) were then added, stirring was carried out for 15 min, and the phases were separated. The organic phase was dried over MgSO₄, filtered and concentrated in vacuo. 1.38 g of 2-(1-phenyl-3,4-dihydropyrrolo[1,2-a]pyrazin-2(1H)-yl)acetic acid methyl ester were obtained as residue and used in the next step without further purification.

b) Synthesis of 2-(1-phenyl-3,4-dihydropyrrolo[1,2-a]pyrazin-2(1H)-yl)acetic acid A solution of (300 mg, 5.3 mmol) of potassium hydroxide in water (10 ml) was added to a solution of (1.38 g crude product, ~5.04 mmol) of 2-(1-phenyl-3,4-dihydropyrrolo[1,2-a]pyrazin-2(1H)-yl)acetic acid methyl ester in ethanol (20 ml). The reaction solution was stirred for 3 h at RT and then concentrated in vacuo. The residue was taken up in water and washed twice with EA. The aqueous phase was then adjusted to pH 4 with 20% hydrochloric acid and extracted with dichloromethane. The organic phase was concentrated in vacuo, 950 mg (3.7 mmol, 74%) of 2-(1-phenyl-3,4-dihydropyrrolo[1,2-a]pyrazin-2(1H)-yl)acetic acid being obtained as residue.

10. Acylation

CDI (286 mg, 1.76 mmol) was added to a solution of (1.68 mmol) of acid S6 in DCM (27 ml), and the mixture was stirred for 1 h at RT. The corresponding amine (1.68 mmol) was then added, and stirring was continued for a further 16 h at RT. A 4N aq. ammonium chloride solution was then added and the phases were separated. The aqueous phase was extracted twice with DCM. The organic phases were combined and washed with a 1M sodium bicarbonate solution, dried over MgSO₄ and concentrated in vacuo. The crude product was purified by CC (ethyl acetate).

| Example | Structure and name | Precursor | Yield | MS m/z |
|---|---|---|---|---|
| 91 | 2-(1-phenyl-3,4-dihydropyrrolo[1,2-a]pyrazin-2(1H)-yl)-N-(3-(trifluoromethyl)benzyl)acetamide | S6 | 431 69 | 414.2 |

11. Biological Data
12. Fluorescence Assay Using a Voltage Sensitive Dye

Human CHO-K1 cells expressing KCNQ2/3 channels are cultivated adherently at 37° C., 5% $CO_2$ and 95% humidity in cell culture bottles (e.g. 80 cm² TC flasks, Nunc) with MEM Alpha Medium (1×, liquid, Invitrogen, #22571), 10% fetal calf serum (FCS) (Invitrogen, #10270-106, heat-inactivated) and the necessary selection antibiotics.

Before being sown out for the measurements, the cells are washed with a 1×DPBS buffer without $Ca^{2+}/Mg^{2+}$ (e.g. Invitrogen, #14190-094) and detached from the bottom of the culture vessel by means of Accutase (PAA Laboratories, #L11-007) (incubation with Accutase for 15 min at 37° C.). The cell count then present is determined using a CASY™ cell counter (TCC model, Schärfe System) in order subsequently to apply 20,000 cells/well/100 μl of the described nutrient medium to 96-well measuring plates of the Corning™ CellBIND™ type (Flat Clear Bottom Black Polystyrene Microplates, #3340). Incubation is then carried out for one hour at room temperature, without gassing or adjusting the humidity, followed by incubation for 24 hours at 37° C., 5% $CO_2$ and 95% humidity.

The voltage-sensitive fluorescent dye from the Membrane Potential Assay Kit (Red™ Bulk format part R8123 for FLIPR, Molecular Devices™) is prepared by dissolving the contents of a vessel *Membrane Potential Assay Kit Red Component A* in 200 ml of extracellular buffer (ES buffer, 120 mM NaCl, 1 mM KCl, 10 mM HEPES, 2 mM $CaCl_2$, 2 mM $MgCl_2$, 10 mM glucose; pH 7.4). After removal of the nutrient medium, the cells are washed with 200 μl of ES buffer, then covered with a layer of 100 μl of the dye solution prepared above and incubated for 45 min at room temperature with the exclusion of light.

The fluorescence measurements are carried out with a BMG Labtech FLUOstar™ or BMG Labtech POLARstar™ instrument (525 nm excitation, 560 nm emission, Bottom Read mode). After incubation of the dye, 50 μA of the test substances in the desired concentrations, or 50 μl of ES buffer for control purposes, are introduced into separate cavities of the measuring plate and incubated for 30 min at room temperature while being shielded from light. The fluorescence intensity of the dye is then measured for 5 min and the fluorescence value $F_1$ of each well is thus determined at a given, constant time. 15 μl of a 100 mM KCl solution (final concentration 92 mM) are then added to each well. The change in fluorescence is subsequently measured until all the relevant measured values have been obtained (mainly 5-30 min). At a given time after KCl application, a fluorescence value $F_2$ is determined, in this case at the time of the fluorescence peak.

For calculation, the fluorescence intensity $F_2$ is compared with the fluorescence intensity $F_1$, and the agonistic activity of the target compound on the potassium channel is determined therefrom. $F_2$ and $F_1$ are calculated as follows:

$$\left(\frac{F_{2K} - F_{1K}}{F_{1K}}\right) \times 100 = \left(\frac{\Delta F}{F}\right)_K (\%)$$

In order to determine whether a substance has an agonistic effect, $$\frac{\Delta F}{F},$$

for example, can be compared with $$\left(\frac{\Delta F}{F}\right)_K$$

control cells.

$$\left(\frac{\Delta F}{F}\right)_K$$

determined by adding to the reaction batch only the buffer solution instead of the substance to be tested, determining the value $F_{1K}$ of the fluorescence intensity, adding the potassium ions as described above and measuring a value $F_{2K}$ of the fluorescence intensity. Then $F_{2K}$ and $F_{1K}$ are calculated as follows:

$$\left(\frac{F_2 - F_1}{F_1}\right) \times 100 = \frac{\Delta F}{F}(\%)$$

A substance has an agonistic activity on the potassium channel when $$\frac{\Delta F}{F}$$

is greater than $$::\left(\frac{\Delta F}{F}\right)_K \frac{\Delta F}{F} > \left(\frac{\Delta F}{F}\right)_K$$

Independently of the comparison of $$\frac{\Delta F}{F} \text{ with } \left(\frac{\Delta F}{F}\right)_K,$$

it is also possible to conclude that a target compound has agonistic activity if an increase in $$\frac{\Delta F}{F}$$

is to be observed as the dosage of the target compound increases. Calculations of $EC_{50}$ and $IC_{50}$ values are carried out with the aid of "Prism 4" software (GraphPad Software™).

The following compounds were tested by way of example:

TABLE 1

| BMG AG %@10 μmol/EC50 values | | |
|---|---|---|
| i. ii. Example | iii. BMG AG %@10 μm | BMG EC50 [μM] |
| 2 | 84 | |
| 1 | 69 | |
| 82 | | 5.28 |
| 5 | 28 | |
| 37 | 24 | |

TABLE 1-continued

BMG AG %@10 μmol/EC50 values

| i. ii. Example | iii. BMG AG %@10 μm | BMG EC50 [μM] |
|---|---|---|
| 20 | 21 | |
| 89 | | 4.55 |
| 8 | | 2.97 |
| 86 | | 11.6 |
| 80 | 10 | |
| 91 | 9 | |
| 92 | 7 | |
| 88 | 5 | |
| 87 | 3 | |
| 85 | 0 | |
| 90 | −20 | |
| 76 | | 3.29 |
| 81 | | 2.95 |
| 83 | | 14.3 |

Voltage Clamp Measurements

In order to confirm a KCNQ2/3-agonistic action of the substances electrophysiologically, patch-clamp measurements (Hamill et al., 1981) were carried out in voltage clamp mode on a stably transfected hKCNQ2/3 CHO-K1 cell line. After formation of the gigaseal, the cells were first clamped at a holding potential of −60 mV. Thereafter, depolarizing voltage jumps were applied up to a potential of +20 mV (increment: 20 mV, duration: 1 second) in order to confirm the functional expression of KCNQ2/3-typical currents. The testing of the substances was carried out at a potential of −40 mV. The increase in current induced by retigabine (10 at −40 mV was first recorded as a positive control on each cell. After complete washing out of the retigabine effect (duration: 80 s), the test substance was applied.

See: Hamill O P, Marty A, Neher E, Sakmann B, Sigworth F J.: Improved patch-clamp techniques for high-resolution current recording from cells and cell-free membrane patches. *Pflugers Arch.* 1981 August; 391(2):85-100.

The following compounds were tested by way of example:

TABLE 2

MAN rel. eff. @ 10 μmol

| Example No. | MAN rel eff @ 10 μM [RG = 1] |
|---|---|
| 76 | 0.75 |
| 81 | 0.25 |
| 82 | 0.11 |
| 90 | −0.46 |

Bennett Model: Neuropathic Pain in the Mouse and in the Rat

The study of activity in neuropathic pain was carried out in the Bennett model (chronic constriction injury; Bennett and Xie, 1988, Pain 33: 87-107). Sprague-Dawley rats weighing 140-160 g are provided, under Narcoren narcosis, with four loose ligations of the right nervus ischiaticus. NMRI mice weighing 16-18 g are provided, under Ketavet-Rompun narcosis, with three loose ligations of the right nervus ischiaticus. The animals develop hypersensitivity of the paw innervated by the damaged nerve, and after a one-week recovery phase, the hypersensitivity is quantified over a period of about four weeks by means of a 4° C. cold metal plate (cold allodynia). The animals are observed on the plate for a period of 2 min and the number of reactions of pulling away the damaged paw is measured. Relative to the initial value before administration of the test substance, the action of the substance is determined over a period of one hour at four points in time (e.g. 15, 30, 45 and 60 min after administration) and the resulting area under the curve (AUC) and the inhibition of cold allodynia at the individual measuring points are expressed as percentage activity relative to the vehicle control (AUC) or to the initial value (individual measuring points). The size of the group is n=10, the significance of an anti-allodynic action (*=p<0.05) is determined by means of a variance analysis with repeated measurement and a post hoc analysis according to Bonferroni.

By way of example, the activity of Example 2 was tested in the Bennett model (i.v. administration). At a dose of 10 mg/kg, 40% MPE was measured.

Chung Model: Mononeuropathic Pain after Spinal Nerve Ligation

Animals: Male Sprague-Dawley rats (140-160 g) from a commercial breeder (Janvier, Genest St. Isle, France) were kept under a 12:12 h light-dark rhythm. The animals received food and tap water ad libitum. A period of one week was observed between delivery of the animals and the operation. After the operation, the animals were tested several times over a period of 4-5 weeks, a washing-out time of at least one week being observed.

Description of the model: Under pentobarbital narcosis (Narcoren®, 60 mg/kg i.p., Merial GmbH, Hallbergmoos, Germany), the left L5, L6 spinal nerves were exposed by removing a section of the paravertebral muscle and a section of the left spinous process of the L5 lumbar vertebral body. Spinal nerves L5 and L6 were carefully isolated and bound with a tight ligation (NC-silk black, USP 5/0, metric 1, Braun Melsungen A G, Melsungen, Germany) (Kim and Chung 1992). After ligation, the muscle and the adjacent tissue were sutured and the wound was closed by means of metal clamps.

After a recovery time of one week, the animals were placed in cages having a wire floor, for the purposes of measuring mechanical allodynia. The pull-back threshold was measured on the ipsi- and/or contra-lateral rear paw by means of an electronic from Frey Filamentes (Somedic A B, Malmö, Sweden). The median of five stimulations gave a measuring time. The animals were tested 30 minutes before and at various times after administration of test substance or vehicle solution. The data were determined as % maximum possible effect (% MPE) from the preliminary tests on the individual animals (=0 MPE) and the test values of an independent sham control group (=100% MPE). Alternatively, the pull-back threshold was represented in grams.

Statistical evaluation: $ED_{50}$ values and 95% confidence ranges were determined at the time of maximum effect by means of semilogarithmic regression analysis. The data were analyzed by variance analysis with repeated measurements and a post hoc analysis according to Bonferroni. The size of the group was usually n=10.

See: Kim, S. H. and Chung, J. M., An experimental model for peripheral neuropathy produced by segmental spinal nerve ligation in the rat, Pain, 50 (1992) 355-363.

By way of example, the activity of Example 2 was tested in the Chung model (i.v. administration). An $ED_{50}$ of 2.8 mg/kg was determined. Silica gel 60 (particle size 0.040-0.063 mm) from E. Merck, Darmstadt, Germany was used as the mobile phase for column chromatography.

Abbreviations:
aq. aqueous
brine saturated aqueous NaCl solution
CDT 1,1'-carbonyldiimidazole
d day(s)
DCC N,N'-dicyclohexylcarbodiimide
DCM dichloromethane
DCE 1,2-dichloroethane DIC diisopropylaminoethyl chloride hydrochloride
DMAP 4-dimethylaminopyridine
EA ethyl acetate
ether diethyl ether
sat. saturated
h hour(s)
HATU O-(7-azabenzotriazol-1-yl)-N,N,N',N'-tetramethyluronium hexafluorophosphate
HBTU O-(benzotriazol-1-yl)-N,N,N',N'-tetramethyluronium hexafluorophosphate
m/z mass/charge ratio
MeCN acetonitrile
MeOH methanol
min minutes
MS mass spectroscopy
NEt$_3$ triethylamine
PS diimide a polymer-bonded carbodiimide having the following structure:

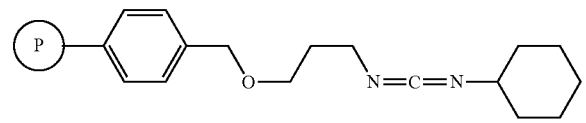

loading: 0.9-1.4 mmol/g; particle size: 75-150 μm

RT room temperature 23±7° C.
CC column chromatography on silica gel
TFA trifluoroacetic acid
THF tetrahydrofuran The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A method of treating or inhibiting a condition selected from the group consisting of pain mediated through the KCNQ2/3 K$^+$ channel, epilepsy, migraine and anxiety in a patient in need thereof, said method comprising administering to said patient a pharmacologically effective amount of a substituted tetrahydropyrrolopyrazine compound corresponding to formula I:

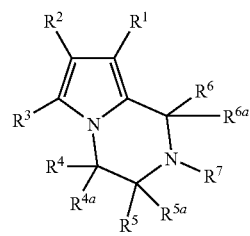

wherein
$R^1$, $R^2$ and $R^3$ independently of one another represent hydrogen, saturated or unsaturated branched or unbranched $C_{1-6}$-alkyl which is unsubstituted or mono- or poly-substituted, F, Cl, Br, I, CN, NH$_2$, NH—C$_{1-6}$-alkyl, N(C$_{1-6}$alkyl)$_2$, NH-alkylaryl, NH-heteroaryl, OH, O—C$_{1-6}$-alkyl, CF$_3$, benzyloxy, phenoxy, phenyl, pyridyl, alkylaryl, thienyl or furyl; or
$R^1$ and $R^2$ or $R^2$ and $R^3$ form a ring and together denote

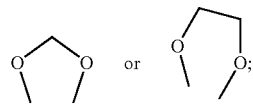

$R^4$ and $R^5$ independently of one another represent H, F, Cl, Br, I, or C$_{1-6}$-alkyl;
$R^6$ represents branched or unbranched C$_{1-6}$-alkyl which is unsubstituted or mono- or poly-substituted, aryl or heteroaryl which are unsubstituted or mono- or poly-substituted, or unsubstituted or mono- or poly-substituted aryl or heteroaryl linked via a C$_{1-3}$-alkyl chain;
$R^{4a}$, $R^{5a}$ and $R^{6a}$ independently of one another represent H or C$_{1-6}$-alkyl; and
$R^7$ represents (CH$_2$)$_t$C(=O)R$^8$, (C=O)(CH$_2$)$_m$NR$^{11}$R$^{12}$, C(=O)(CH$_2$)$_n$(C=O)R$^8$ or (CH$_2$)$_s$NHC(=O)R$^8$, wherein
m represents 1, 2 or 3;
n, t and s each represents 1, 2, 3 or 4;
$R^8$ denotes C$_{1-6}$-alkyl, saturated or unsaturated, branched or unbranched, unsubstituted or mono- or poly-substituted; aryl or C$_{3-8}$-cycloalkyl, in each case unsubstituted or monosubstituted or substituted two times; or aryl, heteroaryl, heterocyclyl or C$_{3-8}$-cycloalkyl linked via a C$_{1-5}$-alkyl chain and in each case unsubstituted or mono- or poly-substituted, wherein the alkyl chain in each case can be saturated or unsaturated, branched or unbranched; NR$^9$R$^{10}$; wherein
$R^9$ and $R^{10}$ independently of one another represent H; C$_{1-6}$-alkyl, in each case saturated or unsaturated, branched or unbranched, mono- or poly-substituted or unsubstituted; aryl or heteroaryl, in each case unsubstituted or mono- or poly-substituted; heterocyclyl or C$_{3-8}$-cycloalkyl, in each case saturated or unsaturated, mono- or poly-substituted or unsubstituted; C(=O)R$^{20}$; SO$_2$R$^{13}$; or aryl, C$_{3-8}$-cycloalkyl, heterocyclyl or heteroaryl bonded via C$_{1-3}$-alkyl and in each case mono- or poly-substituted or unsubstituted, wherein the alkyl chain in each case can be saturated or unsaturated, branched or unbranched; or
$R^9$ and $R^{10}$ together represent CH$_2$CH$_2$OCH$_2$CH$_2$, CH$_2$CH$_2$NR$^{14}$CH$_2$CH$_2$ or (CH$_2$)$_{3-6}$;
$R^{11}$ and $R^{12}$ independently of one another represent H, saturated or unsaturated branched or unbranched C$_{1-6}$-alkyl which is unsubstituted or mono- or poly-substituted, heterocyclyl or C$_{3-8}$-cycloalkyl in each case saturated or unsaturated and mono- or poly-substituted or unsubstituted, (=O)R$^{20}$, SO$_2$R$^{13}$, or aryl, C$_{3-8}$-cycloalkyl, heterocyclyl or heteroaryl bonded via C$_{1-3}$-alkyl and in each case mono- or poly-substituted or unsubstituted, wherein the alkyl chain in each case can be saturated or unsaturated, branched or unbranched; or
$R^{11}$ and $R^{12}$ together represent CH$_2$CH$_2$OCH$_2$CH$_2$, CH$_2$CH$_2$NR$^{14}$CH$_2$CH$_2$ or (CH$_2$)$_{3-6}$, wherein
$R^{14}$ denotes H, saturated or unsaturated branched or unbranched C$_{1-6}$-alkyl which is unsubstituted or mono- or poly-substituted, saturated or unsaturated C$_{3-8}$-cycloalkyl which is unsubstituted or mono- or poly-substituted, aryl or heteroaryl which are unsubstituted or mono- or poly-substituted, $C(=O)R^{13}$, or aryl, $C_{3-8}$-cycloalkyl or heteroaryl bonded via $C1\_3$-alkyl and in each case mono- or poly-substituted or unsubstituted;

$R^{13}$ denotes saturated or unsaturated branched or unbranched $C_{1-6}$-alkyl which is unsubstituted or mono- or poly-substituted; aryl, heteroaryl or $C_{3-8}$-cycloalkyl, in each case unsubstituted or mono- or poly-substituted; or aryl, heteroaryl or $C_{3-8}$-cycloalkyl linked via a saturated or unsaturated branched or unbranched $C_{1-5}$-alkyl chain and in each case unsubstituted or mono- or poly-substituted; and $R^{20}$ denotes saturated or unsaturated branched or unbranched $C_{1-6}$-alkyl which is unsubstituted or mono- or poly-substituted; aryl, heteroaryl or $C_{3-8}$-cycloalkyl, in each case unsubstituted or mono- or poly-substituted; $NR^{21}R^{22}$; or aryl, heteroaryl or $C_{3-8}$-cycloalkyl linked via a saturated or unsaturated branched or unbranched $C_{1-5}$-alkyl chain and in each case unsubstituted or mono- or poly-substituted, wherein $R^{21}$ and $R^{22}$ independently of one another denote saturated or unsaturated branched or unbranched $C_{1-6}$-alkyl which is unsubstituted or mono- or poly-substituted; aryl, heteroaryl or $C_{3-8}$-cycloalkyl, in each case unsubstituted or mono- or poly-substituted; or aryl, heteroaryl or $C_{3-8}$-cycloalkyl linked via a saturated or unsaturated branched or unbranched $C_{1-5}$-alkyl chain and in each case unsubstituted or mono- or poly-substituted;

wherein:
if an alkyl group, heterocyclyl group or cycloalkyl group is mono- or poly-substituted, the substituents are independently selected from the group consisting of F, Cl, Br, I, —CN, $NH_2$, NH—$C_{1-6}$-alkyl, NH—$C_{1-6}$-alkyl-OH, $C_{1-6}$-alkyl, N($C_{1-6}$-alkyl)$_2$, N($C_{1-6}$-alkyl-OH)$_2$, $NO_2$, SH, S—$C_{1-6}$alkyl, S-benzyl, O—$C_{1-6}$-alkyl, OH, O—$C_{1-6}$-alkyl-OH, =O, O-benzyl, $C(=O)C_{1-6}$-alkyl, $CO_2H$, $CO_2$—$C_{1-6}$-alkyl, phenyl and benzyl; and if an aryl group or a heteroaryl group is mono- or poly-substituted, the substituents are independently selected from the group consisting of F, Cl, Br, I, CN, $NH_2$, NH—$C_{1-6}$-alkyl, NH—$C_{1-6}$-alkyl-OH, N($C_{1-6}$-alkyl)$_2$, N($C_{1-6}$-alkyl-OH)$_2$, $NO_2$, SH, S—$C_{1-6}$-alkyl, OH, O—$C_{1-6}$-alkyl, O—$C_{1-6}$alkyl-OH, $C(=O)C_{1-6}$-alkyl, $C(=O)NHC_{1-6}$-alkyl; $C(=O)$-aryl; $C(=O)$—N-morpholine; $C(=O)$-piperidine; $(C=O)$-pyrrolidine; $(C=O)$-piperazine; $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $SCF_3$, $CF_3$,

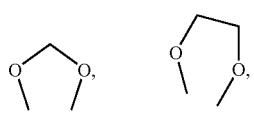

$C_{1-6}$-alkyl pyrrolidinyl, piperidinyl, morpholinyl, benzyloxy, phenoxy, phenyl, pyridyl, alkylaryl, thienyl and furyl; wherein said substituents optionally may be substituted with substituents selected from the foregoing group other than an aryl or heteroaryl ring;

in the form of a pure stereoisomer or a mixture of stereoisomers in any mixing ratio;

or a physiologically acceptable salt thereof.

2. A method according to claim 1, wherein said condition is pain mediated through the KCNQ2/3$K^+$ channel selected from the group consisting of acute pain, chronic pain, neuropathic pain, muscular pain and inflammatory pain.

3. A method according to claim 1, wherein said compound is in the form of an isolated enantiomer or an isolated diastereomer.

4. A method according to claim 1, wherein $R^7$ represents $CH_2C(=O)R^8$, $(C=O)(CH_2)_mNR^{11}R^{12}$ or $C(=O)(CH_2)_n(C=O)R^8$, wherein m represents 1, 2 or 3, and n represents 1, 2, 3 or 4.

5. A method according to claim 1, wherein $R^1$, $R^2$ and $R^3$ independently of one another represent hydrogen or branched or unbranched $C_{1-6}$-alkyl.

6. A method according to claim 1, wherein $R^4$ and $R^5$ independently of one another represent H or $C_{1-6}$-alkyl.

7. A method according to claim 1, wherein $R^6$ denotes phenyl, thienyl, furyl, pyridyl or benzyl, in each case unsubstituted or mono- or poly-substituted by $OCH_3$, F, Cl, $CH_3$, isopropyl or

or
$R^6$ denotes methyl or tert-butyl.

8. A method according to claim 1, wherein $R^7$ represents $CH_2CH_2C(=O)R^8$, $CH_2CH_2CH_2C(=O)R^8$ or $CH_2CH_2CH_2CH_2C(=O)R^8$.

9. A method according to claim 1, wherein $R^8$ represents $NR^9R^{10}$, wherein $R^9$ represents H, and $R^{10}$ denotes aryl, heteroaryl, heterocyclyl or $C_{3-8}$-cycloalkyl optionally bonded via a saturated or unsaturated branched or unbranched $C_{1-3}$-alkyl chain and in each case unsubstituted or mono- or poly-substituted; or $R^{10}$ denotes saturated, unsubstituted, branched or unbranched $C_{1-6}$-alkyl; or $R^9$ and $R^{10}$ together represent $CH_2CH_2OCH_2CH_2$, $CH_2CH_2NR^{14}CH_2CH_2$, $CH_2CH_2CH_2CH_2$ or $CH_2CH_2CH_2CH_2CH_2$, wherein $R^{14}$ denotes H; benzyl or phenyl, in each case unsubstituted or mono- or poly-substituted; or $C(=O)R^{13}$.

10. A method according to claim 9, wherein $R^8$ represents $NR^9R^{10}$, wherein $R^9$ represents H and $R^{10}$ denotes phenyl, benzyl, phenethyl, methylthienyl, methylfuryl, methylpyridyl, ethylthienyl, ethylfuryl or ethylpyridyl, in each case mono- or poly-substituted; piperidyl, pyrrolidinyl, methylpiperidyl, methyl-pyrrolidinyl, ethylpiperidyl or ethylpyrrolidinyl, in each case mono- or poly-substituted; cyclopropyl, cyclobutyl, cyclopentyl or cyclohexyl; propyl, butyl or pentyl; or $R^9$ and $R^{10}$ together represent $CH_2CH_2OCH_2CH_2$, $CH_2CH_2NR^{14}CH_2CH_2$, $CH_2CH_2CH_2CH_2$ or $CH_2CH_2CH_2CH_2CH_2$, wherein $R^{14}$ denotes H; benzyl or phenyl, in each case unsubstituted or mono- or poly-substituted; or $C(=O)CH_3$.

11. A method according to claim 1, wherein $R^7$ denotes $(C=O)CH_2NR^{11}R^{12}$, $(C=O)CH_2CH_2NR^{11}R^{12}$ or $(C=O)CH_2CH_2CH_2NR^{11}R^{12}$, wherein $R^{11}$ denotes $C(=O)R^{20}$, wherein $R^{20}$ represents phenyl, furyl, benzyl, phenethyl, phenethenyl, propylphenyl or cyclopropyl, in each case unsubstituted or mono- or poly-substituted; or methyl, ethyl, propyl, butyl or $NR^{21}R^{22}$, wherein $R^{21}$ and $R^{22}$ independently of one another represent H or $C_{1-6}$-alkyl; and $R^{12}$ denotes H, branched or unbranched $C_{1-6}$-alkyl, or $C_{3-8}$-cycloalkyl.

12. A method according to claim 11, wherein $R^{11}$ denotes $C(=O)R^{20}$, wherein $R^{20}$ represents phenyl, benzyl, phenethyl or propylphenyl, in each case unsubstituted or mono- or poly-substituted by $CF_3$, or $CH_3$; cyclopropyl, unsubstituted or substituted by phenyl; furyl, or $NR^{21}R^{22}$, wherein $R^{21}$ and $R^{22}$ independently of one another represent H, $CH_3$, tert-butyl or isopropyl; and $R^{12}$ denotes H, methyl, ethyl, propyl, butyl or cyclopropyl.

13. A method of treating or inhibiting a condition selected from the group consisting of pain mediated through the $KCNQ2/3K^+$ channel, epilepsy, migraine and anxiety in a patient in need thereof, said method comprising administering to said patient a pharmacologically effective amount of a compound selected from the group consisting of:

4-[1-(4-chloro-phenyl)-3,4-dihydro-1H-pyrrolo[1,2-a]pyrazin-2-yl]-4-oxo-N-(3-trifluoromethyl-benzyl)-butyramide;

4-oxo-4-(1-phenyl-3,4-dihydro-1H-pyrrolo[1,2-a]pyrazin-2-yl)-N-(3-trifluoromethyl-benzyl)-butyramide;

N-sec-butyl-2-[1-(2-methoxy-phenyl)-3,4-dihydro-1H-pyrrolo[1,2-a]pyrazin-2-yl]-acetamide;

N-cyclopropyl-3-[1-(3-fluoro-phenyl)-3,4-dihydro-1H-pyrrolo[1,2-a]pyrazin-2-yl]-3-oxo-propionamide;

4-oxo-4-(1-m-tolyl-3,4-dihydro-1H-pyrrolo[1,2-a]pyrazin-2-yl)-N-(3-trifluoromethyl-benzyl)-butyramide;

3-{2-[1-(2-chloro-phenyl)-3,4-dihydro-1H-pyrrolo[1,2-a]pyrazin-2-yl]-2-oxo-ethyl}-1,1-dimethyl-urea;

4-[1-(4-fluoro-phenyl)-3,4-dihydro-1H-pyrrolo[1,2-a]pyrazin-2-yl]-N-isobutyl-4-oxo-butyramide;

2-[1-(2,3-dihydro-benzo[1,4]dioxin-6-yl)-3,4-dihydro-1H-pyrrolo[1,2-a]pyrazin-2-yl]-N-(3-trifluoromethyl-benzyl)-acetamide;

2-[1-(2,3-dihydro-benzo[1,4]dioxin-6-yl)-3,4-dihydro-1H-pyrrolo[1,2-a]pyrazin-2-yl]-N-p-tolyl-acetamide;

3-tert-butyl-1-{2-[1-(2,4-difluoro-phenyl)-3,4-dihydro-1H-pyrrolo[1,2-a]pyrazin-2-yl]-2-oxo-ethyl}-1-isopropyl-urea;

2-[1-(2,3-dihydro-benzo[1,4]dioxin-6-yl)-3,4-dihydro-1H-pyrrolo[1,2-a]pyrazin-2-yl]-N-isopropyl-acetamide;

3-tert-butyl-1-isopropyl-1-[2-oxo-2-(1-m-tolyl-3,4-dihydro-1H-pyrrolo[1,2-a]pyrazin-2-yl)-ethyl]-urea;

N-cyclopropyl-N-[2-(1-furan-3-yl-3,4-dihydro-1H-pyrrolo[1,2-a]pyrazin-2-yl)-2-oxo-ethyl]-4-methyl-benzamide;

cyclopropanecarboxylic acid {2-[1-(3,4-dichloro-phenyl)-3,4-dihydro-1H-pyrrolo[1,2-a]pyrazin-2-yl]-2-oxo-ethyl}-isopropyl-amide;

1-cyclopropyl-1-{2-[1-(2,4-difluoro-phenyl)-3,4-dihydro-1H-pyrrolo[1,2-a]pyrazin-2-yl]-2-oxo-ethyl}-3-isopropyl-urea;

1-(4-acetyl-piperazin-1-yl)-2-[1-(2,4-difluoro-phenyl)-3,4-dihydro-1H-pyrrolo[1,2-a]pyrazin-2-yl]-ethanone;

furan-2-carboxylic acid cyclopropyl-{2-[1-(3,4-dichloro-phenyl)-3,4-dihydro-1H-pyrrolo[1,2-a]pyrazin-2-yl]-2-oxo-ethyl}-amide;

N-tert-butyl-N-[2-oxo-2-(1-p-tolyl-3,4-dihydro-1H-pyrrolo[1,2-a]pyrazin-2-yl)-ethyl]-isobutyramide;

N-cyclopropyl-N-{2-[1-(3,4-dichloro-phenyl)-3,4-dihydro-1H-pyrrolo[1,2-a]pyrazin-2-yl]-2-oxo-ethyl}-isobutyramide;

2-(1-(3-methoxyphenyl)-3,4-dihydropyrrolo[1,2-a]pyrazin-2(1H)-yl)-N-(3-(trifluoromethyl)benzyl)acetamide;

1-ethyl-3,3-dimethyl-1-[2-oxo-2-(1-phenyl-3,4-dihydro-1H-pyrrolo[1,2-a]pyrazin-2-yl)-ethyl]-urea;

quinoline-8-sulfonic acid {2-[1-(2,4-difluoro-phenyl)-3,4-dihydro-1H-pyrrolo[1,2-a]pyrazin-2-yl]-2-oxo-ethyl}-ethyl-amide;

N-cyclopropyl-2-(1-p-tolyl-3,4-dihydro-1H-pyrrolo[1,2-a]pyrazin-2-yl)-acetamide;

cyclopropanecarboxylic acid tert-butyl-[2-oxo-2-(1-p-tolyl-3,4-dihydro-1H-pyrrolo[1,2-a]pyrazin-2-yl)-ethyl]-amide;

furan-2-carboxylic acid tert-butyl-{2-[1-(3,4-dichloro-phenyl)-3,4-dihydro-1H-pyrrolo[1,2-a]pyrazin-2-yl]-2-oxo-ethyl}-amide;

2-[1-(2-chloro-phenyl)-3,4-dihydro-1H-pyrrolo[1,2-a]pyrazin-2-yl]-1-piperidin-1-yl-ethanone;

2-phenyl-cyclopropanecarboxylic acid ethyl-[2-oxo-2-(1-phenyl-3,4-dihydro-1H-pyrrolo[1,2-a]pyrazin-2-yl)-ethyl]-amide;

N-(4-fluoro-phenyl)-4-[1-(3-methoxy-phenyl)-3,4-dihydro-1H-pyrrolo[1,2-a]pyrazin-2-yl]-4-oxo-butyramide;

N-ethyl-N-[2-oxo-2-(1-phenyl-3,4-dihydro-1H-pyrrolo[1,2-a]pyrazin-2-yl)-ethyl]-butyramide;

N-(1,2-dimethyl-propyl)-2-(1-p-tolyl-3,4-dihydro-1H-pyrrolo[1,2-a]pyrazin-2-yl)-acetamide;

N-sec-butyl-2-(1-p-tolyl-3,4-dihydro-1H-pyrrolo[1,2-a]pyrazin-2-yl)-acetamide;

N-{2-[1-(3,4-dichloro-phenyl)-3,4-dihydro-1H-pyrrolo[1,2-a]pyrazin-2-yl]-2-oxo-ethyl}-N-ethyl-isobutyramide;

4-[1-(3-methoxy-phenyl)-3,4-dihydro-1H-pyrrolo[1,2-a]pyrazin-2-yl]-4-oxo-N-pyridin-4-ylmethyl-butyramide;

furan-2-carboxylic acid isopropyl-{2-[1-(4-isopropyl-phenyl)-3,4-dihydro-1H-pyrrolo[1,2-a]pyrazin-2-yl]-2-oxo-ethyl}-amide;

1-[1-(3-methoxy-phenyl)-3,4-dihydro-1H-pyrrolo[1,2-a]pyrazin-2-yl]-3-morpholin-4-yl-propane-1,3-dione;

2-(1-p-tolyl-3,4-dihydro-1H-pyrrolo[1,2-a]pyrazin-2-yl)-N-(3-trifluoromethyl-benzyl)-acetamide;

N-pyridin-3-ylmethyl-2-(1-p-tolyl-3,4-dihydro-1H-pyrrolo[1,2-a]pyrazin-2-yl)-acetamide;

2-[1-(2,4-difluoro-phenyl)-3,4-dihydro-1H-pyrrolo[1,2-a]pyrazin-2-yl]-N-furan-2-ylmethyl-acetamide;

N-benzyl-2-(1-p-tolyl-3,4-dihydro-1H-pyrrolo[1,2-a]pyrazin-2-yl)-acetamide;

N-(3,4-dimethyl-phenyl)-3-[1-(3-methoxy-phenyl)-3,4-dihydro-1H-pyrrolo[1,2-a]pyrazin-2-yl]-3-oxo-propionamide;

4-[1-(3-chloro-phenyl)-3,4-dihydro-1H-pyrrolo[1,2-a]pyrazin-2-yl]-N-isopropyl-4-oxo-butyramide;

N-(1-benzyl-piperidin-4-yl)-2-(1-p-tolyl-3,4-dihydro-1H-pyrrolo[1,2-a]pyrazin-2-yl)-acetamide;

2-[1-(4-chloro-phenyl)-3,4-dihydro-1H-pyrrolo[1,2-a]
pyrazin-2-yl]-1-[4-(2-chloro-phenyl)-piperazin-1-yl]-
ethanone;
N-(1-benzyl-piperidin-4-yl)-2-[1-(4-chloro-phenyl)-3,4-
dihydro-1H-pyrrolo[1,2-a]pyrazin-2-yl]-acetamide;
1-(4-benzo[1,3]dioxol-5-ylmethyl-piperazin-1-yl)-2-[1-
(4-chloro-phenyl)-3,4-dihydro-1H-pyrrolo[1,2-a]
pyrazin-2-yl]-ethanone;
N-phenethyl-2-(1-p-tolyl-3,4-dihydro-1H-pyrrolo[1,2-a]
pyrazin-2-yl)-acetamide;
2-[1-(3,4-dichloro-phenyl)-3,4-dihydro-1H-pyrrolo[1,2-
a]pyrazin-2-yl]-N-(2-pyridin-2-yl-ethyl)-acetamide;
1-(4-benzo[1,3]dioxol-5-ylmethyl-piperazin-1-yl)-2-(1-
p-tolyl-3,4-dihydro-1H-pyrrolo[1,2-a]pyrazin-2-yl)-
ethanone;
2-[1-(3,4-dichloro-phenyl)-3,4-dihydro-1H-pyrrolo[1,2-
a]pyrazin-2-yl]-N-pyridin-3-ylmethyl-acetamide;
1-(4-benzo[1,3]dioxol-5-ylmethyl-piperazin-1-yl)-2-[1-
(2-chloro-phenyl)-3,4-dihydro-1H-pyrrolo[1,2-a]
pyrazin-2-yl]-ethanone;
1-(4-benzyl-piperazin-1-yl)-2-[1-(4-chloro-phenyl)-3,4-
dihydro-1H-pyrrolo[1,2-a]pyrazin-2-yl]-ethanone;
2-[1-(4-chloro-phenyl)-3,4-dihydro-1H-pyrrolo[1,2-a]
pyrazin-2-yl]-N-phenethyl-acetamide;
2-[1-(2-chloro-phenyl)-3,4-dihydro-1H-pyrrolo[1,2-a]
pyrazin-2-yl]-N-phenethyl-acetamide;
2-[1-(3,4-dichloro-phenyl)-3,4-dihydro-1H-pyrrolo[1,2-
a]pyrazin-2-yl]-N-(4-fluoro-benzyl)-acetamide;
1-(4-benzyl-piperazin-1-yl)-2-[1-(2-chloro-phenyl)-3,4-
dihydro-1H-pyrrolo[1,2-a]pyrazin-2-yl]-ethanone;
N-cyclohexyl-2-(1-p-tolyl-3,4-dihydro-1H-pyrrolo[1,2-a]
pyrazin-2-yl)-acetamide;
1-(4-benzyl-piperazin-1-yl)-2-(1-p-tolyl-3,4-dihydro-1H-
pyrrolo[1,2-a]pyrazin-2-yl)-ethanone;
2-[1-(4-chloro-phenyl)-3,4-dihydro-1H-pyrrolo[1,2-a]
pyrazin-2-yl]-N-(1,2-dimethyl-propyl)-acetamide;
N-(2-piperidin-1-yl-ethyl)-2-(1-p-tolyl-3,4-dihydro-1H-
pyrrolo[1,2-a]pyrazin-2-yl)-acetamide;
N-(4-fluoro-phenyl)-2-(1-p-tolyl-3,4-dihydro-1H-pyrrolo
[1,2-a]pyrazin-2-yl)-acetamide;
furan-2-carboxylic acid ethyl-[2-oxo-2-(1-p-tolyl-3,4-di-
hydro-1H-pyrrolo[1,2-a]pyrazin-2-yl)-ethyl]-amide;
2-[1-(4-fluoro-phenyl)-3,4-dihydro-1H-pyrrolo[1,2-a]
pyrazin-2-yl]-N-isopropyl-acetamide;
2-[1-(3,4-dichloro-phenyl)-3,4-dihydro-1H-pyrrolo[1,2-
a]pyrazin-2-yl]-N-isobutyl-acetamide;
2-[1-(4-chloro-phenyl)-3,4-dihydro-1H-pyrrolo[1,2-a]
pyrazin-2-yl]-N-(2-pyrrolidin-1-yl-ethyl)-acetamide;
N-benzo[1,3]dioxol-5-ylmethyl-2-(1-p-tolyl-3,4-dihydro-
1H-pyrrolo[1,2-a]pyrazin-2-yl)-acetamide;
2-(1-(4-chlorophenyl)-3,4-dihydropyrrolo[1,2-a]pyrazin-
2(1H)-yl)-N-(4-fluorobenzyl)acetamide;
2-(1-(4-chlorophenyl)-3,4-dihydropyrrolo[1,2-a]pyrazin-
2(1H)-yl)-N-(3-(trifluoromethyl)benzyl)acetamide;
2-(1-(4-chlorophenyl)-3,4-dihydropyrrolo[1,2-a]pyrazin-
2(1H)-yl)-1-(4-(4-methoxyphenyl)piperazin-1-yl)etha-
none;
N-(2,4-dichlorophenethyl)-2-(1-(3,4-dichlorophenyl)-3,
4-dihydropyrrolo[1,2-a]pyrazin-2(1H)-yl)acetamide;
1-(4-(3-chlorophenyl)piperazin-1-yl)-4-(1-m-tolyl-3,4-
dihydropyrrolo[1,2-a]pyrazin-2(1H)-yl)butane-1,4-di-
one;
4-oxo-4-(1-(thiophen-2-yl)-3,4-dihydropyrrolo[1,2-a]
pyrazin-2(1H)-yl)-N-(3-(trifluoromethyl)benzyl)bu-
tanamide;
4-oxo-4-(1-(pyridin-2-yl)-3,4-dihydropyrrolo[1,2-a]
pyrazin-2(1H)-yl)-N-(3-(trifluoromethyl)benzyl)bu-
tanamide;
4-(1-tert-butyl-3,4-dihydropyrrolo[1,2-a]pyrazin-2(1H)-
yl)-4-oxo-N-(3-(trifluoromethyl)benzyl)butanamide;
4-oxo-4-(1-(pyridin-4-yl)-3,4-dihydropyrrolo[1,2-a]
pyrazin-2(1H)-yl)-N-(3-(trifluoromethyl)benzyl)bu-
tanamide;
4-(1-benzyl-3,4-dihydropyrrolo[1,2-a]pyrazin-2(1H)-yl)-
4-oxo-N-(1-(3-(trifluoromethyl)phenyl)ethyl)butana-
mide;
4-oxo-4-(1-phenyl-3,4-dihydropyrrolo[1,2-a]pyrazin-2
(1H)-yl)-N-(1-(3-(trifluoromethyl)phenyl)ethyl)bu-
tanamide;
4-oxo-4-(1-(thiophen-2-yl)-3,4-dihydropyrrolo[1,2-a]
pyrazin-2(1H)-yl)-N-(1-(3-(trifluoromethyl)phenyl)
ethyl)butanamide;
4-oxo-4-(1-phenyl-3,4-dihydropyrrolo[1,2-a]pyrazin-2
(1H)-yl)-N-(thiophen-2-ylmethyl)butanamide;
4-oxo-4-(1-phenyl-3,4-dihydropyrrolo[1,2-a]pyrazin-2
(1H)-yl)-N-(1-(3-(pyridin-3-yl)phenyl)ethyl)butana-
mide;
N-(4-fluorobenzyl)-4-(1-methyl-3,4-dihydropyrrolo[1,2-
a]-pyrazin-2(1H)-yl)-4-oxobutanamide;
4-(1-methyl-3,4-dihydropyrrolo[1,2-a]pyrazin-2(1H)-yl)-
4-oxo-N-(3-trifluoromethyl)benzyl)butanamide;
N-(2-oxo-2-(1-phenyl-3,4-dihydropyrrolo[1,2-a]pyrazin-
2(1H)-yl)ethyl)-3-(3-trifluoromethyl)phenyl)propana-
mide;
N-(2-oxo-2-(1-phenyl-3,4-dihydropyrrolo[1,2-a]pyrazin-
2(1H)-yl)ethyl)-4-phenylbutanamide;
3-oxo-3-(1-phenyl-3,4-dihydropyrrolo[1,2-a]pyrazin-2
(1H)-yl)-N-(3-(trifluoromethyl)benzyl)propanamide;
3-oxo-3-(1-phenyl-3,4-dihydropyrrolo[1,2-a]pyrazin-2
(1H)-yl)-N-(3-(trifluoromethyl)phenyl)propanamide;
2-(1-phenyl-3,4-dihydropyrrolo[1,2-a]pyrazin-2(1H)-yl)-
N-(3-(trifluoromethyl)benzyl)acetamide; and
(E)-3-(2-fluorophenyl)-N-(2-oxo-2-(1-phenyl-3,4-dihy-
dropyrrolo-[1,2-a]pyrazin-2(1H)-yl)ethyl)acrylamide;
or a physiologically acceptable salt thereof.

* * * * *